US007807159B2

(12) United States Patent
Chin et al.

(10) Patent No.: US 7,807,159 B2
(45) Date of Patent: Oct. 5, 2010

(54) ANTIBODIES TO MYOSTATIN

(75) Inventors: Eva Rose Chin, Mystic, CT (US); Larry L. Green, San Francisco, CA (US); Chikwendu Ibebunjo, Quincy, MA (US); Philip Albert Krasney, Old Lyme, CT (US); Junming Yie, Thousand Oaks, CA (US); Joseph Zachweija, Oceanside, CA (US)

(73) Assignees: Amgen Fremont Inc., Fremont, CA (US); Agouron Pharmaceuticals, Inc., San Diego, CA (US)

( * ) Notice: Subject to any disclaimer, the term of this patent is extended or adjusted under 35 U.S.C. 154(b) by 439 days.

(21) Appl. No.: 11/410,886

(22) Filed: Apr. 24, 2006

(65) Prior Publication Data

US 2006/0263354 A1 Nov. 23, 2006

Related U.S. Application Data

(60) Provisional application No. 60/674,933, filed on Apr. 25, 2005.

(51) Int. Cl.
*A61K 39/00* (2006.01)
*C07K 16/28* (2006.01)

(52) U.S. Cl. .............................. 424/133.1; 530/388.25
(58) Field of Classification Search .............. 424/133.1; 530/388.25
See application file for complete search history.

(56) References Cited

U.S. PATENT DOCUMENTS

| 4,399,216 | A | 8/1983 | Axel et al. |
| 4,634,665 | A | 1/1987 | Axel et al. |
| 4,740,461 | A | 4/1988 | Kaufman |
| 4,912,040 | A | 3/1990 | Kaufman et al. |
| 4,959,455 | A | 9/1990 | Clark et al. |
| 5,151,510 | A | 9/1992 | Stec et al. |
| 5,179,017 | A | 1/1993 | Axel et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,591,669 | A | 1/1997 | Krimpenfort et al. |
| 5,612,205 | A | 3/1997 | Kay et al. |
| 5,625,126 | A | 4/1997 | Lonberg et al. |
| 5,633,425 | A | 5/1997 | Lonberg et al. |
| 5,643,763 | A | 7/1997 | Dunn et al. |
| 5,661,016 | A | 8/1997 | Lonberg et al. |
| 5,721,367 | A | 2/1998 | Kay et al. |
| 5,741,957 | A | 4/1998 | Deboer et al. |
| 5,750,172 | A | 5/1998 | Meade et al. |
| 5,756,687 | A | 5/1998 | Denman et al. |
| 5,770,429 | A | 6/1998 | Lonberg et al. |
| 5,789,215 | A | 8/1998 | Berns et al. |
| 5,789,650 | A | 8/1998 | Lonberg et al. |
| 5,814,318 | A | 9/1998 | Lonberg et al. |
| 5,827,690 | A | 10/1998 | Meade et al. |
| 5,916,771 | A | 6/1999 | Hori et al. |
| 5,939,598 | A | 8/1999 | Kucherlapati et al. |
| 5,959,177 | A | 9/1999 | Hein et al. |
| 5,985,615 | A | 11/1999 | Jakobovits et al. |
| 5,998,209 | A | 12/1999 | Jokobovits et al. |
| 6,046,037 | A | 4/2000 | Hiatt et al. |
| 6,075,181 | A | 6/2000 | Kucherlapati et al. |
| 6,091,001 | A | 7/2000 | Jakobovits et al. |
| 6,114,598 | A | 9/2000 | Kucherlapati et al. |
| 6,130,364 | A | 10/2000 | Jakobovits et al. |
| 6,150,584 | A | 11/2000 | Kucherlapati et al. |
| 6,162,963 | A | 12/2000 | Kucherlapati et al. |
| 6,210,670 | B1 * | 4/2001 | Berg ..................... 424/153.1 |
| 6,417,429 | B1 | 7/2002 | Hein et al. |
| 6,517,529 | B1 | 2/2003 | Quinn |
| 2003/0138422 | A1 | 7/2003 | Aghajanian et al. |
| 2006/0030522 | A1 | 2/2006 | Knopf et al. |
| 2007/0178095 | A1 * | 8/2007 | Smith et al. .............. 424/145.1 |

FOREIGN PATENT DOCUMENTS

| WO | WO 91/10741 | 7/1991 |
| WO | WO 92/01047 | 1/1992 |
| WO | WO 93/06213 | 4/1993 |
| WO | WO 94/02602 | 2/1994 |
| WO | WO 96/33735 | 10/1996 |

(Continued)

OTHER PUBLICATIONS

Pascalis et al. The Journal of Immunology (2002) 169, 3076-3084.*
Casset et al. (2003) BBRC 307, 198-205.*
Vajdos et al. (2002) J. Mol. Biol. 320, 415-428.*
Holm et al (2007) Mol. Immunol. 44: 1075-1084.*
Chen et al. J. Mol. Bio. (1999) 293, 865-881.*
Wu et al. J. Mol. Biol. (1999) 294, 151-162.*
Brummell et al. (Biochemistry 32:1180-1187 (1993)).*

(Continued)

*Primary Examiner*—Lynn Bristol
(74) *Attorney, Agent, or Firm*—Ropes & Gray LLP

(57) ABSTRACT

The present invention relates to antibodies including human antibodies and antigen-binding portions thereof that bind to myostatin, and that function to inhibit myostatin. The invention also relates to human anti-myostatin antibodies and antigen-binding portions thereof. The invention also relates to antibodies that are chimeric, bispecific, derivatized, single chain antibodies or portions of fusion proteins. The invention also relates to isolated heavy and light chain immunoglobulins derived from human anti-myostatin antibodies and nucleic acid molecules encoding such immunoglobulins. The present invention also relates to methods of making human anti-myostatin antibodies, compositions comprising these antibodies and methods of using the antibodies and compositions for diagnosis and treatment. The invention also provides gene therapy methods using nucleic acid molecules encoding the heavy and/or light immunoglobulin molecules that comprise the human anti-myostatin antibodies. The invention also relates to transgenic animals or plants comprising nucleic acid molecules of the present invention.

14 Claims, 21 Drawing Sheets

FOREIGN PATENT DOCUMENTS

| | | |
|---|---|---|
| WO | WO 96/34096 | 10/1996 |
| WO | WO 98/16654 | 4/1998 |
| WO | WO 98/24893 | 6/1998 |
| WO | WO 98/50433 | 11/1998 |
| WO | WO 98/52976 | 11/1998 |
| WO | WO 99/45031 | 9/1999 |
| WO | WO 99/53049 | 10/1999 |
| WO | WO 00/09560 | 2/2000 |
| WO | WO 00/34317 | 6/2000 |
| WO | WO 00/37504 | 6/2000 |
| WO | WO 2004/037861 | 5/2004 |
| WO | WO 2004/108157 | 12/2004 |
| WO | WO 2005/094446 | 10/2005 |

OTHER PUBLICATIONS

Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Bost et al. (Immunol. Invest. (1988) 17:577-586).*
Bendayan (J. Histochem. Cytochem. (1995) 43:881-886).*
Campbell et al, Biology, 5th ed. p. 856, 1999.*
Search output from ATCC website for query regarding: 1__116__1 (PTA-6566); 1__132__1 (PTA-6567); 1__136__3 (PTA-6568); 1__257__1 (PTA-6569); 1__268__1 (PTA-6570); 1__314__1 (PTA-6571); 1__46__1 (PTA-6572); 1__66__1 (PTA-6573); 2__112__1 (PTA-6574); 2__43__1 (PTA-6575); and 2__177__1 (PTA-6576), (Nov. 1, 2007).*
Fundamental Immunology 242 (William E. Paul, M.D. ed., 3d ed. 1993).*
MacCallum et al. (J. Mol. Biol. (1996) 262:732-745).*
Babcook, J.S. et al. "A novel strategy for generating monoclonal antibodies from single, isolated lymphocytes producing antibodies of defined specificities," Proc. Natl. Acad. Sci. USA 93:7843-48 (1996).
Bird et al., "Single-chain antigen-binding proteins," Science, 242:423-426 (1988).
Gonnet et al., "Exhaustive matching of the entire protein sequence database," Science, 256:1443-45 (1992).
Gonzalez-Cadavid et al., "Organization of the human myostatin gene and expression in healthy men and HIV-infected men with muscle wasting," Proc. Natl. Acad. Sci., 95 14938-4321 (1998).
Green et al., "Antigen-specific human monoclonal antibodies from mice engineered with human Ig heavy and light chain YACs," Nature Genetics, 7:13-21 (1994).
Green and Jakobovits, "Regulation of B cell development by variable gene complexity in mice reconstituted with human immunoglobulin yeast artificial chromosomes," Journal of Experimental Medicine, 188(3):483-495 (1998).
Griffiths et al., "Human anti-self antibodies with high specificity from phage display libraries," The EMBO Journal, 12(2):725-734 (1993).
Griffiths et al., "Isolation of high affinity human antibodies directly from large synthetic repertoires," The EMBO Journal, 13:3245-3260 (1994).
Hamrick et al., "Bone Architecture and Disc Degeneration in the Lumbar Spine of Mice Lacking GDF-8 (Myostatin)," J. Orthopaedic Res. 21:1025-1032 (2003).
Hill et al., "The myostatin propeptide and the follistatin-related gene are inhibitory binding proteins of myostatin in normal serum," J. Biol. Chem. 277:40735-40741 (2002).
Hill et al., "Regulation of myostatin in vivo by growth and differentiation factor-associated serum protein-1: a novel protein with protease inhibitor and follistatin domains," Mol. Endocrin 17(6): 1144-1154 (2003).
Holliger et al., "Diabodies: small bivalent and bispecific antibody fragments," Proc. Natl. Acad. Sci., 90:6444-6448 (1993).

Huston et al., "Protein engineering of antibody binding sites: Recovery of specific activity in an anti-digoxin single-chain Fv analogue produced in Escherichia coli," Proc. Natl. Acad. Sci., 85:5879-5883 (1988).
Ill et al., "Design and construction of a hybrid immunoglobulin domain with properties of both heavy and light chain variable regions," Protein Engineering, 10(8):949-957 (1997).
Kostelny et al., "Formation of a bispecific antibody by the use of leucine zippers," J. Immunol. 148:1547-1553 (1992).
LaPlanche et al., "Phosphorothioate-modified oligodeoxyribonucleotides, III. NMR and UV spectroscopic studies of the $R_p$-$R_p$, $S_p$-$S_p$, and $R_p$-$S_p$ duplexes, [d($GG_5AATTCC$)]$_2$, derived from diastereomeric O-ethyl phosphorothioates," Nucleic Acids Research, 14(22):9081-9093 (1986).
Li X et al., "Inhibition of Myostatin Increases Muscle Mass and Improves Glucose Sensitivity in Obese, Diabetic Mice," Poster #224 Keystone Symposia: Diabetes Mellitus: Molecular Mechanisms, Genetics and New Therapies (2002).
Marks et al., "Oligonucleotide primers for polymerase chain reaction amplification of human immunoglobulin variable genes and design of family-specific oligonucleotide probes." European Journal of Immunology, 21:985-991 (1991).
Martin et al., "The affinity-selection of a minibody polypeptide inhibitor of human interleukin-6," The EMBO Journal, 13(22): 5303-5309 (1994).
McCafferty et al., "Phage antibodies: filamentous phage displaying antibody variable domains," Nature, 348:552-554 (1990).
McPherron et al., "Suppression of body fat accumulation in myostatin-deficient mice," J. Clin. Inves. 109:595-601 (2002).
Mendez et al., "Functional transplant of megabase human immunoglobulin loci recapitulates human antibody response in mice," Nature Genetics, 15:146-156 (1997).
Nissim et al., "Antibody fragments from a 'single pot' phage display library as immunochemical reagents," The EMBO Journal vol. 13 No. 3 pp. 692-698 (1994).
Pearson, "Rapid and sensitive sequence comparison with FASTP and FASTA," Methods Enzymol. 183:63-98 (1990).
Pearson, "Effective protein sequence comparison," Methods Enzymol. 266:227-258 (1996).
Pearson, "Empirical statistical estimates for sequence similarity searches," J. Mol. Biol. 276:71-84 (1998).
Pearson, "Flexible Sequence Similarity Searching with the FASTA3 program package," Methods Mol Biol.132:185-219 (2000).
Schuelke et al., "Myostatin mutation associated with gross muscle hypertrophy in a child," New Engl. J. Med 350:2682-8 (2004).
Schulte, J. N. and Yarasheski, K. E., "Effects of resistance training on the rate of muscle protein synthesis in frail elderly people," In. J. Sport Nutr. Exerc. Metab 11 Suppl:S111-820 (2001).
Songsivilai & Lachmann, "Bispecific antibody: a tool for diagnosis and treatment of disease," Clin. Exp. Immunol. 79:315-321 (1990).
Stec et al., "Automated solid-phase synthesis, separation, and stereochemistry of phosphorothioate analogues of oligodeoxyribonucleotides," Journal of the American Chemical Society, 106(20):6077-6079 (1984).
Stein et al., "Physiochemical properties of phosphorothioate oligodeoxynucleotides," Nucleic Acids Research, 16(8):3209-3221 (1988).
Thies et al., "GDF-8 propeptide binds to GDF-8 and antagonizes biological activity by inhibiting GDF-8 receptor binding," Growth Factors 18:251-259 (2001).
Traunecker et al., "Bispecific single chain molecules (Janusins) target cytotoxic lymphocytes on HIV infected cells," The EMBO Journal, 10(12):3655-3659 (1991).
Traunecker et al., "Janusin: new molecular design for bispecific reagents," International Journal of Cancer, 7:51-52 (1992).
Uhlmann et al., "Antisense oligonucleotides: a new therapeutic principle," Chemical Reviews, 90(4):543-584 (1990).
Walker, K. S. et al., "Resistance Training Alters Plasma Myostatin but not IGF-1 in Healthy Men," Med Sci Sports Exerc. 36(5):787-93 (2004).
Yarasheski K. E. et al., "Serum myostatin-immunoreactive protein is increased in 60-92 year old women and men with muscle wasting," J. Nutr. Health Aging 6(5):343-8 (2002).

Zawel et al., "Human Smad3 and Smad4 are sequence-specific transcription activators," *Mol. Cell* 1:611-617 (1998).

Zon et al., "Phosphorothioate oligonucleotides," *Oligonucleotides and Analogues: A Practical Approach*, 87-108 (F. Eckstein, Ed., Oxford University Press, Oxford England (1991).

Zon et al., "Phosphorothioate oligonucleotides: chemistry, purification, analysis, scale-up and future directions," *Anti-Cancer Drug Design*, 6:539-568 (1991).

* cited by examiner

FIG. 7

| Peptide Number | Amino acid Sequence | SEQ ID NO. |
|---|---|---|
| 1 | DFGLDCDEHSTESRCCRY | 103 |
| 2 | PLTVDFEAFGWDWIIAPK | 104 |
| 3 | RYKANYCSGECEFVFLQK | 105 |
| 4 | YPHTHLVHQANPRGSAGP | 106 |
| 5 | CCTPTKMSPINMLYFNGK | 107 |
| 6 | EQIIYGKIPAMVVDRCGCS | 108 |
| 7 | HSTESRCCRYPLTVDFEA | 109 |
| 8 | FGWDWIIAPKRYKANYCS | 110 |
| 9 | GECEFVFLQKYPHTHLVH | 111 |
| 10 | QANPRGSAGPCCTPTKMS | 112 |
| 11 | PINMLYFNGKEQIIYGKI | 113 |

GDF-8   DFGLDCDEHSTESRCCRYPLTVDFEAFGWDWIIAPKRYKANYCSGECEFVFLQKYPHTHL 60   SEQ ID NO:89
GDF-11  NLGLDCDEHSSESRCCRYPLTVDFEAFGWDWIIAPKRYKANYCSGQCEYMFMQKYPHTHL 60   SEQ ID NO:90
        ::**********************************::*:::********

GDF-8   VHQANPRGSAGPCCTPTKMSPINMLYFNGKEQIIYGKIPAMVVDRCGCS 109
GDF-11  VQQANPRGSAGPCCTPTKMSPINMLYFNDKQQIIYGKIPGMVVDRCGCS 109
        *:************************::****.******

FIG. 12

| Clone | A204 IC50 (nM) | L6 IC50 (nM) | BIAcore KD (pM) | GDF11 activity (A204) | VH | D | JH | VK | JK |
|---|---|---|---|---|---|---|---|---|---|
| 1_116_1 | 0.83 | 1.3 | 12 | 60% inhibition at 2uM, IC50>=0.7uM | 3-21 | 5-5 | JH4B | A30 | JK1 |
| 1_132_1 | 1.8 | 1.7 |  | IC50=2.8nM | 1-02 | 4-23 | JH6B | A3 | JK4 |
| 1_46_1 | 3.1 | 8.3 | 99 | IC50=7nM | 1-02 | 4-23 | JH6B | A3 | JK4 |
| 1_257_1 | 9.3 | 7.7 | 160.0 | 50% inhibition at 4uM IC50~4uM | 3-21 | 5-12 | JH6B | A30 | JK3 |
| 2_112_1 | 12.3 | 11.4 | 11 | 30% inhibition at 1.3uM IC50>1.3uM | 3-23 | 1-7 | JH3B | L2 | JK4 |
| 2_43_1 | 13.9 | 16.9 | 1500 | No inhibition at 0.7uM | 3-23 | 1-7 | JH3B | L2 | JK4 |
| 1_136_3 | 14 | 6.6 | 43.0 | No inhibition at 0.2uM | 3-21 | 5-5 | JH4B | A30 | JK1 |
| 1_268_1 | 19 | 37 | 240 | No inhibition at 2uM | 3-21 | 1-26 | JH4B | A30 | JK4 |
| 1_314_1 | 28.5 | 9.6 | 110.0 | No inhibition at 2uM | 3.21 |  | JH6B | A30 | JK1 |
| 1_66_1 | 35.1 | 41.9 | 83 | 40% inhibition at 2uM IC50~2uM | 3-21 | 5-5 | JH4B | A30 | JK3 |
| 2_177_1 | 40 | 223 | 890 | No inhibition at 2uM | 3-23 | 1-7 | JH3B | L2 | JK4 |

FIG. 13

| mAB | VH | D | JH | VK | JK | 1.116.1 bin | 1.136.3 bin | 1.257.1 bin | 1.314.1 bin | 1.66.1 bin | 1.46.1 bin | 1.132.1 bin | 1.268.1 bin | 2.43.1 bin | 2.112.1 bin | 2.177.1 bin | Peptide 1 | 2 | 3 | 4 | 5 | 6 | 7 | 8 | 9 | 10 | 11 |
|---|---|---|---|---|---|---|---|---|---|---|---|---|---|---|---|---|---|---|---|---|---|---|---|---|---|---|---|
| 1-116-1 | 3-21 | 5-5 | JH4B | A30 | JK1 | yes | yes | yes | yes | yes | yes | yes | yes | yes | no | no | | | | | | | | | | | |
| 1-136-3 | 3-21 | 5-5 | JH4B | A30 | JK1 | yes | yes | yes | yes | yes | yes | yes | yes | no | no | no | | yes | | | | | | | | | |
| 1-257-1 | 3-21 | 5-12 | JH6B | A30 | JK3 | yes | yes | yes | yes | yes | yes | yes | yes | no | no | no | | yes | | | | | | | | | |
| 1-314-1 | 3-21 | | JH6B | A30 | JK1 | yes | yes | yes | yes | yes | yes | yes | yes | no | no | no | | yes | | | | | | | | | |
| 2-112-1 | 3-23 | 1-7 | JH3B | L2 | JK4 | no | no | no | no | no | no | no | no | yes | yes | yes | yes | | | | | | | | | | |
| 2-177-1 | 3-23 | 1-7 | JH3B | L2 | JK4 | no | no | no | no | no | no | no | no | no | yes | yes | yes | | | | yes | | | | | | |
| 2-43-1 | 3-23 | 1-7 | JH3B | L2 | JK4 | yes | no | no | no | no | no | no | no | yes | yes | yes | yes | | | | yes | | | | | | |
| 1-46-1 | 1-02 | 4-23 | JH6B | A3 | JK4 | yes | yes | yes | yes | yes | yes | yes | yes | no | no | no | | | | | yes | | | | | | |
| 1-66-1 | 3-21 | 5-5 | JH4B | A30 | JK3 | yes | yes | yes | yes | yes | yes | yes | yes | no | no | no | | | | | | | | | | | |
| 1-132-1 | | | | | | yes | yes | yes | yes | yes | no | yes | yes | no | no | no | | | | | | | | | | | |
| 1-268-1 | 3-21 | 1-26 | JH4B | A30 | JK4 | yes | yes | yes | yes | yes | yes | yes | yes | no | no | no | | | | | | | | | | | |

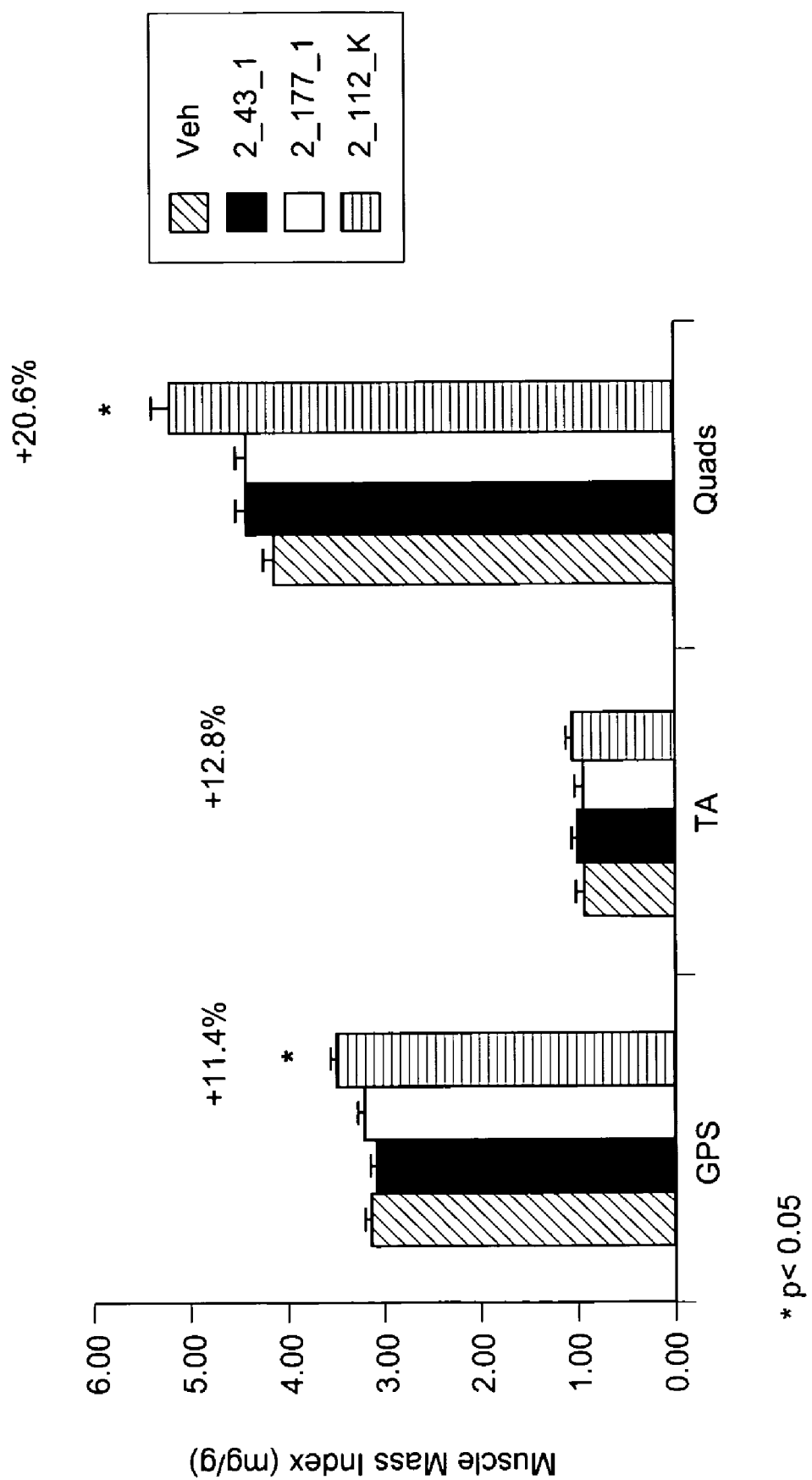

Skeletal Muscle Weight

Tibialis Muscle Strengh

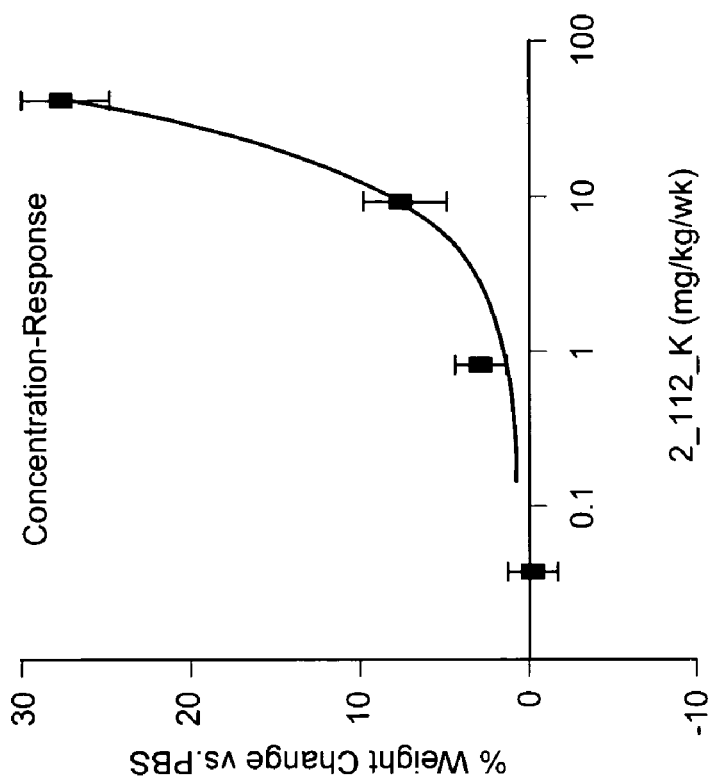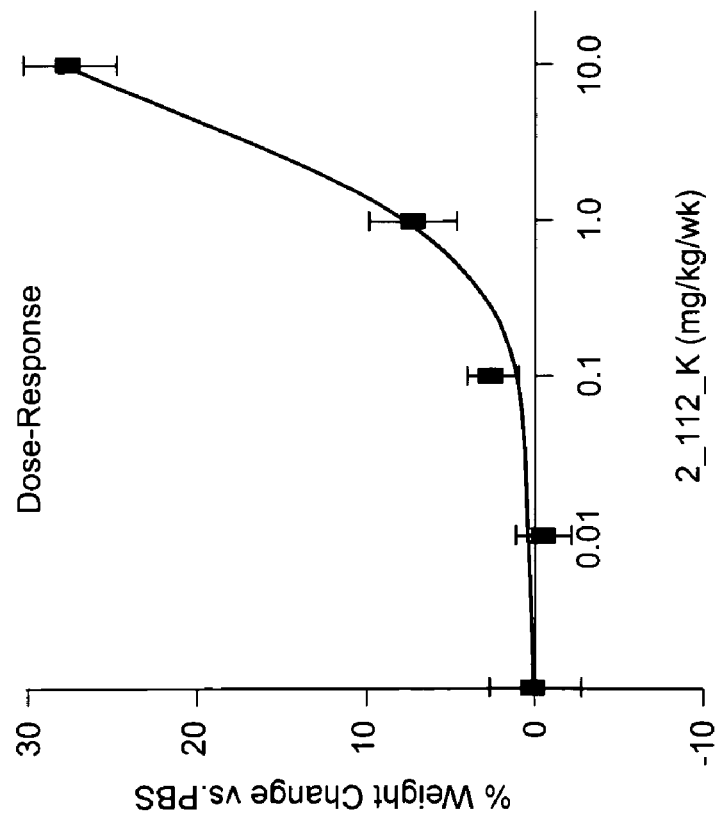

FIG. 19A

```
ANTIBODY2_112_1    EVQLLESGGGLIQPGGSLRLSCAASGFTFSSFAMSWVRQAPGKGLEWVSTISGSGGYTFY   60
ANTIBODY2_112_K    EVQLLESGGGLVQPGGSLRLSCAASGFTFSSFAMSWVRQAPGKGLEWVSTISGSGGYTFY   60
                   ***********:************************************************

ANTIBODY2_112_1    ADSVKGRFTISRDNSKNTLYLQMNSLRAEDTAVYYCAKDGRYNWNYGAFDIWGQGTMVTV  120
ANTIBODY2_112_K    ADSVKGRFTISRDNSKNTLYLQMNSLRAEDTAVYYCAKDGRYNWNYGAFDIWGQGTMVTV  120
                   ************************************************************

ANTIBODY2_112.1    SS  122    SEQ ID NO:77
ANTIBODY2_112_K    SS  122    SEQ ID NO:118
                   **
```

FIG. 19B

```
ANTIBODY2_112_1    EIVMTQSPATLSVSPGERATLSCRASQSVSSNLAWYQQKPGQAPRLLIYGASTRATGFPA   60
ANTIBODY2_112_K    EIVMTQSPATLSVSPGERATLSCRASQSVSSNLAWYQQKPGQAPRLLIYGASTRATGIPA   60
                   *********************************************************:**

ANTIBODY2_112_1    RFSGSGSGTEFTLTISSLQSEDFAIYYCQQYNNWPLTFGGGTKVEIK  107   SEQ ID NO:79
ANTIBODY2_112_K    RFSGSGSGTEFTLTISSLQSEDFAVYYCQQYNNWPLTFGGGTKVEIK  107   SEQ ID NO:120
                   ***********************:***********************
```

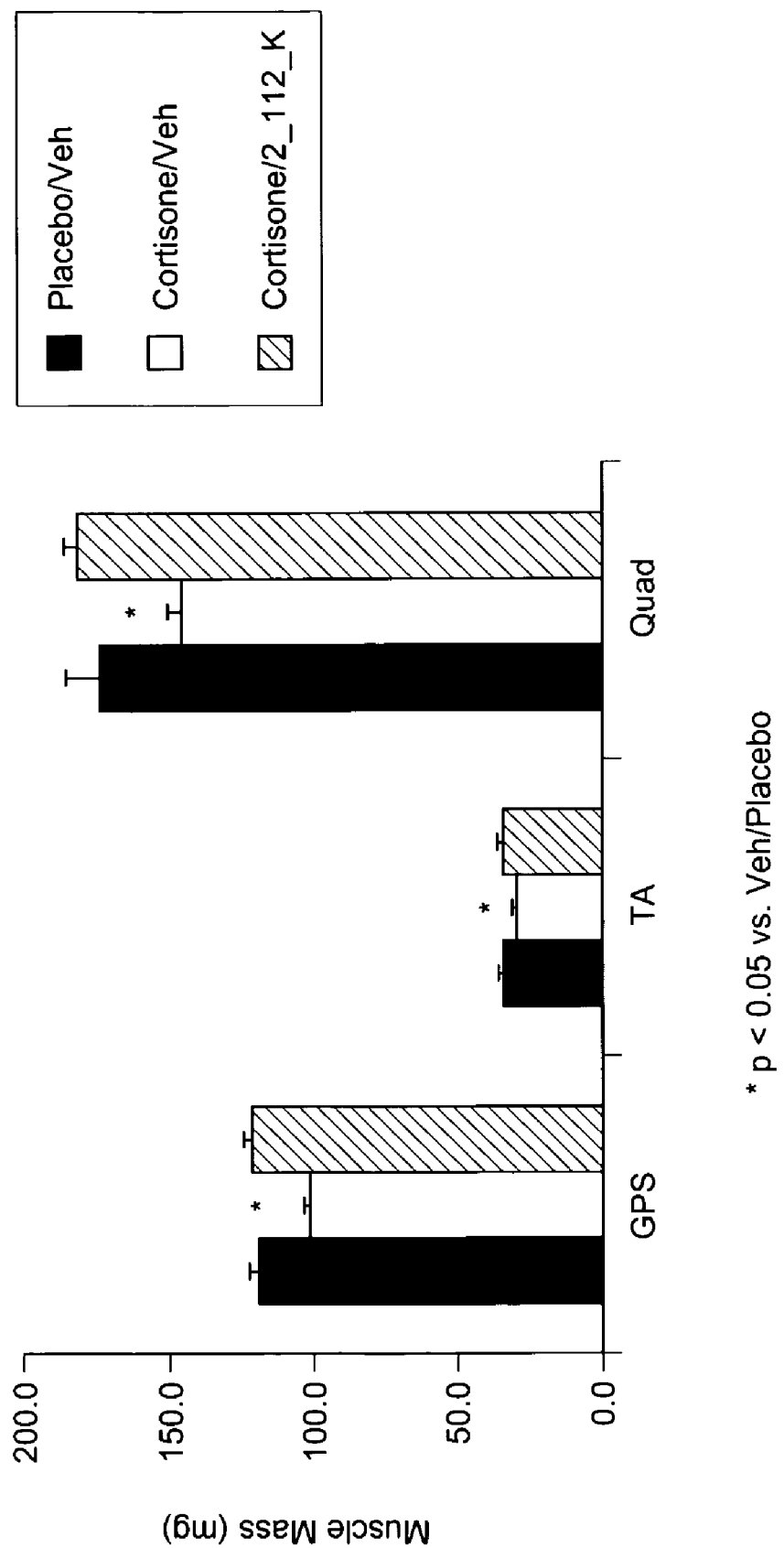

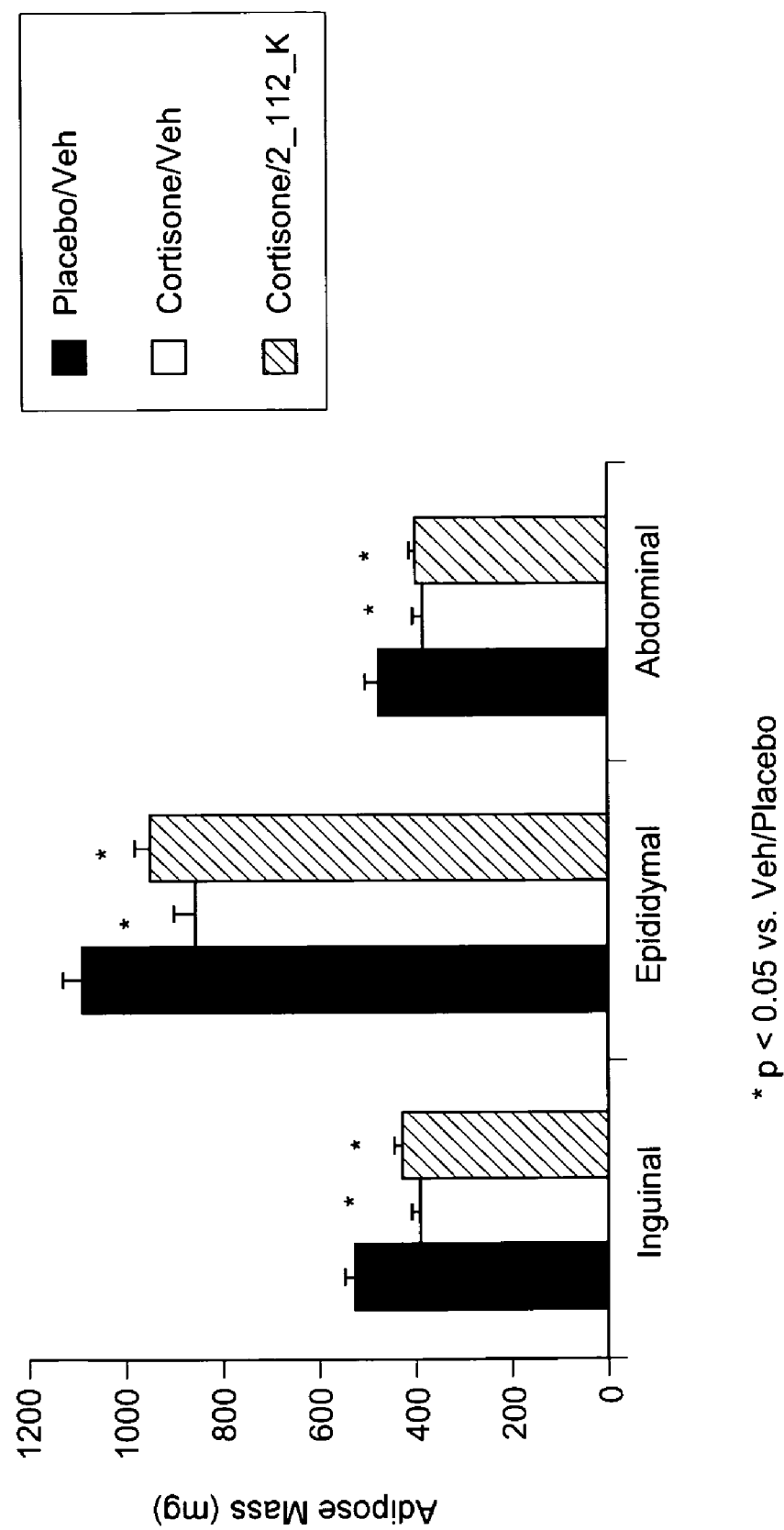

SEQUENCE LISTING

<160> NUMBER OF SEQ ID NOS: 122

<210> SEQ ID NO 1
<211> LENGTH: 1338
<212> TYPE: DNA
<213> ORGANISM: Homo sapiens -continued

```
<400> SEQUENCE: 1
gaggtgcagc tggtggagtc tgggggaggc ctggtcaagc ctgggggtc cctgagactc      60 tcctgtgcag cctctggatt caccttcagt agctatagca tgaattgggt ccgccaggct     120
ccagggaagg gctggagtg gtctcatcc attagtagta gtagtagtta catatactac       180
gcagactcag tgaagggccg attcaccatc tccagagaca acgccaagaa ctcactgtat     240
ctgcaaatga acagcctgag agccgaggac acggctgtgt attactgtgc gagagatcgg    300
gggtacagct atggtcttga ctactggggc cagggaaccc tggtcaccgt ctcctcagcc    360
tccaccaagg gcccatcggt cttccccctg gcgccctgct ccaggagcac ctccgagagc    420
acagcggccc tgggctgcct ggtcaaggac tacttccccg aaccggtgac ggtgtcgtgg    480
aactcaggcg ctctgaccag cggcgtgcac accttcccag ctgtcctaca gtcctcagga    540
ctctactccc tcagcagcgt ggtgaccgtg ccctccagca acttcggcac ccagacctac    600
acctgcaacg tagatcacaa gcccagcaac accaaggtgg acaagacagt tgagcgcaaa    660
tgttgtgtcg agtgcccacc gtgcccagca ccacctgtgg caggaccgtc agtcttcctc    720
ttccccccaa aacccaagga cacctctcatg atctcccgga cccctgaggt cacgtgcgtg    780
gtggtggacg tgagccacga agaccccgag gtccagttca actggtacgt ggacggcgtg    840
gaggtgcata atgccaagac aaagccacgg gaggagcagt tcaacagcac gttccgtgtg    900
gtcagcgtcc tcaccgttgt gcaccaggac tggctgaacg gcaaggagta caagtgcaag    960
gtctccaaca aaggcctccc agcccccatc gagaaaacca tctccaaaac caaagggcag   1020
ccccgagaac cacaggtgta caccctgccc ccatcccggg aggagatgac caagaaccag   1080
gtcagcctga cctgcctggt caaaggcttc taccccagcg acatcgccgt ggagtgggag   1140
agcaatgggc agccggagaa caactacaag accacacctc ccatgctgga ctccgacggc   1200
tccttcttcc tctacagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gtaaatga                                                  1338

<210> SEQ ID NO 2
<211> LENGTH: 445
<212> TYPE: PRT
<213> ORGANISM: Homo sapiens

<400> SEQUENCE: 2

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
         35                  40                  45

Ser Ser Ile Ser Ser Ser Ser Tyr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Gly Tyr Ser Tyr Gly Leu Asp Tyr Trp Gly Gln Gly
            100                 105                 110

Thr Leu Val Thr Val Ser Ser Ala Ser Thr Lys Gly Pro Ser Val Phe
        115                 120                 125
```

```
Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 3
<211> LENGTH: 645
<212> TYPE: DNA
<213> ORGANISM: Homo sapiens

<400> SEQUENCE: 3

```
gacatccaga tgacccagtc tccatcctcc ctgtctgcat ctgtaggaga cagagtcacc    60
atcacttgcc gggcaagtca gggcattaga aatgctttag ctggtatca gcagaaacca    120 gggaaagccc ctcagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt accctcggac gttcggccaa    300
gggaccaagg tggaaatcaa acgaactgtg gctgcaccat ctgtcttcat cttcccgcca    360
```

```
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gttag                     645
```

```
<210> SEQ ID NO 4
<211> LENGTH: 214
<212> TYPE: PRT
<213> ORGANISM: Homo sapiens

<400> SEQUENCE: 4
```

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Ala
             20                  25                  30

Leu Gly Trp Tyr Gln Gln Lys Pro Gly Lys Ala Pro Gln Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 5
<211> LENGTH: 1350
<212> TYPE: DNA
<213> ORGANISM: Homo sapiens

<400> SEQUENCE: 5
```

```
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccta acaatggtgg cacaaactat      180
gcacagaagt tcagggcag ggtcaccatg accagggaca cgtccatcag cacagcctac     240
atggagctga gcaggctgag atctgacgac acggccgtgt atcactgtgc gagaaatacg     300
gtgggaagtg ggtactacta ctacggtatg gacgtctggg gccaagggac cacggtcacc     360
```

```
gtctcctcag cctccaccaa gggcccatcg tcttccccc  tggcgccctg ctccaggagc    420
acctccgaga gcacagcggc cctgggctgc ctggtcaagg actacttccc cgaaccggtg    480
acggtgtcgt ggaactcagg cgctctgacc agcggcgtgc acaccttccc agctgtccta    540
cagtcctcag gactctactc cctcagcagc gtggtgaccg tgccctccag caacttcggc    600
acccagacct acacctgcaa cgtagatcac aagcccagca caccaaggt ggacaagaca     660
gttgagcgca aatgttgtgt cgagtgccca ccgtgcccag caccacctgt ggcaggaccg    720
tcagtcttcc tcttcccccc aaaacccaag gacaccctca tgatctcccg gaccctgag    780
gtcacgtgcg tggtggtgga cgtgagccac gaagaccccg aggtccagtt caactggtac    840
gtggacggcg tggaggtgca taatgccaag acaaagccac gggaggagca gttcaacagc    900
acgttccgtg tggtcagcgt cctcaccgtt gtgcaccagg actggctgaa cggcaaggag    960
tacaagtgca aggtctccaa caaaggcctc ccagccccca tcgagaaaac catctccaaa   1020
accaaagggc agccccgaga accacaggtg tacaccctgc ccccatcccg ggaggagatg   1080
accaagaacc aggtcagcct gacctgcctg gtcaaaggct tctaccccag cgacatcgcc   1140
gtggagtggg agagcaatgg gcagccggag aacaactaca agaccacacc tcccatgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaatga                                    1350

<210> SEQ ID NO 6
<211> LENGTH: 449
<212> TYPE: PRT
<213> ORGANISM: Homo sapiens

<400> SEQUENCE: 6

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Ile Asn Pro Asn Asn Gly Gly Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr His Cys
             85                  90                  95

Ala Arg Asn Thr Val Gly Ser Gly Tyr Tyr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190
```

```
Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Gln Phe Asn Trp Tyr Val Asp Gly Val Glu Val His Asn
    275                 280                 285

Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
            325                 330                 335

Thr Ile Ser Lys Thr Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys
```

<210> SEQ ID NO 7
<211> LENGTH: 660
<212> TYPE: DNA
<213> ORGANISM: Homo sapiens

<400> SEQUENCE: 7

```
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agtcaggcca gtctccacag ctcctgatcc atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagttct acaaactccg   300
ctcactttcg gcggagggac caaggtggag atcaaacgaa ctgtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660
```

<210> SEQ ID NO 8
<211> LENGTH: 219
<212> TYPE: PRT
<213> ORGANISM: Homo sapiens

<400> SEQUENCE: 8

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ser Gly Gln Ser
        35                  40                  45

Pro Gln Leu Leu Ile His Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 9
<211> LENGTH: 1338
<212> TYPE: DNA
<213> ORGANISM: Homo sapiens

<400> SEQUENCE: 9
gaggtgcagc tggtggagtc tgggggaggc ctggtcaagc ctgggggtc cctgagactc      60 tcctgtgcag cctctggatt caccttcagt agctatagca tgaactgggt ccgccaggct    120
ccagggaagg ggctggagtg ggtctcatcc attagtagta gtagtagtta catatactac    180
gcagactcag tgaagggccg attcaccatc tccagagaca acgccaagaa ctcactgtat    240
ctgcaaatga acagcctgag agccgaggac acggctgtgt attactgtgc gagagatcgt    300
ggatacagct atggtattga ctactggggc cagggaaccc tggtcaccgt ctcctcagcc    360
tccaccaagg gcccatcggt cttccccctg gcgccctgct ccaggagcac ctccgagagc    420
acagcggccc tgggctgcct ggtcaaggac tacttccccg aaccggtgac ggtgtcgtgg    480
aactcaggcg ctctgaccag cggcgtgcac accttcccag ctgtcctaca gtcctcagga    540
ctctactccc tcagcagcgt ggtgaccgtg ccctccagca acttcggcac ccagacctac    600
acctgcaacg tagatcacaa gcccagcaac accaaggtgg acaagacagt tgagcgcaaa    660

-continued

```
tgttgtgtcg agtgcccacc gtgcccagca ccacctgtgg caggaccgtc agtcttcctc    720
ttccccccaa acccaagga caccctcatg atctcccgga cccctgaggt cacgtgcgtg    780
gtggtggacg tgagccacga agaccccgag gtccagttca actggtacgt ggacggcgtg    840
gaggtgcata atgccaagac aaagccacgg gaggagcagt tcaacagcac gttccgtgtg    900
gtcagcgtcc tcaccgttgt gcaccaggac tggctgaacg gcaaggagta caagtgcaag    960
gtctccaaca aaggcctccc agcccccatc gagaaaacca tctccaaaac caaagggcag   1020
ccccgagaac cacaggtgta caccctgccc ccatcccggg aggagatgac caagaaccag   1080
gtcagcctga cctgcctggt caaaggcttc taccccagcg acatcgccgt ggagtgggag   1140
agcaatgggc agccggagaa caactacaag accacacctc ccatgctgga ctccgacggc   1200
tccttcttcc tctacagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gtaaatga                                                 1338
```

<210> SEQ ID NO 10
<211> LENGTH: 445
<212> TYPE: PRT
<213> ORGANISM: Homo sapiens

<400> SEQUENCE: 10

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Tyr Ser Tyr Gly Ile Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255
```

```
Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
            290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 11
<211> LENGTH: 645
<212> TYPE: DNA
<213> ORGANISM: Homo sapiens

<400> SEQUENCE: 11
gacatccaga tgacccagtc tccatcctcc ctgtctgcat ctgtaggaga cagagtcacc      60
atcacttgcc gggcaagtca gggcattaga aatgctttag ctggtatca gcagaaacca     120 gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataatagtt accctcggac gttcggccaa     300
gggaccaagg tggaaatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                    645

<210> SEQ ID NO 12
<211> LENGTH: 214
<212> TYPE: PRT
<213> ORGANISM: Homo sapiens

<400> SEQUENCE: 12

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Ala
            20                  25                  30
```

```
Leu Gly Trp Tyr Gln Gln Lys Pro Gly Lys Ala Pro Lys Arg Leu Ile
         35                  40                  45
Tyr Ala Ala Ser Ser Leu Gln Ser Gly Val Pro Ser Arg Phe Ser Gly
     50                  55                  60
Ser Gly Ser Gly Thr Glu Phe Thr Leu Thr Ile Ser Ser Leu Gln Pro
 65                  70                  75                  80
Glu Asp Phe Ala Thr Tyr Tyr Cys Leu Gln His Asn Ser Tyr Pro Arg
                 85                  90                  95
Thr Phe Gly Gln Gly Thr Lys Val Glu Ile Lys Arg Thr Val Ala Ala
             100                 105                 110
Pro Ser Val Phe Ile Phe Pro Pro Ser Asp Glu Gln Leu Lys Ser Gly
         115                 120                 125
Thr Ala Ser Val Val Cys Leu Leu Asn Asn Phe Tyr Pro Arg Glu Ala
     130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 13
<211> LENGTH: 1338
<212> TYPE: DNA
<213> ORGANISM: Homo sapiens

<400> SEQUENCE: 13
gaggtgcagc tggtggagtc tgggggaggc ctggtcaagc ctggggggtc cctgagactc      60
tcctgtgcag cctctggatt caccttcagt agctatagca tgaactgggt ccgccaggct     120
ccagggaagg ggctggagtg gtctcatcc attagtagta gtagtagtta catatactac     180
gcagactcag tgaagggccg attcaccatc tccagagaca acgccaagaa ctcactgtat     240
ctgcaaatga acagcctgag agccgaggac acggctgtgt attactgtgc gagagatagg     300
ggatactact acggtatgga cgtctggggc caagggacca cggtcaccgt ctcctcagcc     360
tccaccaagg gcccatcggt cttccccctg gcgccctgct ccaggagcac ctccgagagc     420
acagcggccc tgggctgcct ggtcaaggac tacttccccg aaccggtgac ggtgtcgtgg     480
aactcaggcg ctctgaccag cggcgtgcac accttcccag ctgtcctaca gtcctcagga     540
ctctactccc tcagcagcgt ggtgaccgtg ccctccagca acttcggcac ccagacctac     600
acctgcaacg tagatcacaa gcccagcaac accaaggtgg acaagacagt tgagcgcaaa     660
tgttgtgtcg agtgcccacc gtgcccagca ccacctgtgg caggaccgtc agtcttcctc     720
ttccccccaa aacccaagga caccctcatg atctcccgga cccctgaggt cacgtgcgtg     780
gtggtggacg tgagccacga agaccccgag gtccagttca actggtacgt ggacggcgtg     840
gaggtgcata atgccaagac aaagccacgg gaggagcagt tcaacagcac gttccgtgtg     900
gtcagcgtcc tcaccgttgt gcaccaggac tggctgaacg gcaaggagta caagtgcaag     960
gtctccaaca aaggcctccc agcccccatc gagaaaacca tctccaaaac caaagggcag    1020
ccccgagaac cacaggtgta caccctgccc ccatcccggg aggagatgac caagaaccag    1080
```

```
gtcagcctga cctgcctggt caaaggcttc tacccccagcg acatcgccgt ggagtgggag   1140
agcaatgggc agccggagaa caactacaag accacacctc ccatgctgga ctccgacggc   1200
tccttcttcc tctacagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gtaaatga                                                 1338
```

<210> SEQ ID NO 14
<211> LENGTH: 445
<212> TYPE: PRT
<213> ORGANISM: Homo sapiens

<400> SEQUENCE: 14

```
Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
         35                  40                  45

Ser Ser Ile Ser Ser Ser Ser Tyr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Gly Tyr Tyr Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320
```

```
Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 15
<211> LENGTH: 645
<212> TYPE: DNA
<213> ORGANISM: Homo sapiens

<400> SEQUENCE: 15
gacatccaga tgacccagtc tccatcctcc ctgtctgcat ctgtaggaga cagagtcacc      60
ctcacttgcc gggcaagtca gggcattaga aatgctttag ctggtatcag cagaaaacca    120
gggaaagccc ctaagcgcct gatctatggt gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccattcac tttcggccct    300
gggaccaaag tggatatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccTgacg    540
ctgagcaaag cagactacga gaaacacaaa gtctacgcct gcgaagtcac ccatcagggc    600
ctgagctcgc ccgtcacaaa gagcttcaac aggggagagt gttag                    645

<210> SEQ ID NO 16
<211> LENGTH: 214
<212> TYPE: PRT
<213> ORGANISM: Homo sapiens

<400> SEQUENCE: 16

Asp Ile Gln Met Thr Gln Ser Pro Ser Ser Leu Ser Ala Ser Val Gly
1               5                   10                  15

Asp Arg Val Thr Leu Thr Cys Arg Ala Ser Gln Gly Ile Arg Asn Ala
            20                  25                  30

Leu Gly Trp Tyr Gln Gln Lys Pro Gly Lys Ala Pro Lys Arg Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Phe
                85                  90                  95
```

```
Thr Phe Gly Pro Gly Thr Lys Val Asp Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 17
<211> LENGTH: 1338
<212> TYPE: DNA
<213> ORGANISM: Homo sapiens

<400> SEQUENCE: 17
gaggtgcagc tggtggagtc tgggggaggc ctggtcaagc ctgggggtc cctgagactc      60
tcctgtgcag cctctggatt caccttcagt agctatagca tgaactgggt ccgccaggct    120
ccagggaagg ggctggagtg ggtctcatcc attagtagta gtagtagtta catatactac    180
gcagactcag tgaagggccg attcaccatc tccagagaca acgccaagaa ctcactgtat    240
ctgcaaatga acagcctgag agccgaggac acgactgtgt attactgtgc gagagatcga    300
ggctacctct acggtatgga cgtctgggc caagggacca cggtcaccgt ctcctcagcc    360
tccaccaagg gcccatcggt cttccccctg gcgccctgct ccaggagcac ctccgagagc    420
acagcggccc tgggctgcct ggtcaaggac tacttccccg aaccggtgac ggtgtcgtgg    480
aactcaggcg ctctgaccag cggcgtgcac accttcccag ctgtcctaca gtcctcagga    540
ctctactccc tcagcagcgt ggtgaccgtg ccctccagca acttcggcac ccagacctac    600
acctgcaacg tagatcacaa gcccagcaac accaaggtgg acaagacagt tgagcgcaaa    660
tgttgtgtcg agtgcccacc gtgcccagca ccacctgtgg caggaccgtc agtcttcctc    720
ttccccccaa aacccaagga caccctcatg atctcccgga cccctgaggt cacgtgcgtg    780
gtggtggacg tgagccacga agaccccgag gtccagttca actggtacgt ggacggcgtg    840
gaggtgcata atgccaagac aaagccacgg gaggagcagt tcaacagcac gttccgtgtg    900
gtcagcgtcc tcaccgttgt gcaccaggac tggctgaacg gcaaggagta caagtgcaag    960
gtctccaaca aaggcctccc agcccccatc gagaaaacca tctccaaaac caagggcag   1020
ccccgagaac acaggtgta caccctgccc ccatcccggg aggagatgac caagaaccag   1080
gtcagcctga cctgcctggt caaaggcttc taccccagcg acatcgccgt ggagtgggag   1140
agcaatgggc agccggagaa caactacaag accacacctc ccatgctgga ctccgacggc   1200
tccttcttcc tctacagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gtaaatga                                                 1338
```

<210> SEQ ID NO 18
<211> LENGTH: 445
<212> TYPE: PRT
<213> ORGANISM: Homo sapiens

<400> SEQUENCE: 18

```
Glu Val Gln Leu Val Glu Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Thr Val Tyr Tyr Cys
                85                  90                  95

Ala Arg Asp Arg Gly Tyr Leu Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380
```

```
Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 19
<211> LENGTH: 645
<212> TYPE: DNA
<213> ORGANISM: Homo sapiens

<400> SEQUENCE: 19
gacatccaga tgacccagtc tccatcctcc ctgtctgcat ctgtaggaga cagagtcacc      60
atcacttgcc gggcaagtca ggccattaga aatgatttag ctggtatca gcagaaacca     120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt accctcggac gttcggccaa    300
gggaccaagg tggaaatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645

<210> SEQ ID NO 20
<211> LENGTH: 214
<212> TYPE: PRT
<213> ORGANISM: Homo sapiens

<400> SEQUENCE: 20

Asp Ile Gln Met Thr Gln Ser Pro Ser Leu Ser Ala Ser Val Gly
1               5                   10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
              165                 170                 175

Ser Thr Leu Thr Leu Ser Lys Ala Asp Tyr Glu Lys His Lys Val Tyr
          180                 185                 190

Ala Cys Glu Val Thr His Gln Gly Leu Ser Ser Pro Val Thr Lys Ser
      195                 200                 205

Phe Asn Arg Gly Glu Cys
    210

<210> SEQ ID NO 21
<211> LENGTH: 1350
<212> TYPE: DNA
<213> ORGANISM: Homo sapiens

<400> SEQUENCE: 21
caggtgcagc tggtgcagtc tggggctgag gtgaagaagc ctggggcctc agtgaaggtc      60
tcctgcaagg cttctggata taccttcacc ggctactata tgcactgggt gcgacaggcc    120
cctggacaag gcttgagtg gatgggatgg atcaaccta acagtggtgg cacaaactat      180
gcacagaagt tcagggcag gtcaccatg accaggaca cgtccatcag cacagcctac        240
ctggagctga gcaggctgag atctgacgac acggccgtgt attactgtgc gagaaatacg    300
gtgggaactg gatactacta ctacggtatg gacgtctggg gccaagggac cacggtcacc    360
gtctcctcag cctccaccaa gggcccatcg gtcttccccc tggcgccctg ctccaggagc    420
acctccgaga gcacagcggc cctgggctgc ctggtcaagg actacttccc cgaaccggtg    480
acggtgtcgt ggaactcagg cgctctgacc agcggcgtgc acaccttccc agctgtccta    540
cagtcctcag gactctactc cctcagcagc gtggtgaccg tgccctccag caacttcggc    600
acccagacct acacctgcaa cgtagatcac aagcccagca caccaaggt ggacaagaca     660
gttgagcgca aatgttgtgt cgagtgccca ccgtgcccag caccacctgt ggcaggaccg    720
tcagtcttcc tcttcccccc aaaacccaag gacaccctca tgatctcccg gacccctgag    780
gtcacgtgcg tggtggtgga cgtgagccac gaagaccccg aggtccagtt caactggtac    840
gtggacggcg tggaggtgca taatgccaag acaaagccac gggaggagca gttcaacagc    900
acgttccgtg tggtcagcgt cctcaccgtt gtgcaccagg actggctgaa cggcaaggag    960
tacaagtgca aggtctccaa caaaggcctc ccagccccca tcgagaaaac catctccaaa   1020
accaaagggc agccccgaga accacaggtg tacaccctgc ccccatcccg ggaggagatg   1080
accaagaacc aggtcagcct gacctgcctg gtcaaaggct tctaccccag cgacatcgcc   1140
gtggagtggg agagcaatgg gcagccggag aacaactaca agaccacacc tcccatgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaatga                                    1350

<210> SEQ ID NO 22
<211> LENGTH: 449
<212> TYPE: PRT
<213> ORGANISM: Homo sapiens

<400> SEQUENCE: 22

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
             20                  25                  30

-continued

```
Tyr Met His Trp Val Arg Gln Ala Pro Gly Gln Gly Leu Glu Trp Met
     35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Leu Glu Leu Ser Arg Leu Arg Ser Asp Asp Thr Ala Val Tyr Tyr Cys
                 85                  90                  95

Ala Arg Asn Thr Val Gly Thr Gly Tyr Tyr Tyr Gly Met Asp Val
                100                 105                 110

Trp Gly Gln Gly Thr Thr Val Thr Val Ser Ser Ala Ser Thr Lys Gly
            115                 120                 125

Pro Ser Val Phe Pro Leu Ala Pro Cys Ser Arg Ser Thr Ser Glu Ser
            130                 135                 140

Thr Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Asn Phe Gly Thr Gln Thr Tyr Thr Cys Asn Val
            195                 200                 205

Asp His Lys Pro Ser Asn Thr Lys Val Asp Lys Thr Val Glu Arg Lys
210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Phe Arg Val
        290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

```
Ala Leu His Asn His Tyr Thr Gln Lys Ser Leu Ser Leu Ser Pro Gly
        435                 440                 445

Lys

<210> SEQ ID NO 23
<211> LENGTH: 660
<212> TYPE: DNA
<213> ORGANISM: Homo sapiens

<400> SEQUENCE: 23
gatattgtga tgactcagtc tccactctcc ctgcccgtca cccctggaga gccggcctcc      60
atctcctgca ggtctagtca gagcctcctg catagtaatg gatacaacta tttggattgg    120
tacctgcaga agccagggca gtctccacag gtcctgatct atttggtttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactcct    300
cccactttcg gcggagggac caaggtggag atcaaacgaa ctgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttag    660

<210> SEQ ID NO 24
<211> LENGTH: 219
<212> TYPE: PRT
<213> ORGANISM: Homo sapiens

<400> SEQUENCE: 24

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Val Leu Ile Tyr Leu Val Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Pro Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 25
<211> LENGTH: 1350
<212> TYPE: DNA
<213> ORGANISM: Homo sapiens

<400> SEQUENCE: 25

| | | | | | |
|---|---|---|---|---|---|
| gaggtgcagc | tattggagtc | tgggggaggc | ttgatacagc | ctggggggtc | cctgagactc | 60 |
| tcctgtgcag | cctctggatt | cacctttagc | agctttgcca | tgagctgggt | ccgccaggct | 120 |
| ccagggaagg | ggctggaatg | ggtctcaact | attagtggta | gtggtggtta | cacattctac | 180 |
| gcagactccg | tgaagggccg | gttcaccatc | tccagagaca | attccaagaa | cacgctgtat | 240 |
| ctgcaaatga | acagcctgag | agccgaggac | acggccgtat | attactgtgc | gaaagatgga | 300 |
| aggtataact | ggaactacgg | ggcttttgat | atctggggcc | aagggacaat | ggtcaccgtc | 360 |
| tcttcagctt | ccaccaaggg | cccatccgtc | ttccccctgg | cgccctgctc | caggagcacc | 420 |
| tccgagagca | cagccgccct | gggctgcctg | gtcaaggact | acttccccga | accggtgacg | 480 |
| gtgtcgtgga | actcaggcgc | cctgaccagc | ggcgtgcaca | ccttcccggc | tgtcctacag | 540 |
| tcctcaggac | tctactccct | cagcagcgtg | gtgaccgtgc | cctccagcag | cttgggcacg | 600 |
| aagacctaca | cctgcaacgt | agatcacaag | cccagcaaca | ccaaggtgga | caagagagtt | 660 |
| gagtccaaat | atggtccccc | atgcccatca | tgcccagcac | ctgagttcct | ggggggacca | 720 |
| tcagtcttcc | tgttcccccc | aaaacccaag | gacactctca | tgatctcccg | gacccctgag | 780 |
| gtcacgtgcg | tggtggtgga | cgtgagccag | gaagaccccg | aggtccagtt | caactggtac | 840 |
| gtggatggcg | tggaggtgca | taatgccaag | acaaagccgc | gggaggagca | gttcaacagc | 900 |
| acgtaccgtg | tggtcagcgt | cctcaccgtc | ctgcaccagg | actggctgaa | cggcaaggag | 960 |
| tacaagtgca | aggtctccaa | caaaggcctc | ccgtcctcca | tcgagaaaac | catctccaaa | 1020 |
| gccaaagggc | agccccgaga | gccacaggtg | tacaccctgc | ccccatccca | ggaggagatg | 1080 |
| accaagaacc | aggtcagcct | gacctgcctg | gtcaaaggct | tctacccag | cgacatcgcc | 1140 |
| gtggagtggg | agagcaatgg | gcagccggag | aacaactaca | agaccacgcc | tcccgtgctg | 1200 |
| gactccgacg | gctccttctt | cctctacagc | aggctaaccg | tggacaagag | caggtggcag | 1260 |
| gaggggaatg | tcttctcatg | ctccgtgatg | catgaggctc | tgcacaacca | ctacacacag | 1320 |
| aagagcctct | ccctgtctct | gggtaaatga | | | | 1350 |

<210> SEQ ID NO 26
<211> LENGTH: 449
<212> TYPE: PRT
<213> ORGANISM: Homo sapiens

<400> SEQUENCE: 26

Glu Val Gln Leu Leu Glu Ser Gly Gly Gly Leu Ile Gln Pro Gly Gly
  1               5                  10                  15

Ser Leu Arg Leu Ser Cys Ala Ala Ser Gly Phe Thr Phe Ser Ser Phe
             20                  25                  30

Ala Met Ser Trp Val Arg Gln Ala Pro Gly Lys Gly Leu Glu Trp Val
         35                  40                  45

Ser Thr Ile Ser Gly Ser Gly Gly Tyr Thr Phe Tyr Ala Asp Ser Val
     50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gly Arg Tyr Asn Trp Asn Tyr Gly Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 27
<211> LENGTH: 645
<212> TYPE: DNA
<213> ORGANISM: Homo sapiens
```

<400> SEQUENCE: 27

```
gaaatagtga tgacgcagtc tccagccacc ctgtctgtgt ctccagggga aagagccacc      60
ctctcctgca gggccagtca gagtgttagt agcaacttag cctggtacca gcagaaacct     120
ggccaggctc ccaggctcct catctatggt gcatccacca gggccactgg tttcccagcc     180
aggttcagtg gcagtgggtc tgggacagag ttcactctca ccatcagcag cctgcagtct     240
gaagattttg caatttatta ctgtcagcag tataataact ggccgctcac tttcggcggg     300
gggaccaagg tggagatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacccctgacg    540 ctgagcaaag cagactacga aaacacaaa gtctacgcct gcgaagtcac ccatcagggc      600
ctgagctcgc ccgtcacaaa gagcttcaac aggggagagt gttag                    645
```

<210> SEQ ID NO 28
<211> LENGTH: 214
<212> TYPE: PRT
<213> ORGANISM: Homo sapiens

<400> SEQUENCE: 28

```
Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Phe Pro Ala Arg Phe Ser Gly
     50                  55                  60

Ser Gly Ser Gly Thr Glu Phe Thr Leu Thr Ile Ser Ser Leu Gln Ser
 65                  70                  75                  80

Glu Asp Phe Ala Ile Tyr Tyr Cys Gln Gln Tyr Asn Asn Trp Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 29
<211> LENGTH: 1338
<212> TYPE: DNA
<213> ORGANISM: Homo sapiens

<400> SEQUENCE: 29

```
gaggtgcagc tggtggagtc tgggggaggc ctggtcaagc ctggggggtc cctgagactc    60
tcctgtgcag cctctggatt caccttcagt agctatagca tgaactgggt ccgccaggct   120
ccagggaagg ggctggagtg ggtctcatcc attagtagta gtagtagtta catatactac   180
gcagactcag tgaagggccg attcaccatc tccagagaca acgccaagaa ctcactgtat   240
ctgcaaatga acagcctgag agccgaggac acggctgtgt attactgtgc gagagaccgt   300
gggagctact cctctttga ctactggggc cagggaaccc tggtcaccgt ctcctcagcc    360
tccaccaagg gcccatcggt cttccccctg gcgccctgct ccaggagcac ctccgagagc    420
acagcggccc tgggctgcct ggtcaaggac tacttccccg aaccggtgac ggtgtcgtgg    480
aactcaggcg ctctgaccag cggcgtgcac accttcccag ctgtcctaca gtcctcagga    540
ctctactccc tcagcagcgt ggtgaccgtg ccctccagca cttcggcac ccagacctac     600
acctgcaacg tagatcacaa gcccagcaac accaaggtgg acaagacagt tgagcgcaaa    660
tgttgtgtcg agtgcccacc gtgcccagca ccacctgtgg caggaccgtc agtcttcctc    720
ttcccccaa aacccaagga caccctcatg atctcccgga cccctgaggt cacgtgcgtg     780
gtggtggacg tgagccacga agaccccgag gtccagttca actggtacgt ggacggcgtg    840
gaggtgcata atgccaagac aaagccacgg gaggagcagt tcaacagcac gttccgtgtg    900
gtcagcgtcc tcaccgttgt gcaccaggac tggctgaacg gcaaggagta caagtgcaag    960
gtctccaaca aaggcctccc agcccccatc gagaaaacca tctccaaaac caaagggcag   1020
ccccgagaac cacaggtgta caccctgccc ccatcccggg aggagatgac caagaaccag   1080
gtcagcctga cctgcctggt caaaggcttc taccccagcg acatcgccgt ggagtgggag   1140
agcaatgggc agccggagaa caactacaag accacacctc ccatgctgga ctccgacggc   1200
tccttcttcc tctacagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gtaaatga                                                 1338
```

<210> SEQ ID NO 30
<211> LENGTH: 445
<212> TYPE: PRT
<213> ORGANISM: Homo sapiens

<400> SEQUENCE: 30

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ser Tyr Ser Ser Leu Phe Asp Tyr Trp Gly Gln Gly
            100                 105                 110

Thr Leu Val Thr Val Ser Ser Ala Ser Thr Lys Gly Pro Ser Val Phe
        115                 120                 125
```

```
Pro Leu Ala Pro Cys Ser Arg Ser Thr Ser Glu Ser Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Asn Phe Gly Thr Gln Thr Tyr Thr Cys Asn Val Asp His Lys Pro
        195                 200                 205
Ser Asn Thr Lys Val Asp Lys Thr Val Glu Arg Lys Cys Cys Val Glu
    210                 215                 220
Cys Pro Pro Cys Pro Ala Pro Pro Val Ala Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Gln
                260                 265                 270
Phe Asn Trp Tyr Val Asp Gly Val Glu Val His Asn Ala Lys Thr Lys
            275                 280                 285
Pro Arg Glu Glu Gln Phe Asn Ser Thr Phe Arg Val Val Ser Val Leu
        290                 295                 300
Thr Val Val His Gln Asp Trp Leu Asn Gly Lys Glu Tyr Lys Cys Lys
305                 310                 315                 320
Val Ser Asn Lys Gly Leu Pro Ala Pro Ile Glu Lys Thr Ile Ser Lys
                325                 330                 335
Thr Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
370                 375                 380
Pro Glu Asn Asn Tyr Lys Thr Thr Pro Pro Met Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
        435                 440                 445

<210> SEQ ID NO 31
<211> LENGTH: 645
<212> TYPE: DNA
<213> ORGANISM: Homo sapiens

<400> SEQUENCE: 31
gacatgcaga tgacccagtc tccatcctcc ctgtctgcat ctgtaggaga cagagtcacc    60
atcacttgcc gggcaagtca gggcattaga aatgatttag ctggtatca gcagaaacca   120 gggaaagccc ctaagcgcct gatctatggt gcatccagtt tgcaaagtgg ggtcccatca   180
aggttcagcg gcagtggatc tgggacagaa ttcactctca caatcagcag cctgcagcct   240
gaagattctg caacttatta ctgtctacag cataatagtt acccgctcac tttcggcgga   300
gggaccaagg tggagatcaa acgaactgtg gctgcaccat ctgtcttcat cttcccgcca   360
```

```
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645
```

<210> SEQ ID NO 32
<211> LENGTH: 214
<212> TYPE: PRT
<213> ORGANISM: Homo sapiens

<400> SEQUENCE: 32

```
Asp Met Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Gly Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Ser Ala Thr Tyr Tyr Cys Leu Gln His Asn Ser Tyr Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 33
<211> LENGTH: 1338
<212> TYPE: DNA
<213> ORGANISM: Homo sapiens

<400> SEQUENCE: 33

```
gaggtgcagc tggtggagtc tgggggaggc ctggtcaagc ctggggggtc cctgagactc    60
tcctgtgcag cctctggatt caccttcagt agctatagca tgaactgggt ccgccaggct    120
ccagggaagg ggctggagtg gtctctcatc attagtagta gtagtagtta catatactac    180
gcagactcag tgaagggccg attcaccatc tccagagaca acgccaagaa ctcactgtat    240
ctgcaaatga acagcctgag agccgaggac acggctgtgt attactgtgc gagagatcgt    300
ggatacagct atggtcttga ctactggggc cagggaaccc tggtcaccgt ctcctcagcc    360
```

```
tccaccaagg gcccatcggt cttcccctg gcgccctgct ccaggagcac ctccgagagc    420
acagcggccc tgggctgcct ggtcaaggac tacttccccg aaccggtgac ggtgtcgtgg    480
aactcaggcg ctctgaccag cggcgtgcac accttcccag ctgtcctaca gtcctcagga    540
ctctactccc tcagcagcgt ggtgaccgtg ccctccagca acttcggcac ccagacctac    600
acctgcaacg tagatcacaa gcccagcaac accaaggtgg acaagacagt tgagcgcaaa    660
tgttgtgtcg agtgcccacc gtgcccagca ccacctgtgg caggaccgtc agtcttcctc    720
ttccccccaa aacccaagga caccctcatg atctcccgga cccctgaggt cacgtgcgtg    780
gtggtggacg tgagccacga agaccccgag gtccagttca actggtacgt ggacggcgtg    840
gaggtgcata atgccaagac aaagccacgg gaggagcagt tcaacagcac gttccgtgtg    900
gtcagcgtcc tcaccgttgt gcaccaggac tggctgaacg gcaaggagta caagtgcaag    960
gtctccaaca aaggcctccc agccccatc gagaaaacca tctccaaaac caaagggcag   1020
ccccgagaac cacaggtgta caccctgccc ccatcccggg aggagatgac caagaaccag   1080
gtcagcctga cctgcctggt caaaggcttc taccccagcg acatcgccgt ggagtgggag   1140
agcaatgggc agccggagaa caactacaag accacacctc ccatgctgga ctccgacggc   1200
tccttcttcc tctacagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gtaaatga                                                 1338
```

<210> SEQ ID NO 34
<211> LENGTH: 445
<212> TYPE: PRT
<213> ORGANISM: Homo sapiens

<400> SEQUENCE: 34

```
Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
         35                  40                  45

Ser Ser Ile Ser Ser Ser Ser Tyr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Gly Tyr Ser Tyr Gly Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Asn Phe Gly Thr Gln Thr Tyr Thr Cys Asn Val Asp His Lys Pro
        195                 200                 205
Ser Asn Thr Lys Val Asp Lys Thr Val Glu Arg Lys Cys Cys Val Glu
        210                 215                 220
Cys Pro Pro Cys Pro Ala Pro Pro Val Ala Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Gln
            260                 265                 270
Phe Asn Trp Tyr Val Asp Gly Val Glu Val His Asn Ala Lys Thr Lys
        275                 280                 285
Pro Arg Glu Glu Gln Phe Asn Ser Thr Phe Arg Val Val Ser Val Leu
    290                 295                 300
Thr Val Val His Gln Asp Trp Leu Asn Gly Lys Glu Tyr Lys Cys Lys
305                 310                 315                 320
Val Ser Asn Lys Gly Leu Pro Ala Pro Ile Glu Lys Thr Ile Ser Lys
                325                 330                 335
Thr Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Met Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
        435                 440                 445

<210> SEQ ID NO 35
<211> LENGTH: 645
<212> TYPE: DNA
<213> ORGANISM: Homo sapiens

<400> SEQUENCE: 35
gacatccaga tgacccagtc tccatcctcc ctgtctgcat ctgtaggaga cagagtcacc        60
atcacttgcc gggcaagtca gggcattaga aatgatttag ctggtatca gcagaaacca       120 gggaaagccc ctaagcgcct gatctatgct gcatccagtt tgcaaagtgg ggtcccatca       180
aggttcagcg gcagtggatc tgggacagaa ttcactctca caatcagcag cctgcagcct       240
gaagattttg cgacttatta ctgtctacag cttaatagtt acccattcac tttcggccct       300
gggaccaaag tggatatcaa acgaactgtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag caccctgacg       540
ctgagcaaag cagactacga gaaacacaaa gtctacgcct gcgaagtcac ccatcagggc       600
ctgagctcgc ccgtcacaaa gagcttcaac aggggagagt gttag                      645
```

<210> SEQ ID NO 36
<211> LENGTH: 214
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Leu Asn Ser Tyr Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 1350
<212> TYPE: DNA
<213> ORGANISM: Homo sapiens

<400> SEQUENCE: 37
gaggtgcagc tattggagtc tgggggaggc ttgatacagc ctggggggtc cctgagactc      60
tcctgtgcag cctctggatt cacctttagc agctttgcca tgagctgggt ccgccaggct     120
ccagggaagg ggctggaatg ggtctcaact attagtggta gtggtggtag cacatactac     180
gcagacttcg tgaagggccg gttcaccatc tccagagaca attccaagaa cacgctgtat     240
ctgcaaatga acagcctgag agccgaggac acggccgtat attactgtgc gaaagatgga     300
aggtataact ggaactacgg ggcttttgat atctggggcc aagggacaat ggtcaccgtc     360
tcttcagctt ccaccaaggg cccatccgtc ttccccctgg cgccctgctc caggagcacc     420
tccgagagca cagccgccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
aagacctaca cctgcaacgt agatcacaag cccagcaaca ccaaggtgga caagagagtt     660

-continued

```
gagtccaaat atggtccccc atgcccatca tgcccagcac ctgagttcct ggggggacca    720
tcagtcttcc tgttcccccc aaaacccaag gacactctca tgatctcccg acccctgag    780 gtcacgtgcg tggtggtgga cgtgagccag aagaccccg aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa   1020
gccaaagggc agccccgaga gccacaggtg tacaccctgc ccccatccca ggaggagatg   1080
accaagaacc aggtcagcct gacctgcctg gtcaaaggct tctacccag cgacatcgcc   1140 gtggagtggg agagcaatgg gcagccggag aacaactaca agaccacgcc tcccgtgctg   1200
gactccgacg gctccttctt cctctacagc aggctaaccg tggacaagag caggtggcag   1260
gaggggaatg tcttctcatg ctccgtgatg catgaggctc tgcacaacca ctacacacag   1320
aagagcctct ccctgtctct gggtaaatga                                    1350
```

<210> SEQ ID NO 38
<211> LENGTH: 449
<212> TYPE: PRT
<213> ORGANISM: Homo sapiens

<400> SEQUENCE: 38

```
Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Ser Ser Phe
             20                  25                  30

Ala Met Ser Trp Val Arg Gln Ala Pro Gly Lys Gly Leu Glu Trp Val
         35                  40                  45

Ser Thr Ile Ser Gly Ser Gly Gly Ser Thr Tyr Tyr Ala Asp Phe Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gly Arg Tyr Asn Trp Asn Tyr Gly Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
225                 230                 235                 240
```

-continued

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys
```

<210> SEQ ID NO 39
<211> LENGTH: 645
<212> TYPE: DNA
<213> ORGANISM: Homo sapiens

<400> SEQUENCE: 39

| | | |
|---|---|---|
| gaaatagtga tgacgcagtc tccagccacc ctgtctgtgt ctccagggga aagagccacc | 60 |
| ctctcctgca gggccagtca gagtgttaga agcaatttag cctggttcca gcagaaacct | 120 |
| ggccaggctc ccaggctcct catctatggt gcatccacca gggccactgg tatcccagcc | 180 |
| aggttcagtg gcagtgggtc tgggacagag ttcactctca ccatcagcag cctgcagtct | 240 |
| gaagattttg cagtttatta ctgtcagcag tataataact ggccgctcac tttcggcgga | 300 |
| gggaccaagg tggagatcaa acgaactgtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gttag | 645 |

<210> SEQ ID NO 40
<211> LENGTH: 214
<212> TYPE: PRT
<213> ORGANISM: Homo sapiens

<400> SEQUENCE: 40

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Arg Ser Asn
            20                  25                  30

Leu Ala Trp Phe Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Leu
             85                  90                  95

Thr Phe Gly Gly Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210
```

<210> SEQ ID NO 41
<211> LENGTH: 1350
<212> TYPE: DNA
<213> ORGANISM: Homo sapiens

<400> SEQUENCE: 41

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacattctac     180
gcagactccg tgacgggccg gttcaccatc tccagagaca attccaagaa cacgctgttt     240
ctgcaattga cagcctgag agccgaggac acggccgtat atcactgtgc gaaagatgga      300
aggtttaact ggaactacgg ggcttctgat atctggggcc aagggaccat ggtcaccgtc     360
tcttcagctt ccaccaaggg cccatccgtc ttccccctgg cgccctgctc caggagcacc     420
tccgagagca cagccgccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
aagacctaca cctgcaacgt agatcacaag cccagcaaca ccaaggtgga caagagagtt     660
gagtccaaat atggtccccc atgcccatca tgcccagcac ctgagttcct ggggggacca     720
tcagtcttcc tgttcccccc aaaacccaag gacactctca tgatctcccg gacccctgag     780
gtcacgtgcg tggtggtgga cgtgagccag gaagaccccg aggtccagtt caactggtac     840
```

-continued

```
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa   1020
gccaaagggc agccccgaga gccacaggtg tacaccctgc ccccatccca ggaggagatg   1080
accaagaacc aggtcagcct gacctgcctg gtcaaaggct tctacccag cgacatcgcc    1140 gtggagtggg agagcaatgg gcagccggag aacaactaca agaccacgcc tcccgtgctg   1200
gactccgacg gctccttctt cctctacagc aggctaaccg tggacaagag caggtggcag   1260 gagggggaatg tcttctcatg ctccgtgatg catgaggctc tgcacaacca ctacacacag   1320
aagagcctct ccctgtctct gggtaaatga                                    1350
```

<210> SEQ ID NO 42
<211> LENGTH: 449
<212> TYPE: PRT
<213> ORGANISM: Homo sapiens

<400> SEQUENCE: 42

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Phe Tyr Ala Asp Ser Val
     50                  55                  60

Thr Gly Arg Phe Thr Ile Ser Arg Asp Asn Ser Lys Asn Thr Leu Phe
 65                  70                  75                  80

Leu Gln Leu Asn Ser Leu Arg Ala Glu Asp Thr Ala Val Tyr His Cys
                 85                  90                  95

Ala Lys Asp Gly Arg Phe Asn Trp Asn Tyr Gly Ala Ser Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285
```

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 43
<211> LENGTH: 645
<212> TYPE: DNA
<213> ORGANISM: Homo sapiens

<400> SEQUENCE: 43
gaaatagtga tgacgcagtc tccagccact ctgtctgtgt ctccagggga agagccacc      60 ctctcctgca ggaccagtca gagtgttagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag tataataact ggccgctcac tttcggcgga    300
gggaccaagg tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg   540 ctgagcaaag cagactacga gaaacacaaa gtctacgcct gcgaagtcac ccatcagggc    600
ctgagctcgc ccgtcacaaa gagcttcaac aggggagagt gttag                    645

<210> SEQ ID NO 44
<211> LENGTH: 214
<212> TYPE: PRT
<213> ORGANISM: Homo sapiens

<400> SEQUENCE: 44

Glu Ile Val Met Thr Gln Ser Pro Ala Thr Leu Ser Val Ser Pro Gly
  1               5                  10                  15

Glu Arg Ala Thr Leu Ser Cys Arg Thr Ser Gln Ser Val Ser Ser Asn
            20                  25                  30

Leu Ala Trp Tyr Gln Gln Lys Pro Gly Gln Ala Pro Arg Leu Leu Ile
        35                  40                  45

-continued

Tyr Gly Ala Ser Thr Arg Ala Thr Gly Ile Pro Ala Arg Phe Ser Gly
            50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 45
<211> LENGTH: 119
<212> TYPE: PRT
<213> ORGANISM: Homo sapiens

<400> SEQUENCE: 45

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Arg Gly Tyr Ser Tyr Gly Leu Asp Tyr Trp Gly Gln Gly
            100                 105                 110

Thr Leu Val Thr Val Ser Ser
        115

<210> SEQ ID NO 46
<211> LENGTH: 358
<212> TYPE: DNA
<213> ORGANISM: Homo sapiens

<400> SEQUENCE: 46
gaggtgcagc tggtggagtc tgggggaggc ctggtcaagc ctggggggtc cctgagactc     60
tcctgtgcag cctctggatt caccttcagt agctatagca tgaattgggt ccgccaggct    120
ccagggaagg ggctggagtg gtctcatcc attagtagta gtagtagtta catatactac    180

```
gcagactcag tgaagggccg attcaccatc tccagagaca acgccaagaa ctcactgtat    240
ctgcaaatga acagcctgag agccgaggac acggctgtgt attactgtgc gagagatcgg    300
gggtacagct atggtcttga ctactggggc cagggaaccc tggtcaccgt ctcctcag     358
```

<210> SEQ ID NO 47
<211> LENGTH: 107
<212> TYPE: PRT
<213> ORGANISM: Homo sapiens

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Ala
            20                  25                  30

Leu Gly Trp Tyr Gln Gln Lys Pro Gly Lys Ala Pro Gln Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Lys
            100                 105

<210> SEQ ID NO 48
<211> LENGTH: 322
<212> TYPE: DNA
<213> ORGANISM: Homo sapiens

<400> SEQUENCE: 48

```
gacatccaga tgacccagtc tccatcctcc ctgtctgcat ctgtaggaga cagagtcacc    60
atcacttgcc gggcaagtca gggcattaga aatgctttag ctggtatca  gcagaaacca   120 gggaaagccc ctcagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt accctcggac gttcggccaa    300
gggaccaagg tggaaatcaa ac                                             322
```

<210> SEQ ID NO 49
<211> LENGTH: 123
<212> TYPE: PRT
<213> ORGANISM: Homo sapiens

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Asn Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

```
Met Glu Leu Ser Arg Leu Arg Ser Asp Asp Thr Ala Val Tyr His Cys
            85                  90                  95

Ala Arg Asn Thr Val Gly Ser Gly Tyr Tyr Tyr Gly Met Asp Val
        100                 105                 110

Trp Gly Gln Gly Thr Thr Val Thr Val Ser Ser
        115                 120
```

<210> SEQ ID NO 50
<211> LENGTH: 370
<212> TYPE: DNA
<213> ORGANISM: Homo sapiens

<400> SEQUENCE: 50

```
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccctaacaatggtgg cacaaactat      180
gcacagaagt tcagggcag gtcaccatg accagggaca cgtccatcag cacagcctac      240
atggagctga gcaggctgag atctgacgac acggccgtgt atcactgtgc gagaaatacg     300
gtgggaagtg gtactacta ctacggtatg gacgtctggg gccaagggac cacggtcacc     360
gtctcctcag                                                           370
```

<210> SEQ ID NO 51
<211> LENGTH: 112
<212> TYPE: PRT
<213> ORGANISM: Homo sapiens

<400> SEQUENCE: 51

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Ser Gly Gln Ser
         35                  40                  45

Pro Gln Leu Leu Ile His Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Val
                 85                  90                  95

Leu Gln Thr Pro Leu Thr Phe Gly Gly Gly Thr Lys Val Glu Ile Lys
            100                 105                 110
```

<210> SEQ ID NO 52
<211> LENGTH: 337
<212> TYPE: DNA
<213> ORGANISM: Homo sapiens

<400> SEQUENCE: 52

```
gatattgtga tgactcagtc tccactctcc ctgcccgtca cccctggaga gccggcctcc      60
atctcctgca ggtctagtca gagcctcctg catagtaatg gatacaacta tttggattgg     120
tacctgcaga agtcagggca gtctccacag ctcctgatcc attgggttc aatcgggcc       180
tccggggtcc ctgacaggtt cagtggcagt ggatcaggca cagatttac actgaaaatc      240
agcagagtgg aggctgagga tgttggggtt tattactgca tgcaagttct acaaactccg     300
ctcactttcg gcggagggac caaggtggag atcaaac                             337
```

<210> SEQ ID NO 53
<211> LENGTH: 119
<212> TYPE: PRT
<213> ORGANISM: Homo sapiens

<400> SEQUENCE: 53

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Arg Gly Tyr Ser Tyr Gly Ile Asp Tyr Trp Gly Gln Gly
            100                 105                 110

Thr Leu Val Thr Val Ser Ser
        115
```

<210> SEQ ID NO 54
<211> LENGTH: 358
<212> TYPE: DNA
<213> ORGANISM: Homo sapiens

<400> SEQUENCE: 54

```
gaggtgcagc tggtggagtc tgggggaggc ctggtcaagc ctggggggtc cctgagactc      60
tcctgtgcag cctctggatt caccttcagt agctatagca tgaactgggt ccgccaggct     120
ccagggaagg gctggagtg gtctcatcc attagtagta gtagtagtta catatactac      180
gcagactcag tgaagggccg attcaccatc tccagagaca acgccaagaa ctcactgtat     240
ctgcaaatga acagcctgag agccgaggac acggctgtgt attactgtgc gagagatcgt     300
ggatacagct atggtattga ctactggggc cagggaaccc tggtcaccgt ctcctcag      358
```

<210> SEQ ID NO 55
<211> LENGTH: 107
<212> TYPE: PRT
<213> ORGANISM: Homo sapiens

<400> SEQUENCE: 55

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Ala
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Lys
            100                 105
```

<210> SEQ ID NO 56
<211> LENGTH: 322
<212> TYPE: DNA
<213> ORGANISM: Homo sapiens

<400> SEQUENCE: 56
gacatccaga tgacccagtc tccatcctcc ctgtctgcat ctgtaggaga cagagtcacc    60
atcacttgcc gggcaagtca gggcattaga aatgctttag ctggtatca gcagaaacca   120 gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt accctcggac gttcggccaa   300
gggaccaagg tggaaatcaa ac                                            322

<210> SEQ ID NO 57
<211> LENGTH: 119
<212> TYPE: PRT
<213> ORGANISM: Homo sapiens

<400> SEQUENCE: 57

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Tyr Tyr Tyr Gly Met Asp Val Trp Gly Gln Gly
            100                 105                 110

Thr Thr Val Thr Val Ser Ser
        115

<210> SEQ ID NO 58
<211> LENGTH: 358
<212> TYPE: DNA
<213> ORGANISM: Homo sapiens

<400> SEQUENCE: 58
gaggtgcagc tggtggagtc tgggggaggc ctggtcaagc ctggggggtc cctgagactc    60
tcctgtgcag cctctggatt caccttcagt agctatagca tgaactgggt ccgccaggct   120
ccagggaagg ggctggagtg gtctcatcc attagtagta gtagtagtta catatactac   180
gcagactcag tgaagggccg attcaccatc tccagagaca acgccaagaa ctcactgtat   240
ctgcaaatga acagcctgag agccgaggac acggctgtgt attactgtgc gagagatagg   300
ggatactact acggtatgga cgtctggggc caagggacca cggtcaccgt ctcctcag     358

<210> SEQ ID NO 59
<211> LENGTH: 107
<212> TYPE: PRT
<213> ORGANISM: Homo sapiens

<400> SEQUENCE: 59

Asp Ile Gln Met Thr Gln Ser Pro Ser Ser Leu Ser Ala Ser Val Gly
1               5                   10                  15

Asp Arg Val Thr Leu Thr Cys Arg Ala Ser Gln Gly Ile Arg Asn Ala
            20                  25                  30

Leu Gly Trp Tyr Gln Gln Lys Pro Gly Lys Ala Pro Lys Arg Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Phe
                85                  90                  95

Thr Phe Gly Pro Gly Thr Lys Val Asp Ile Lys
            100                 105

<210> SEQ ID NO 60
<211> LENGTH: 322
<212> TYPE: DNA
<213> ORGANISM: Homo sapiens

<400> SEQUENCE: 60

```
gacatccaga tgacccagtc tccatcctcc ctgtctgcat ctgtaggaga cagagtcacc    60
ctcacttgcc gggcaagtca gggcattaga aatgctttag ctggtatcag cagaaaacca   120
gggaaagccc ctaagcgcct gatctatggt gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt acccattcac tttcggccct   300
gggaccaaag tggatatcaa ac                                            322
```

<210> SEQ ID NO 61
<211> LENGTH: 119
<212> TYPE: PRT
<213> ORGANISM: Homo sapiens

<400> SEQUENCE: 61

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ser Tyr Phe Leu Phe Asp Tyr Trp Gly Gln Gly
            100                 105                 110

Thr Leu Val Thr Val Ser Ser
            115

<210> SEQ ID NO 62
<211> LENGTH: 358
<212> TYPE: DNA
<213> ORGANISM: Homo sapiens

<400> SEQUENCE: 62

```
gaggtgcagc tggtggagtc tgggggaggc ctggtcaagc ctgggggtc cctgagactc      60 tcctgtgcag cctctggatt caccttcagt agctatagca tgaactgggt ccgccaggct    120
ccagggaagg gctggagtg gtctcatcc attagtagta gtagtagtta catatactac      180
gcagactcag tgaagggccg attcaccatc tccagagaca acgccaagaa ctcactgtat    240
ctgcaaatga acagcctgag agccgaggac acggctgtgt attactgtgc gagagaccgt    300
gggagctact cctctttga ctactgggc cagggaaccc tggtcaccgt ctcctcag        358
```

<210> SEQ ID NO 63
<211> LENGTH: 107
<212> TYPE: PRT
<213> ORGANISM: Homo sapiens

<400> SEQUENCE: 63

```
Asp Met Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Gly Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Ser Ala Thr Tyr Tyr Cys Leu Gln His Asn Ser Tyr Pro Leu
             85                  90                  95

Thr Phe Gly Gly Gly Thr Lys Val Glu Ile Lys
            100                 105
```

<210> SEQ ID NO 64
<211> LENGTH: 322
<212> TYPE: DNA
<213> ORGANISM: Homo sapiens

<400> SEQUENCE: 64

```
gacatgcaga tgacccagtc tccatcctcc ctgtctgcat ctgtaggaga cagagtcacc      60
atcacttgcc gggcaagtca gggcattaga aatgatttag gctggtatca gcagaaacca    120
gggaaagccc ctaagcgcct gatctatggt gcatccagtt tgcaaagtgg ggtcccatca    180
aggttcagcg gcagtggatc tgggacagaa ttcactctca caatcagcag cctgcagcct    240
gaagattctg caacttatta ctgtctacag cataatagtt acccgctcac tttcggcgga    300
gggaccaagg tggagatcaa ac                                              322
```

<210> SEQ ID NO 65
<211> LENGTH: 119
<212> TYPE: PRT
<213> ORGANISM: Homo sapiens

<400> SEQUENCE: 65

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Thr Val Tyr Tyr Cys
                85                  90                  95

Ala Arg Asp Arg Gly Tyr Leu Tyr Gly Met Asp Val Trp Gly Gln Gly
            100                 105                 110

Thr Thr Val Thr Val Ser Ser
        115
```

<210> SEQ ID NO 66
<211> LENGTH: 358
<212> TYPE: DNA
<213> ORGANISM: Homo sapiens

<400> SEQUENCE: 66

```
gaggtgcagc tggtggagtc tgggggaggc ctggtcaagc ctggggggtc cctgagactc      60
tcctgtgcag cctctggatt caccttcagt agctatagca tgaactgggt ccgccaggct     120
ccagggaagg gctggagtg gtctcatcc attagtagta gtagtagtta catatactac      180
gcagactcag tgaagggccg attcaccatc tccagagaca acgccaagaa ctcactgtat     240
ctgcaaatga acagcctgag agccgaggac acgactgtgt attactgtgc gagagatcga     300
ggctacctct acggtatgga cgtctggggc caagggacca cggtcaccgt ctcctcag       358
```

<210> SEQ ID NO 67
<211> LENGTH: 107
<212> TYPE: PRT
<213> ORGANISM: Homo sapiens

<400> SEQUENCE: 67

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Lys
            100                 105
```

<210> SEQ ID NO 68
<211> LENGTH: 322
<212> TYPE: DNA
<213> ORGANISM: Homo sapiens

<400> SEQUENCE: 68

| gacatccaga tgacccagtc tccatcctcc ctgtctgcat ctgtaggaga cagagtcacc | 60 |
| atcacttgcc gggcaagtca ggccattaga aatgatttag ctggtatca gcagaaacca | 120 |
| gggaaagccc ctaagcgcct gatctatgct gcatccagtt tgcaaagtgg ggtcccatca | 180 |
| aggttcagcg gcagtggatc tgggacagaa ttcactctca caatcagcag cctgcagcct | 240 |
| gaagattttg caacttatta ctgtctacag cataatagtt accctcggac gttcggccaa | 300 |
| gggaccaagg tggaaatcaa ac | 322 |

<210> SEQ ID NO 69
<211> LENGTH: 123
<212> TYPE: PRT
<213> ORGANISM: Homo sapiens

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Leu Glu Leu Ser Arg Leu Arg Ser Asp Asp Thr Ala Val Tyr Tyr Cys
                85                  90                  95

Ala Arg Asn Thr Val Gly Thr Gly Tyr Tyr Tyr Gly Met Asp Val
            100                 105                 110

Trp Gly Gln Gly Thr Thr Val Thr Val Ser Ser
        115                 120

<210> SEQ ID NO 70
<211> LENGTH: 370
<212> TYPE: DNA
<213> ORGANISM: Homo sapiens

<400> SEQUENCE: 70

| caggtgcagc tggtgcagtc tggggctgag gtgaagaagc ctggggcctc agtgaaggtc | 60 |
| tcctgcaagg cttctggata taccttcacc ggctactata tgcactgggt gcgacaggcc | 120 |
| cctggacaag gcttgagtg gatgggatgg atcaaccta acagtggtgg cacaaactat | 180 |
| gcacagaagt tcagggcag ggtcaccatg accaggaca cgtccatcag cacagcctac | 240 |
| ctggagctga gcaggctgag atctgacgac acggccgtgt attactgtgc gagaaatacg | 300 |
| gtgggaactg gatactacta ctacggtatg gacgtctggg gccaagggac cacggtcacc | 360 |
| gtctcctcag | 370 |

<210> SEQ ID NO 71
<211> LENGTH: 112
<212> TYPE: PRT
<213> ORGANISM: Homo sapiens

<400> SEQUENCE: 71

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Val Leu Ile Tyr Leu Val Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Pro Thr Phe Gly Gly Gly Thr Lys Val Glu Ile Lys
            100                 105                 110
```

<210> SEQ ID NO 72
<211> LENGTH: 337
<212> TYPE: DNA
<213> ORGANISM: Homo sapiens

<400> SEQUENCE: 72

```
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag gtcctgatct atttggtttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactcct   300
cccactttcg gcggagggac caaggtggag atcaaac                            337
```

<210> SEQ ID NO 73
<211> LENGTH: 119
<212> TYPE: PRT
<213> ORGANISM: Homo sapiens

<400> SEQUENCE: 73

```
Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
         35                  40                  45

Ser Ser Ile Ser Ser Ser Ser Ser Tyr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Gly Tyr Ser Tyr Gly Leu Asp Tyr Trp Gly Gln Gly
            100                 105                 110

Thr Leu Val Thr Val Ser Ser
            115
```

<210> SEQ ID NO 74
<211> LENGTH: 358
<212> TYPE: DNA
<213> ORGANISM: Homo sapiens

<400> SEQUENCE: 74

```
gaggtgcagc tggtggagtc tgggggaggc ctggtcaagc ctgggggtc cctgagactc      60
tcctgtgcag cctctggatt caccttcagt agctatagca tgaactgggt ccgccaggct    120
ccagggaagg gctggagtg gtctcatcc attagtagta gtagtagtta catatactac     180
gcagactcag tgaagggccg attcaccatc tccagagaca acgccaagaa ctcactgtat    240
ctgcaaatga acagcctgag agccgaggac acggctgtgt attactgtgc gagagatcgt    300
ggatacagct atggtcttga ctactgggc cagggaaccc tggtcaccgt ctcctcag      358
```

<210> SEQ ID NO 75
<211> LENGTH: 107
<212> TYPE: PRT
<213> ORGANISM: Homo sapiens

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Leu Asn Ser Tyr Pro Phe
                85                  90                  95

Thr Phe Gly Pro Gly Thr Lys Val Asp Ile Lys
            100                 105

<210> SEQ ID NO 76
<211> LENGTH: 322
<212> TYPE: DNA
<213> ORGANISM: Homo sapiens

<400> SEQUENCE: 76

```
gacatccaga tgacccagtc tccatcctcc ctgtctgcat ctgtaggaga cagagtcacc     60
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg cgacttatta ctgtctacag cttaatagtt acccattcac tttcggccct    300
gggaccaaag tggatatcaa ac                                             322
```

<210> SEQ ID NO 77
<211> LENGTH: 122
<212> TYPE: PRT
<213> ORGANISM: Homo sapiens

<400> SEQUENCE: 77

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Tyr Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Arg Tyr Asn Trp Asn Tyr Gly Ala Phe Asp Ile Trp
            100                 105                 110

Gly Gln Gly Thr Met Val Thr Val Ser Ser
        115                 120

<210> SEQ ID NO 78
<211> LENGTH: 367
<212> TYPE: DNA
<213> ORGANISM: Homo sapiens

<400> SEQUENCE: 78
gaggtgcagc tattggagtc tgggggaggc ttgatacagc ctggggggtc cctgagactc      60
tcctgtgcag cctctggatt cacctttagc agctttgcca tgagctgggt ccgccaggct     120
ccagggaagg gctggaatg gtctcaact attagtggta gtggtggtta cacattctac       180
gcagactccg tgaagggccg gttcaccatc tccagagaca attccaagaa cacgctgtat     240
ctgcaaatga acagcctgag agccgaggac acggccgtat attactgtgc gaaagatgga     300
aggtataact ggaactacgg ggcttttgat atctggggcc aagggacaat ggtcaccgtc     360
tcttcag                                                               367

<210> SEQ ID NO 79
<211> LENGTH: 107
<212> TYPE: PRT
<213> ORGANISM: Homo sapiens

<400> SEQUENCE: 79

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Phe Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Ile Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 80
<211> LENGTH: 322
<212> TYPE: DNA
<213> ORGANISM: Homo sapiens

<400> SEQUENCE: 80

```
gaaatagtga tgacgcagtc tccagccacc ctgtctgtgt ctccagggga aagagccacc      60
ctctcctgca gggccagtca gagtgttagt agcaacttag cctggtacca gcagaaacct     120
ggccaggctc ccaggctcct catctatggt gcatccacca gggccactgg tttcccagcc     180
aggttcagtg gcagtgggtc tgggacagag ttcactctca ccatcagcag cctgcagtct     240
gaagattttg caatttatta ctgtcagcag tataataact ggccgctcac tttcggcggg     300
gggaccaagg tggagatcaa ac                                              322
```

<210> SEQ ID NO 81
<211> LENGTH: 122
<212> TYPE: PRT
<213> ORGANISM: Homo sapiens

<400> SEQUENCE: 81

```
Glu Val Gln Leu Leu Glu Ser Gly Gly Gly Leu Ile Gln Pro Gly Gly
  1               5                  10                  15

Ser Leu Arg Leu Ser Cys Ala Ala Ser Gly Phe Thr Phe Ser Ser Phe
             20                  25                  30

Ala Met Ser Trp Val Arg Gln Ala Pro Gly Lys Gly Leu Glu Trp Val
         35                  40                  45

Ser Thr Ile Ser Gly Ser Gly Gly Ser Thr Tyr Tyr Ala Asp Phe Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gly Arg Tyr Asn Trp Asn Tyr Gly Ala Phe Asp Ile Trp
            100                 105                 110

Gly Gln Gly Thr Met Val Thr Val Ser Ser
        115                 120
```

<210> SEQ ID NO 82
<211> LENGTH: 367
<212> TYPE: DNA
<213> ORGANISM: Homo sapiens

<400> SEQUENCE: 82

```
gaggtgcagc tattggagtc tgggggaggc ttgatacagc ctgggggtc cctgagactc       60
tcctgtgcag cctctggatt cacctttagc agctttgcca tgagctgggt ccgccaggct     120
ccagggaagg ggctggaatg ggtctcaact attagtggta gtggtggtag cacatactac     180
gcagacttcg tgaagggccg gttcaccatc tccagagaca attccaagaa cacgctgtat     240
ctgcaaatga acagcctgag agccgaggac acggccgtat attactgtgc gaaagatgga     300
aggtataact ggaactacgg ggcttttgat atctggggcc aagggacaat ggtcaccgtc     360
tcttcag                                                               367
```

<210> SEQ ID NO 83
<211> LENGTH: 107
<212> TYPE: PRT
<213> ORGANISM: Homo sapiens

<400> SEQUENCE: 83

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Asn
            20                  25                  30

Leu Ala Trp Phe Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 84
<211> LENGTH: 322
<212> TYPE: DNA
<213> ORGANISM: Homo sapiens

<400> SEQUENCE: 84
gaaatagtga tgacgcagtc tccagccacc ctgtctgtgt ctccagggga aagagccacc      60
ctctcctgca gggccagtca gagtgttaga agcaatttag cctggttcca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag tataataact ggccgctcac tttcggcgga    300
gggaccaagg tggagatcaa ac                                              322

<210> SEQ ID NO 85
<211> LENGTH: 122
<212> TYPE: PRT
<213> ORGANISM: Homo sapiens

<400> SEQUENCE: 85

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Phe Tyr Ala Asp Ser Val
    50                  55                  60

Thr Gly Arg Phe Thr Ile Ser Arg Asp Asn Ser Lys Asn Thr Leu Phe
65                  70                  75                  80

Leu Gln Leu Asn Ser Leu Arg Ala Glu Asp Thr Ala Val Tyr His Cys
                85                  90                  95

Ala Lys Asp Gly Arg Phe Asn Trp Asn Tyr Gly Ala Ser Asp Ile Trp
            100                 105                 110

Gly Gln Gly Thr Met Val Thr Val Ser Ser
        115                 120

<210> SEQ ID NO 86
<211> LENGTH: 367
<212> TYPE: DNA
<213> ORGANISM: Homo sapiens

<400> SEQUENCE: 86

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacattctac     180
gcagactccg tgacgggccg gttcaccatc tccagagaca attccaagaa cacgctgttt     240
ctgcaattga acagcctgag agccgaggac acggccgtat atcactgtgc gaaagatgga     300
aggtttaact ggaactacgg ggcttctgat atctggggcc aagggaccat ggtcaccgtc     360
tcttcag                                                               367
```

<210> SEQ ID NO 87
<211> LENGTH: 107
<212> TYPE: PRT
<213> ORGANISM: Homo sapiens

<400> SEQUENCE: 87

```
Glu Ile Val Met Thr Gln Ser Pro Ala Thr Leu Ser Val Ser Pro Gly
  1               5                  10                  15

Glu Arg Ala Thr Leu Ser Cys Arg Thr Ser Gln Ser Val Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
     50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Leu
                 85                  90                  95

Thr Phe Gly Gly Gly Thr Lys Val Glu Ile Lys
            100                 105
```

<210> SEQ ID NO 88
<211> LENGTH: 322
<212> TYPE: DNA
<213> ORGANISM: Homo sapiens

<400> SEQUENCE: 88

```
gaaatagtga tgacgcagtc tccagccact ctgtctgtgt ctccagggga aagagccacc      60
ctctcctgca ggaccagtca gagtgttagc agcaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcag tataataact ggccgctcac tttcggcgga     300
gggaccaagg tggagatcaa ac                                              322
```

<210> SEQ ID NO 89
<211> LENGTH: 109
<212> TYPE: PRT
<213> ORGANISM: Homo sapiens

<400> SEQUENCE: 89

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105

<210> SEQ ID NO 90
<211> LENGTH: 109
<212> TYPE: PRT
<213> ORGANISM: Homo sapiens

<400> SEQUENCE: 90

Asn Leu Gly Leu Asp Cys Asp Glu His Ser Ser Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Gln Cys Glu
        35                  40                  45

Tyr Met Phe Met Gln Lys Tyr Pro His Thr His Leu Val Gln Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Asp Lys Gln Gln Ile Ile Tyr Gly
                85                  90                  95

Lys Ile Pro Gly Met Val Val Asp Arg Cys Gly Cys Ser
            100                 105

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)
<223> OTHER INFORMATION: Inosine

<400> SEQUENCE: 91
caggtgcagc tggagcagtc ngg                                           23

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 92
gctgagggag tagagtcctg agga                                          24

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
tacgtgccaa gcatcctcgc                                               20

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
aggctggaac tgaggagcag gtg                                           23

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ccctgagagc atcaymyarm aacc                                          24

<210> SEQ ID NO 96
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
hvthtccact yggtgatcrg cactg                                         25

<210> SEQ ID NO 97
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
attyrgtgat cagsactgaa casag                                         25

<210> SEQ ID NO 98
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 98
gsartcagwc ycwvycagga cacagc                                26

<210> SEQ ID NO 99
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
caccaggkga tttgcatatt rtccc                                 25

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
atcaatgcct gkgtcagagc yytg                                  24

<210> SEQ ID NO 101
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101 agccagaca                                                   9

<210> SEQ ID NO 102
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102 gtctagac                                                    8

<210> SEQ ID NO 103
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Asp Phe Gly Leu Asp Cys Asp Glu His Ser Thr Glu Ser Arg Cys Cys
 1               5                  10                  15

Arg Tyr

<210> SEQ ID NO 104
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 104

Pro Leu Thr Val Asp Phe Glu Ala Phe Gly Trp Asp Trp Ile Ile Ala
 1               5                  10                  15

Pro Lys

<210> SEQ ID NO 105
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Arg Tyr Lys Ala Asn Tyr Cys Ser Gly Glu Cys Glu Phe Val Phe Leu
 1               5                  10                  15

Gln Lys

<210> SEQ ID NO 106
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Tyr Pro His Thr His Leu Val His Gln Ala Asn Pro Arg Gly Ser Ala
 1               5                  10                  15

Gly Pro

<210> SEQ ID NO 107
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Cys Cys Thr Pro Thr Lys Met Ser Pro Ile Asn Met Leu Tyr Phe Asn
 1               5                  10                  15

Gly Lys

<210> SEQ ID NO 108
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Glu Gln Ile Ile Tyr Gly Lys Ile Pro Ala Met Val Val Asp Arg Cys
 1               5                  10                  15

Gly Cys Ser
```

```
<210> SEQ ID NO 109
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

His Ser Thr Glu Ser Arg Cys Cys Arg Tyr Pro Leu Thr Val Asp Phe
 1               5                  10                  15

Glu Ala

<210> SEQ ID NO 110
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Phe Gly Trp Asp Trp Ile Ile Ala Pro Lys Arg Tyr Lys Ala Asn Tyr
 1               5                  10                  15

Cys Ser

<210> SEQ ID NO 111
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Glu Cys Glu Phe Val Phe Leu Gln Lys Tyr Pro His Thr His Leu
 1               5                  10                  15

Val His

<210> SEQ ID NO 112
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gln Ala Asn Pro Arg Gly Ser Ala Gly Pro Cys Cys Thr Pro Thr Lys
 1               5                  10                  15

Met Ser

<210> SEQ ID NO 113
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Pro Ile Asn Met Leu Tyr Phe Asn Gly Lys Glu Gln Ile Ile Tyr Gly
 1               5                  10                  15

Lys Ile
```

<210> SEQ ID NO 114
<211> LENGTH: 1347
<212> TYPE: DNA
<213> ORGANISM: Homo sapiens

<400> SEQUENCE: 114

```
gaggtgcagc tgttggagtc tgggggaggc ttggtacagc ctggggggtc cctgagactc      60
tcctgtgcag cctctggatt cacctttagc agctttgcca tgagctgggt ccgccaggct     120
ccagggaagg ggctggaatg ggtctcaact attagtggta gtggtggtta cacattctac     180
gcagactccg tgaagggccg gttcaccatc tccagagaca attccaagaa cacgctgtat     240
ctgcaaatga acagcctgag agccgaggac acggccgtat attactgtgc gaaagatgga     300
aggtataact ggaactacgg ggcttttgat atctggggcc aagggacaat ggtcaccgtc     360
tcctcagcct ccaccaaggg cccatcggtc ttccccctgg cgccctgctc caggagcacc     420
tccgagagca cagcggccct gggctgcctg gtcaaggact acttccccga accggtgacg     480
gtgtcgtgga actcaggcgc tctgaccagc ggcgtgcaca ccttcccggc tgtcctacag     540
tcctcaggac tctactccct cagcagcgta gtgaccgtgc cctccagcaa cttcggcacc     600
cagacctaca cctgcaacgt agatcacaag cccagcaaca ccaaggtgga caagacagtt     660
gagcgcaaat gttgtgtcga gtgcccaccg tgcccagcac cacctgtggc aggaccgtca     720
gtcttcctct tccccccaaa acccaaggac accctcatga tctcccggac ccctgaggtc     780
acgtgcgtgg tggtggacgt gagccacgaa gaccccgagg tccagttcaa ctggtacgtg     840
gacggcgtgg aggtgcataa tgccaagaca aagccacggg aggagcagtt caacagcacg     900
ttccgtgtgg tcagcgtcct caccgtcgtg caccaggact ggctgaacgg caaggagtac     960
aagtgcaagg tctccaacaa aggcctccca gcccccatcg agaaaaccat ctccaaaacc    1020
aaagggcagc cccgagaacc acaggtgtac accctgcccc catcccggga ggagatgacc    1080
aagaaccagg tcagcctgac ctgcctggtc aaaggcttct accccagcga catcgccgtg    1140
gagtgggaga gcaatgggca gccggagaac aactacaaga ccacacctcc catgctggac    1200
tccgacggct ccttcttcct ctacagcaag ctcaccgtgg acaagagcag gtggcagcag    1260
gggaacgtct tctcatgctc cgtgatgcat gaggctctgc acaaccacta cacacagaag    1320
agcctctccc tgtctccggg taaatga                                        1347
```

<210> SEQ ID NO 115
<211> LENGTH: 448
<212> TYPE: PRT
<213> ORGANISM: Homo sapiens

<400> SEQUENCE: 115

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Phe
             20                  25                  30

Ala Met Ser Trp Val Arg Gln Ala Pro Gly Lys Gly Leu Glu Trp Val
         35                  40                  45

Ser Thr Ile Ser Gly Ser Gly Gly Tyr Thr Phe Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

-continued

```
Ala Lys Asp Gly Arg Tyr Asn Trp Asn Tyr Gly Ala Phe Asp Ile Trp
                100                 105                 110
Gly Gln Gly Thr Met Val Thr Val Ser Ser Ala Ser Thr Lys Gly Pro
            115                 120                 125
Ser Val Phe Pro Leu Ala Pro Cys Ser Arg Ser Thr Ser Glu Ser Thr
        130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Asn Phe Gly Thr Gln Thr Tyr Thr Cys Asn Val Asp
        195                 200                 205
His Lys Pro Ser Asn Thr Lys Val Asp Lys Thr Val Glu Arg Lys Cys
210                 215                 220
Cys Val Glu Cys Pro Pro Cys Pro Ala Pro Pro Val Ala Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Gln Phe Asn Trp Tyr Val Asp Gly Val Glu Val His Asn Ala
        275                 280                 285
Lys Thr Lys Pro Arg Glu Glu Gln Phe Asn Ser Thr Phe Arg Val Val
    290                 295                 300
Ser Val Leu Thr Val Val His Gln Asp Trp Leu Asn Gly Lys Glu Tyr
305                 310                 315                 320
Lys Cys Lys Val Ser Asn Lys Gly Leu Pro Ala Pro Ile Glu Lys Thr
                325                 330                 335
Ile Ser Lys Thr Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Met Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445
```

<210> SEQ ID NO 116
<211> LENGTH: 645
<212> TYPE: DNA
<213> ORGANISM: Homo sapiens

<400> SEQUENCE: 116

| | | | | | |
|---|---|---|---|---|---|
| gaaatagtga | tgacgcagtc | tccagccacc | ctgtctgtgt | ctccagggga | aagagccacc | 60 |
| ctctcctgca | gggccagtca | gagtgttagt | agcaacttag | cctggtacca | gcagaaacct | 120 |
| ggccaggctc | ccaggctcct | catctatggt | gcatccacca | gggccactgg | tatcccagcc | 180 |

```
aggttcagtg gcagtgggtc tgggacagag ttcactctca ccatcagcag cctgcagtct    240
gaagattttg cagtttatta ctgtcagcag tataataact ggccgctcac tttcggcgga    300
gggaccaagg tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                   645
```

<210> SEQ ID NO 117
<211> LENGTH: 214
<212> TYPE: PRT
<213> ORGANISM: Homo sapiens

<400> SEQUENCE: 117

```
Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
     50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 118
<211> LENGTH: 122
<212> TYPE: PRT
<213> ORGANISM: Homo sapiens

<400> SEQUENCE: 118

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Phe
             20                  25                  30
```

```
Ala Met Ser Trp Val Arg Gln Ala Pro Gly Lys Gly Leu Glu Trp Val
             35                  40                  45

Ser Thr Ile Ser Gly Ser Gly Gly Tyr Thr Phe Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gly Arg Tyr Asn Trp Asn Tyr Gly Ala Phe Asp Ile Trp
             100                 105                 110

Gly Gln Gly Thr Met Val Thr Val Ser Ser
            115                 120

<210> SEQ ID NO 119
<211> LENGTH: 367
<212> TYPE: DNA
<213> ORGANISM: Homo sapiens

<400> SEQUENCE: 119
gaggtgcagc tgttggagtc tgggggaggc ttggtacagc ctgggggtc cctgagactc      60 tcctgtgcag cctctggatt cacctttagc agctttgcca tgagctgggt ccgccaggct    120
ccagggaagg gctggaatg gtctcaact attagtggta gtggtggtta cacattctac      180
gcagactccg tgaagggccg gttcaccatc tccagagaca attccaagaa cacgctgtat   240
ctgcaaatga acagcctgag agccgaggac acggccgtat attactgtgc gaaagatgga    300
aggtataact ggaactacgg ggcttttgat atctggggcc aagggacaat ggtcaccgtc    360
tcctcag                                                              367

<210> SEQ ID NO 120
<211> LENGTH: 107
<212> TYPE: PRT
<213> ORGANISM: Homo sapiens

<400> SEQUENCE: 120

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Leu
                 85                  90                  95

Thr Phe Gly Gly Gly Thr Lys Val Glu Ile Lys
            100                 105

<210> SEQ ID NO 121
<211> LENGTH: 322
<212> TYPE: DNA
<213> ORGANISM: Homo sapiens
```

-continued

```
<400> SEQUENCE: 121
gaaatagtga tgacgcagtc tccagccacc ctgtctgtgt ctccagggga aagagccacc      60
ctctcctgca gggccagtca gagtgttagt agcaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcag tataataact ggccgctcac tttcggcgga     300
gggaccaagg tggagatcaa ac                                              322

<210> SEQ ID NO 122
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Gly Gly Gly Ser Gly Gly Gly Gly Ser Gly Gly Gly Gly Ser
 1               5                  10                  15
```

US 7,807,159 B2

ANTIBODIES TO MYOSTATIN

This application claims priority under 35 U.S.C. §119(e) from U.S. provisional application 60/674,933, filed on Apr. 25, 2005.

BACKGROUND OF THE INVENTION

A growing body of evidence indicates that myostatin (mstn, Growth and Differentiation Factor-8, or GDF-8) negatively regulates skeletal muscle growth. For example, a myostatin null mutation in a child has been associated with dramatic muscle hypertrophy without any obvious abnormalities (Schuelke et al. (2004) Myostatin Mutation Associated with Gross Muscle Hypertrophy in a Child. *New Engl. J. Med.* 350:2682-8). A negative correlation between muscle myostatin protein levels and skeletal muscle mass has also been demonstrated (Schulte, J. N. and Yarasheski, K. E. (2001). Effects of resistance training on the rate of muscle protein synthesis in frail elderly people. *Int. J. Sport Nutr. Exerc. Metab.* 11 Suppl:S111-820; Walker K S et al. (2004) Resistance training alters plasma myostatin but not IGF-1 in healthy men. *Med Sci Sports Exerc.* 36(5):787-93.). For example, there is an increased expression of muscle myostatin levels with age and increased myostatin expression has also been shown to contribute to muscle wasting in HIV-infected patients (Gonzalez-cadavid et al. (1998) Organization of the human myostatin gene and expression in healthy men and HIV-infected men with muscle wasting. *PNAS* 95:14938-4321). In addition, elevated myostatin levels are found in elderly populations. (Yarasheski K E et al., (2002) Serum myostatin-immunoreactive protein is increased in 60-92 year old women and men with muscle wasting. *J. Nutr. Health Aging.* 6(5):343-8). Myostatin also influences bone mass as myostatin-deficient mice have increased bone mineral density (Hamrick et al., (2003) Bone Architecture and Disc Degeneration in the Lumbar Spine of Mice Lacking GDF-8 (Myostatin). *J. Orthopaedic Res.* 21: 1025-1032 (and references therein).

Antibodies to circulating myostatin have been shown to cause increased muscle mass and improved glucose homeostasis in murine models of type 2 diabetes mellitus. Inhibition of myostatin by ip injection of a neutralizing antibody increases skeletal muscle mass, lowers fasting blood glucose and improves glucose sensitivity in obese diabetic mice (Li X. et al. (2002) Inhibition of myostatin increases muscle mass and improves glucose sensitivity in obese, diabetic mice. Poster #224, in Keystone Symposia: Diabetes Mellitus: Molecular Mechanisms, Genetics and New Therapies). In addition, $A^y/a$ mice are known to develop insulin resistance and are used as a model for type 2 diabetes. When $A^y/a$ mice are made devoid of myostatin by deletion of the myostatin locus, they have normal fed glucose and insulin levels, and dramatically lower glucose levels following an exogenous glucose load relative to normal $A^y/a$ mice (McPherron et al. (2002) *J. Clin. Invest.* 109:595-601).

Considering the detrimental muscle, bone and metabolic defects associated with myostatin, there is an urgent need for antibodies as therapeutics that are specific for myostatin and which prevent or treat conditions by reducing myostatin activity, as well as antibodies as diagnostics to identify individuals that are in need of treatment to reduce myostatin activity.

SUMMARY OF THE INVENTION

The invention provides anti-myostatin antibodies, nucleic acids encoding them, vectors and host cells for producing the antibodies, compositions and kits comprising the antibodies and methods of making and using the antibodies. Various embodiments of the invention described in the following numbered paragraphs include, but are not limited to those.

1. A human, chimeric or humanized monoclonal antibody or an antigen-binding portion thereof that specifically binds to myostatin.

2. The monoclonal antibody or antigen-binding portion according to paragraph 1 wherein the myostatin is human myostatin.

3. A monoclonal antibody or antigen-binding portion according to paragraph 1, wherein said antibody or portion selectively binds myostatin over GDF11 by at least 50-fold.

4. A monoclonal antibody or antigen-binding portion according to paragraph 3, wherein said antibody or portion inhibits myostatin binding to an activin type I or type II receptor.

5. A monoclonal antibody or antigen-binding portion according to paragraph 1, wherein the antibody or portion thereof has at least one property selected from the group consisting of:
   (a) competes for binding to myostatin with an antibody selected from the group consisting of 1_116_1; 1_136_3; 1_257_1; 1_46_1; 2_112_1; 1_314_1; 1_66_1; 2_43_1; 2_177_1; 1_132_1; 1_268_1; 2_112_K; 1_116_1L-Q45K; 1_257_1L-L21I; 1_314_1H-T92A; 1_46_1H-L81M; 2_112_1H-I12V; 2_112_1L-F58I; 2_112_1L-I85V; 2_112_1H-L81M, L-F58I; 2_112_1H-L81M, L-I85V; and 2_112_1H-L81M, L-F58I, I85V;
   (b) binds to the same epitope of myostatin as an antibody selected from the group consisting of 1_116_1; 1_136_3; 1_257_1; 1_46_1; 2_112_1; 1_314_1; 1_66_1; 2_43_1; 2_177_1; 1_132_1; 1_268_1; 2_112_K; 1_116_1L-Q45K; 1_257_1L-L21I; 1_314_1H-T92A; 1_46_1H-L81M; 2_112_1H-I12V; 2_112_1L-F58I; 2_112_1L-I85V; 2_112_1H-L81M, L-F58I; 2_112_1H-L81M, L-I85V; and 2_112_1H-L81M, L-F58I, I85V;
   (c) binds to myostatin with substantially the same $K_D$ as an antibody selected from the group consisting of 1_116_1; 1_136_3; 1_257_1; 1_46_1; 2_112_1; 1_314_1; 1_66_1; 2_43_1; 2_177_1; 1_132_1; 1_268_1; 2_112_K; 1_116_1L-Q45K; 1_257_1L-L21I; 1_314_1H-T92A; 1_46_1H-L81M; 2_112_1H-I12V; 2_112_1L-F58I; 2_112_1L-I85V; 2_112_1H-L81M, L-F58I; 2_112_1H-L81M, L-I85V; and 2_112_1H-L81M, L-F58I, I85V; and
   (d) binds to myostatin with substantially the same off rate as an antibody selected from the group consisting of 1_116_1; 1_136_3; 1_257_1; 1_46_1; 2_112_1; 1_314_1; 1_66_1; 2_43_1; 2_177_1; 1_132_1; 1_268_1; 2_112_K; 1_116_1L-Q45K; 1_257_1L-L21I; 1_314_$_1$H-T92A; 1_46_1H-L81M; 2_112_1H-I12V; 2_112_1L-F58I; 2_112_1L-I85V; 2_112_1H-L81M, L-F58I; 2_112_1H-L81M, L-I85V; and 2_112_$_1$H-L81M, L-F58I, I85V.

6. A monoclonal antibody or antigen-binding portion thereof comprising:
   (a) a CDR set, CDR1, CDR2, and CDR3, that sequentially together are at least 90% identical in amino acid sequence to heavy chain CDRs, CDR1, CDR2, and CDR3, sequentially together, that are included in the amino acid sequence set forth in any one of SEQ ID NOs: 45, 49, 53, 57, 61, 65, 69, 73, 77, 81, 85 and 118;
   (b) a CDR set, CDR1, CDR2, and CDR3, that sequentially together are at least 90% identical in amino acid sequence to light chain CDRs, CDR1, CDR2, and CDR3, sequentially together, that are included in the amino acid sequence set forth in any one of SEQ ID NOs: 47, 51, 55, 59, 63, 67, 71, 75, 83, 87 and 120; or (c) a first CDR set of (a) and a second CDR set of (b).

7. A monoclonal antibody or antigen-binding portion thereof according to paragraph 1, wherein said antibody comprises heavy chain CDRs CDR1, CDR2, and CDR3, that sequentially together are at least 90% identical in amino acid sequence to heavy chain CDRs, CDR1, CDR2, and CDR3, sequentially together, that are included in the amino acid sequence set forth in any one of SEQ ID NOs: 45, 49, 53, 57, 61, 65, 69, 73, 77, 81, 85 and 118.

8. A monoclonal antibody or antigen-binding portion thereof according to paragraph 1, wherein said antibody comprises light chain CDRs CDR1, CDR2, and CDR3, that sequentially together are at least 90% identical in amino acid sequence to light chain CDRs, CDR1, CDR2, and CDR3, sequentially together, that are included in the amino acid sequence set forth in any one of SEQ ID NOs: 47, 51, 55, 59, 63, 67, 71, 75, 83, 87 and 120.

9. A monoclonal antibody or antigen-binding portion according to paragraph 1, wherein said antibody or antigen-binding portion comprises the heavy chain CDR1, CDR2 and CDR3 sequences found in any one of SEQ ID NOs: 45, 49, 53, 57, 61, 65, 69, 73, 77, 81, 85 or 118.

10. A monoclonal antibody or antigen-binding portion according to paragraph 1, wherein said antibody or antigen-binding portion comprises the light chain CDR1, CDR2 and CDR3 sequences found in any one of SEQ ID NOs: 47, 51, 55, 59, 63, 67, 71, 75, 79, 83, 87 or 120.

11. A monoclonal antibody or antigen-binding portion according to paragraph 1, wherein said antibody or portion comprises a heavy chain that utilizes a human $V_H$ 1-02 gene, a human $V_H$ 3-21 gene or a human $V_H$ 3-23 gene.

12. A monoclonal antibody or an antigen-binding portion according to paragraph 1, wherein said antibody or portion comprises a light chain that utilizes a human $V_K$ L2 gene, a human $V_K$ A3 gene or a human $V_K$ A30 gene.

13. A monoclonal antibody according to paragraph 1 comprising a $V_H$ domain at least 90% identical in amino acid sequence to the $V_H$ domain in any one of SEQ ID NOs: 2, 6, 10, 14, 18, 22, 26, 30, 34, 38, 42 or 115.

14. A monoclonal antibody according to paragraph 1 comprising a $V_L$ domain at least 90% identical in amino acid sequence to the $V_L$ domain in any one of SEQ ID NOs: 4, 8, 12, 16, 20, 24, 28, 32, 36, 40, 44 or 117.

15. A monoclonal antibody or an antigen-binding portion according to paragraph 1 that specifically binds myostatin, wherein:

(a) the heavy chain comprises the heavy chain CDR1, CDR2 and CDR3 amino acid sequences of an antibody selected from the group consisting of: 1__116__1; 1__136__3; 1__257__1; 1__46__1; 2__112__1; 1__314__1; 1__66__1; 2__43__1; 2__177__1; 1__132__1; 1__268__1; 2__112__K; 1__116__1L-Q45K; 1__257__1L-L21I; 1__314__1H-T92A; 1__46__1H-L81M; 2__112__1H-I12V; 2__112__1L-F58I; 2__112__1L-I85V; 2__112__1H-L81M, L-F58I; 2__112__1H-L81M, L-I85V; and 2__112__1H-L81M, L-F58I, I85V;

(b) the light chain comprises the light chain CDR1, CDR2 and CDR3 amino acid sequences of an antibody selected from the group consisting of 1__116__1; 1__136__3; 1__257__1; 1__46__1; 2__112__1; 1__314__1; 1__66__1; 2__43__1; 2__177__1; 1__132__1; 1__268__1; 2__112__K; 1__116__1L-Q45K; 1__257__1L-L21I; 1__314__1H-T92A; 1__46__1H-L81M; 2__112__1H-I12V; 2__112__1L-F58I; 2__112__1L-I85V; 2__112__1H-L81M, L-F58I; 2__112__1H-L81M, L-I85V; and 2__112__1H-L81M, L-F58I, I85V; or (c) the antibody comprises a heavy chain of (a) and a light chain of (b).

16. A monoclonal antibody according to paragraph 12 further comprising a $V_L$ domain at least 90% identical in amino acid sequence to the variable domain in any one of SEQ ID NOs: 4, 8, 12, 16, 20, 24, 28, 32, 36, 40, 44 or 117.

17. A monoclonal antibody selected from the group consisting of:

(a) an antibody comprising the amino acid sequences set forth in SEQ ID NO: 2 and SEQ ID NO: 4.
(b) an antibody comprising the amino acid sequences set forth in SEQ ID NO: 6 and SEQ ID NO: 8;
(c) an antibody comprising the amino acid sequences set forth in SEQ ID NO: 10 and SEQ ID NO: 12;
(d) an antibody comprising the amino acid sequences set forth in SEQ ID NO: 14 and SEQ ID NO: 16;
(e) an antibody comprising the amino acid sequences set forth in SEQ ID NO: 18 and SEQ ID NO: 20;
(f) an antibody comprising the amino acid sequences set forth in SEQ ID NO: 22 and SEQ ID NO: 24;
(g) an antibody comprising the amino acid sequences set forth in SEQ ID NO: 26 and SEQ ID NO: 28;
(h) an antibody comprising the amino acid sequences set forth in SEQ ID NO: 30 and SEQ ID NO: 32;
(i) an antibody comprising the amino acid sequences set forth in SEQ ID NO: 34 and SEQ ID NO: 36;
(j) an antibody comprising the amino acid sequences set forth in SEQ ID NO: 38 and SEQ ID NO: 40;
(k) an antibody comprising the amino acid sequences set forth in SEQ ID NO: 42 and SEQ ID NO: 44; and
(l) an antibody comprising the amino acid sequences set forth in SEQ ID NO: 115 and SEQ ID NO: 117.

18. A monoclonal antibody or antigen-binding portion thereof selected from the group consisting of:

(a) an antibody or antigen-binding portion comprising the variable domain amino acid sequences set forth in SEQ ID NO: 2 and SEQ ID NO: 4.
(b) an antibody or antigen-binding portion comprising the variable domain amino acid sequences set forth in SEQ ID NO: 6 and SEQ ID NO: 8;
(c) an antibody or antigen-binding portion comprising the variable domain amino acid sequences set forth in SEQ ID NO: 10 and SEQ ID NO: 12;
(d) an antibody or antigen-binding portion comprising the variable domain amino acid sequences set forth in SEQ ID NO: 14 and SEQ ID NO: 16;
(e) an antibody or antigen-binding portion comprising the variable domain amino acid sequences set forth in SEQ ID NO: 18 and SEQ ID NO: 20;
(f) an antibody or antigen-binding portion comprising the variable domain amino acid sequences set forth in SEQ ID NO: 22 and SEQ ID NO: 24;
(g) an antibody or antigen-binding portion comprising the variable domain amino acid sequences set forth in SEQ ID NO: 26 and SEQ ID NO: 28;
(h) an antibody or antigen-binding portion comprising the variable domain amino acid sequences set forth in SEQ ID NO: 30 and SEQ ID NO: 32;
(i) an antibody or antigen-binding portion comprising the variable domain amino acid sequences set forth in SEQ ID NO: 34 and SEQ ID NO: 36;
(j) an antibody or antigen-binding portion comprising the variable domain amino acid sequences set forth in SEQ ID NO: 38 and SEQ ID NO: 40;

(k) an antibody or antigen-binding portion comprising the variable domain amino acid sequences set forth in SEQ ID NO: 42 and SEQ ID NO: 44; and (l) an antibody or antigen-binding portion comprising the variable domain amino acid sequences set forth in SEQ ID NO: 115 and SEQ ID NO: 117.

19. A monoclonal antibody or antigen-binding portion thereof comprising a first CDR sequence set comprising a first CDR1, first CDR2 and first CDR3 and a second CDR sequence set comprising a second CDR1, second CDR2 and second CDR3, wherein said first CDR set and said second CDR set each sequentially together have at least 90% identity to the CDR1, CDR2 and CDR3 sequences, sequentially together, of:
  (a) SEQ ID NO: 2 and SEQ ID NO: 4, respectively;
  (b) SEQ ID NO: 6 and SEQ ID NO: 8, respectively;
  (c) SEQ ID NO:10 and SEQ ID NO:12, respectively;
  (d) SEQ ID NO:14 and SEQ ID NO:16, respectively;
  (e) SEQ ID NO:18 and SEQ ID NO:20, respectively;
  (f) SEQ ID NO:22 and SEQ ID NO:24, respectively;
  (g) SEQ ID NO:26 and SEQ ID NO:28, respectively;
  (h) SEQ ID NO:30 and SEQ ID NO:32, respectively;
  (i) SEQ ID NO:34 and SEQ ID NO:36, respectively;
  (j) SEQ ID NO:38 and SEQ ID NO:40, respectively;
  (k) SEQ ID NO:42 and SEQ ID NO:44, respectively; and
  (l) SEQ ID NO:115 and SEQ ID NO:117, respectively.

20. A monoclonal antibody or antigen-binding portion thereof comprising a first CDR sequence set comprising a first CDR1, first CDR2 and first CDR3 and a second CDR sequence set comprising a second CDR1, second CDR2 and second CDR3, wherein said first CDR set and said second CDR set are each the CDR1, CDR2 and CDR3 sequences, sequentially together, of
  (a) SEQ ID NO: 2 and SEQ ID NO: 4, respectively;
  (b) SEQ ID NO: 6 and SEQ ID NO: 8, respectively;
  (c) SEQ ID NO:10 and SEQ ID NO:12, respectively;
  (d) SEQ ID NO:14 and SEQ ID NO:16, respectively;
  (e) SEQ ID NO:18 and SEQ ID NO:20, respectively;
  (f) SEQ ID NO:22 and SEQ ID NO:24, respectively;
  (g) SEQ ID NO:26 and SEQ ID NO:28, respectively;
  (h) SEQ ID NO:30 and SEQ ID NO:32, respectively;
  (i) SEQ ID NO:34 and SEQ ID NO:36, respectively;
  (k) SEQ ID NO:38 and SEQ ID NO:40, respectively;
  (l) SEQ ID NO:42 and SEQ ID NO:44, respectively; and
  (m) SEQ ID NO:115 and SEQ ID NO:117, respectively.

21. A monoclonal antibody that specifically binds myostatin comprising the heavy chain amino acid sequence set forth in SEQ ID NO:115 and the light chain amino acid sequence set forth in SEQ NO:117.

22. A monoclonal antibody or an antigen-binding portion thereof comprising the variable regions contained in SEQ ID NO:115 and SEQ ID NO:117.

23. A monoclonal antibody or an antigen-binding portion thereof, that specifically binds myostatin comprising CDRs CDR1, CDR2, and CDR3 contained in SEQ ID NO:115 and SEQ ID NO:117.

24. A monoclonal antibody or an antigen-binding portion thereof said monoclonal antibody or antigen-binding portion binds to peptide 1 and peptide 5 portions of myostatin, wherein peptide 1 comprises the amino acid sequence of SEQ ID NO: 103 and peptide 5 comprises the amino acid sequence of SEQ ID NO: 107.

25. An antibody produced by a cell having ATCC Deposit Designation Number selected from the group consisting of PTA-6566, PTA-6567, PTA-6568, PTA-6569, PTA-6570, PTA-6571, PTA-6572, PTA-6573, PTA-6574, PTA-6575, and PTA-6576.

26. A pharmaceutical composition comprising an antibody or an antigen-binding portion according to any one of paragraphs 1 to 25 and a pharmaceutically acceptable carrier.

27. A pharmaceutical composition according to paragraph 26, further comprising at least one therapeutic agent.

28. A method comprising the step of administering to said subject an antibody or an antigen-binding portion according to any one of paragraphs 1 to 25 or the pharmaceutical composition according to paragraph 26, wherein said antibody, antigen-binding portion or pharmaceutical composition inhibits myostatin activity, wherein said subject is in need of increasing muscle mass, promoting skeletal muscle development, treating a muscle wasting disorder or enhancing skeletal muscle growth.

29. An isolated cell line that produces an antibody or an antigen-binding portion according to any one of paragraphs 1 to 25 or the heavy chain or light chain of said antibody or said antigen-binding portion.

30. An isolated nucleic acid molecule comprising a nucleotide sequence that encodes the heavy chain or an antigen-binding portion thereof or the light chain or an antigen-binding portion thereof of an antibody according to any one of paragraphs 1 to 25.

31. A vector comprising the nucleic acid molecule according to paragraph 30 wherein the vector optionally comprises an expression control sequence operably linked to the nucleic acid molecule.

32. A host cell comprising the vector according to paragraph 31 or the nucleic acid molecule according to paragraph 30.

33. A method for producing an anti-myostatin antibody or an antigen-binding portion thereof, comprising culturing the host cell according to paragraph 32 or the cell line according to paragraph 29 under suitable conditions and recovering said antibody or antigen-binding portion.

34. A non-human transgenic organism carrying the nucleic acid according to paragraph 30 either chromosomally or extrachromasomally, wherein the non-human transgenic organism expresses said nucleic acid.

35. A method for isolating an antibody or an antigen-binding portion thereof that specifically binds to myostatin, comprising the step of isolating the antibody from the non-human transgenic organism according to paragraph 34.

36. A method for treating a subject in need thereof with an antibody or an antigen-binding portion thereof that specifically binds to myostatin comprising the steps of:
  (a) administering to said subject an effective amount of an isolated nucleic acid molecule according to paragraph 30; and
  (b) expressing said nucleic acid molecule.

37. A method for producing a human monoclonal antibody that specifically binds to myostatin, comprising the steps of:
  (a) immunizing a non-human transgenic animal that is capable of producing human antibodies with myostatin, an immunogenic portion of myostatin, or a cell or tissue expressing myostatin;
  (b) allowing the non-human transgenic animal to mount an immune response to myostatin;
  (c) isolating B lymphocytes from the non-human transgenic animal; and
  (d) isolating a monoclonal antibody that specifically binds to myostatin from said isolated B lymphocytes.

38. An isolated antibody produced by the method according to paragraph 37.

39. A method for inhibiting the binding of myostatin to cells expressing an activin Type II or IIB receptor comprising contacting the myostatin with an antibody or antigen-binding portion according to any one of paragraphs 1 to 25, wherein said antibody or antigen-binding portion inhibits myostatin activity.

40. A method for increasing myoblast proliferation comprising contacting a composition comprising myoblasts and myostatin with an antibody or antigen-binding portion according to any one of paragraphs 1 to 25, wherein said antibody or antigen-binding portion inhibits myostatin activity.

41. A method comprising administering to a subject an antibody or an antigen-binding portion thereof according to any one of paragraphs 1 to 25, wherein said antibody or antigen-binding portion inhibits myostatin activity, wherein said subject is in need of improving glucose homeostasis, decreasing fat mass, increasing insulin sensitivity, improving kidney function, decreasing fat accumulation, treating, preventing or inhibiting a disease or condition characterized by bone loss, said disease or condition including osteoporosis, osteopenia, osteoarthritis and bone fractures, treating metabolic syndrome, or counteracting muscle wasting from sustained administration of a glucocorticoid or a steroid hormone during the time that said subject is undergoing treatment with a glucocorticoid or a steroid hormone.

42. A method for reducing myostatin activity in a subject in need thereof comprising the step of administering to said subject a monoclonal antibody or an antigen-binding portion thereof according to any one of paragraphs 1 to 25, wherein said monoclonal antibody or antigen-binding portion inhibits myostatin activity.

43. A method for reversing age-related decline in muscle mass in a subject in need thereof comprising the step of administering to said subject an antibody or an antigen-binding portion according to any one of paragraphs 1 to 25, wherein said antibody or antigen-binding portion inhibits myostatin activity.

44. A method for increasing myoblast proliferation and differentiation in a subject in need thereof comprising the step of administering to said subject an antibody or antigen-binding portion according to any one of paragraphs 1 to 25, wherein said antibody or antigen-binding portion inhibits myostatin activity.

45. A method for reducing myostatin-induced activin type IIA or IIB membrane receptor mediated cell signalling in a subject in need thereof comprising the step of administering to said subject an antibody or an antigen-binding portion according to any one of paragraphs 1 to 25, wherein said antibody or antigen-binding portion inhibits myostatin activity.

46. A method for decreasing myostatin-mediated activation of an activin type I membrane receptor in a subject in need thereof comprising the step of administering to said subject an antibody or an antigen-binding portion according to any one of paragraphs 1 to 25, wherein said antibody or antigen-binding portion inhibits myostatin activity.

47. A method for reducing myostatin-mediated phosphorylation of one or more R-smad proteins selected from the group consisting of: Smad 2 and Smad 3 in a subject in need thereof comprising the step of administering to said subject an antibody or antigen-binding portion according to any one of paragraphs 1 to 18, wherein said antibody or antigen-binding portion inhibits myostatin activity.

48. A method for increasing expression of a gene selected from the group consisting of: myoD, myf5 and myogenin, in a subject in need thereof comprising the step of administering to said subject an antibody or antigen-binding portion according to any one of paragraphs 1 to 25, wherein said antibody or antigen-binding portion inhibits myostatin activity.

49. A method for promoting muscle growth, weight gain or aiding in the prevention of frailty in cattle, swine, sheep, chickens, turkeys, horses, fish, dogs and cats in need thereof comprising the step of administering to said subject an antibody or antigen-binding portion according to any one of paragraphs 1 to 25, wherein said antibody or antigen-binding portion inhibits myostatin activity.

50. A monoclonal antibody or antigen binding portion thereof selected from the group consisting of:
  (a) an antibody or antigen binding portion thereof comprising the variable domain amino acid sequences set forth in SEQ ID NO: 45 and SEQ ID NO:47;
  (b) an antibody or antigen binding portion thereof comprising the variable domain amino acid sequences set forth in SEQ ID NO:49 and SEQ ID NO:51;
  (c) an antibody or antigen binding portion thereof comprising the variable domain amino acid sequences set forth in SEQ ID NO: 53 and SEQ ID NO:55;
  (d) an antibody or antigen binding portion thereof comprising the variable domain amino acid sequences set forth in SEQ ID NO:57 and SEQ ID NO:59;
  (e) an antibody or antigen binding portion thereof comprising the variable domain amino acid sequences set forth in SEQ ID NO:61 and SEQ ID NO:63;
  (f) an antibody or antigen binding portion thereof comprising the variable domain amino acid sequences set forth in SEQ ID NO:65 and SEQ ID NO:67;
  (g) an antibody or antigen binding portion thereof comprising the variable domain amino acid sequences set forth in SEQ ID NO:69 and SEQ ID NO:71;
  (h) an antibody or antigen binding portion thereof comprising the variable domain amino acid sequences set forth in SEQ ID NO:73 and SEQ ID NO:75;
  (i) an antibody or antigen binding portion thereof comprising the variable domain amino acid sequences set forth in SEQ ID NO:77 and SEQ ID NO:79;
  (j) an antibody or antigen binding portion thereof comprising the variable domain amino acid sequences set forth in SEQ ID NO:81 and SEQ ID NO:83; and
  (k) an antibody or antigen binding portion thereof comprising the variable domain amino acid sequences set forth in SEQ ID NO:85 and SEQ ID NO:87; and
  (l) an antibody or antigen binding portion thereof comprising the variable domain amino acid sequences set forth in SEQ ID NO: 118 and SEQ ID NO:120.

51. A method of treating metabolic syndrome in a subject in need thereof comprising the step of administering to said subject an antibody or antigen-binding portion according to any one of paragraphs 1 to 25, wherein said antibody or antigen-binding portion inhibits myostatin activity.

52. A mammalian host cell line comprising polynucleotides encoding the heavy and light chains of a human, chimeric or humanized monoclonal antibody that competes for binding to myostatin with an antibody or an antigen-binding portion thereof, wherein the antibody or portion thereof has at least one property selected from the group consisting of:
  (a) competes for binding to myostatin with an antibody selected from the group consisting of 1_116_1; 1_136_3; 1_257_1; 1_46_1; 2_112_1; 1_314_1; 1_66_1; 2_43_1; 2_177_1; 1_132_1; 1_268_1; 2_112_K; 1_116_1L-Q45K; 1_257_1L-L21I; 1_314_1H-T92A; 1_46_1H-L81M; 2_112_1H-I12V; 2_112_1L-F58I; 2_112_1L-I85V; 2_112_1H-L81M, L-F58I; 2_112_1H-L81M, L-I85V; and 2_112_1H-L81M, L-F58I, I85V;
  (b) binds to the same epitope of myostatin as an antibody selected from the group consisting of 1_116_1; 1_136_3;

1_257_1; 1_46_1; 2_112_1; 1_314_1; 1_66_1; 2_43_1; 2_177_1; 1_132_1; 1_268_1; 2_112_K; 1_116_1L-Q45K; 1_257_1L-L21I; 1_314_1H-T92A; 1_46_1H-L81M; 2_112_1H-I12V; 2_112_1L-F58I; 2_112_1L-I85V; 2_112_1H-L81M, L-F58I; 2_112_1H-L81M, L-I85V; and 2_112_1H-L81M, L-F58I, I85V;

(c) binds to myostatin with substantially the same $K_D$ as an antibody selected from the group consisting of 1_116_1; 1_136_3; 1_257_1; 1_46_1; 2_112_1; 1_314_1; 1_66_1; 2_43_1; 2_177_1; 1_132_1; 1_268_1; 2_112_K; 1_116_1L-Q45K; 1_257_1L-L21I; 1_314_1H-T92A; 1_46_1H-L81M; 2_112_1H-I12V; 2_112_1L-F58I; 2_112_1L-I85V; 2_112_1H-L81M, L-F58I; 2_112_1H-L81M, L-I85V; and 2_112_1H-L81M; L-F58I, I85V; and (d) binds to myostatin with substantially the same off rate as an antibody selected from the group consisting of 1_116_1; 1_136_3; 1_257_1; 1_46_1; 2_112_1; 1_314_1; 1_66_1; 2_43_1; 2_177_1; 1_132_1; 1_268_1; 2_112_K; 1_116_1L-Q45K; 1_257_1L-L21I; 1_314_1H-T92A; 1_46_1H-L81M; 2_112_1H-I12V; 2_112_1L-F58I; 2_112_1L-I85V; 2_112_1H-L81M, L-F58I; 2_112_1H-L81M, L-I85V; and 2_112_1H-L81M; L-F58I, I85V.

53. A mammalian host cell line comprising polynucleotides encoding the heavy and light chains of a monoclonal antibody or antigen-binding portion thereof that competes for binding to myostatin with an antibody comprising:
   (a) a heavy chain that utilizes a human $V_H$ 1-02 gene, a human $V_H$ 3-21 gene or a human $V_H$ 3-23 gene; and
   (b) a light chain that utilizes a human $V_K$ L2 gene, a human $V_K$ A3 gene or a human $V_K$ A30 gene.

54. A mammalian host cell line comprising polynucleotides encoding the heavy and light chains of a monoclonal antibody or an antigen-binding portion of said monoclonal antibody having the same amino acid sequence as the antibody produced by a hybridoma cell line having ATCC Deposit Designation Number selected from the group consisting of PTA-6566, PTA-6567, PTA-6568, PTA-6569, PTA-6570, PTA-6571, PTA-6572, PTA-6573, PTA-6574, PTA-6575, and PTA-6576.

55. A mammalian host cell line comprising polynucleotides encoding an antibody having the same amino acid sequence as the antibody produced by a hybridoma cell having an ATCC Deposit Designation Number selected from the group consisting of PTA-6566, PTA-6567, PTA-6568, PTA-6569, PTA-6570, PTA-6571, PTA-6572, PTA-6573, PTA-6574, PTA-6575, and PTA-6576.

56. A method comprising expressing said human monoclonal antibody in said mammalian host cell line of any one of paragraphs 52-55 and recovering said human monoclonal antibody.

57. A hybridoma cell line selected from the group consisting of ATCC Deposit Designation Numbers PTA-6566, PTA-6567, PTA-6568, PTA-6569, PTA-6570, PTA-6571, PTA-6572, PTA-6573, PTA-6574, PTA-6575, and PTA-6576

58. A mammalian host cell line comprising polynucleotides encoding the heavy and light chains of a human, chimeric or humanized monoclonal antibody, wherein the antibody or portion thereof has at least one property selected from the group consisting of:
   (a) competes for binding to myostatin with an antibody selected from the group consisting of: 1_116_1; 1_136_3; 1_257_1; 1_46_1; 2_112_1; 1_314_1; 1_66_1; 2_43_1; 2_177_1; 1_132_1; 1_268_1; 2_112_K; 1_116_1L-Q45K; 1_257_1L-L21I; 1_314_1H-T92A; 1_46_1H-L81M; 2_112_1H-I12V; 2_112_1L-F58I; 2_112_1L-I85V; 2_112_1H-L81M, L-F58I; 2_112_1H-L81M, L-I85V; and 2_112_1H-L81M, L-F58I, I85V;

(b) binds to the same epitope of myostatin as an antibody selected from the group consisting of: 1_116_1; 1_136_3; 1_257_1; 1_46_1; 2_112_1; 1_314_1; 1_66_1; 2_43_1; 2_177_1; 1_132_1; 1_268_1; 2_112_K; 1_116_1L-Q45K; 1_257_1L-L21I; 1_314_1H-T92A; 1_46_1H-L81M; 2_112_1H-I12V; 2_112_1L-F58I; 2_112_1L-I85V; 2_112_1H-L81M, L-F58I; 2_112_1H-L81M, L-I85V; and 2_112_1H-L81M, L-F58I, I85V;

(c) is an antibody having the same amino acid sequence as the antibody produced by a hybridoma cell having an ATCC Deposit Designation Number selected from the group consisting of PTA-6566, PTA-6567, PTA-6568, PTA-6569, PTA-6570, PTA-6571, PTA-6572, PTA-6573, PTA-6574, PTA-6575, and PTA-6576; and (d) is a hybridoma cell line selected from the group consisting of ATCC Deposit Designation Numbers PTA-6566, PTA-6567, PTA-6568, PTA-6569, PTA-6570, PTA-6571, PTA-6572, PTA-6573, PTA-6574, PTA-6575, and PTA-6576.

BRIEF DESCRIPTION OF THE DRAWINGS

FIG. 7 shows the amino acid sequences of peptides 1-11 and corresponding sequence identifiers (SEQ ID NOs 103-113).

FIG. 12 is a table summarizing in vitro assay data.

FIG. 13 is a table summarizing gene usage, epitope binning and peptide binding.

FIGS. 14 and 15 show the effects on muscle mass in mice following in vivo treatment with anti-myostatin antibodies as compared with vehicle for the gastrocnemius-pantaris-sloeus (GPS), tibialis anterior (TA) and quadriceps (Quads) muscles.

FIG. 18 is a dose (A) and concentration (B) response analysis of varying doses of an anti-myostatin antibody (2_112_K) and their effects on muscle weight.

FIG. 19 is an alignment of the heavy and light chain variable regions of antibodies 2_112_1 (heavy chain: SEQ ID NO:77; light chain: SEQ ID NO:79) and 2_112_K (heavy chain: SEQ ID NO:118; light chain: SEQ ID NO:120).

FIG. 20 show the effects on muscle mass (A) and adipose mass (B) in mice following in vivo treatment with cortisone with an anti-myostatin antibody (2_112_K) as compared with vehicle for the gastrocnemius-pantaris-sloeus (GPS), tibialis anterior (TA) and quadriceps (Quads) muscles (in 20A) and the inguinal, epididymal and abdominla fat pad masses (in 20B).

DETAILED DESCRIPTION OF THE INVENTION

Definitions and General Techniques

Figure 1:
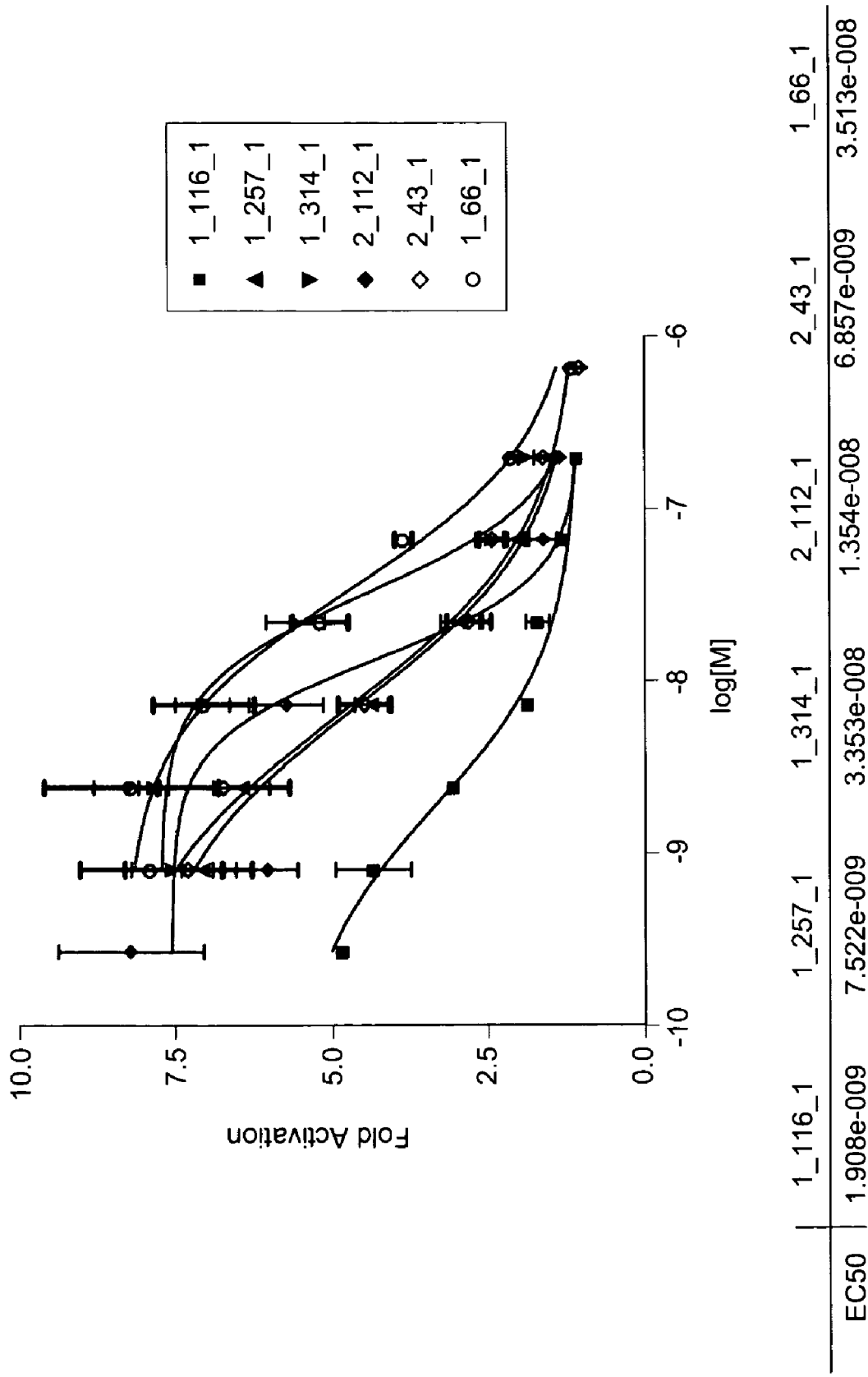
FIG. 1 shows the results of a myostatin responsive reporter gene assay. As shown, neutralizing anti-myostatin antibodies inhibit myostatin induced luciferase activity in A204 cells. Human antibody variants 1_116_1L-Q45K; 1_257-1L-L21I; 1_314_1H-T92A and 2_112_1H-I12V, L-F 58I, I85V inhibited luciferase activity to the same extent as wild type antibodies.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook et al. *Molecular Cloning: A Laboratory Manual* 2nd ed., Cold Spring Harbor Laboratory Press, Cold Spring Harbor, N.Y. (1989) and Ausubel et al., *Current Protocols in Molecular Biology*, Greene Publishing Associates (1992), and Harlow and Lane *Antibodies: A Laboratory Manual*, Cold Spring Harbor Laboratory Press, Cold Spring Harbor, N.Y. (1990), incorporated herein by reference. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following terms, unless otherwise indicated, shall be understood to have the following meanings:

The term "polypeptide" encompasses native or artificial proteins, protein fragments and polypeptide analogs of a protein sequence. A polypeptide may be monomeric or polymeric.

The term "isolated protein", "isolated polypeptide" or "isolated antibody" is a protein, polypeptide or antibody that by virtue of its origin or source of derivation (1) is not associated with naturally associated components that accompany it in its native state, (2) is free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

In various embodiments an isolated anti-myostatin antibody is one that has been protein A-purified (see, e.g., Example XVI), one that has been synthesized by a hybridoma or other cell line in vitro, and/or a human anti-myostatin antibody derived from a transgenic mouse.

A protein or polypeptide is "substantially pure," "substantially homogeneous," or "substantially purified" when at least about 60 to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "non-human transgenic organism" as used herein refers to any non-human transgenic individual living thing, including a non-human transgenic animal, plant, bacterium, protist, or fungus.

The term "polypeptide fragment" as used herein refers to a polypeptide that has an amino-terminal and/or carboxy-terminal deletion, but where the remaining amino acid sequence is identical to the corresponding positions in the naturally-occurring sequence. In some embodiments, fragments are at least 5, 6, 8 or 10 amino acids long. In other embodiments, the fragments are at least 14, at least 20, at least 50, or at least 70, 80, 90, 100, 150 or 200 amino acids long.

The term "polypeptide analog" as used herein refers to a polypeptide that comprises a segment that has substantial identity to a portion of an amino acid sequence and that has at least one of the following properties: (1) specific binding to myostatin under suitable binding conditions, (2) ability to inhibit or activate myostatin. Typically, polypeptide analogs comprise a conservative amino acid substitution (or insertion or deletion) with respect to the native sequence. Analogs typically are at least 20 or 25 amino acids long, preferably at least 50, 60, 70, 80, 90, 100, 150 or 200 amino acids long or longer, and can often be as long as a full-length polypeptide. Some embodiments of the invention include polypeptide fragments or polypeptide analog antibodies with 1, 2, 3, 4, 5, 6, 7, 8, 9, 10, 11, 12, 13, 14, 15, 16 or 17 substitutions from the germline amino acid sequence.

In certain embodiments, amino acid substitutions to an anti-myostatin antibody or antigen-binding portion thereof are those which: (1) reduce susceptibility to proteolysis, (2) reduce susceptibility to oxidation, (3) alter binding affinity for forming protein complexes, and (4) confer or modify other physicochemical or functional properties of such analogs, but still retain specific binding to myostatin. Analogs can include various muteins of a sequence other than the normally-occurring peptide sequence. For example, single or multiple amino acid substitutions, preferably conservative amino acid substitutions, may be made in the normally-occurring sequence, preferably in the portion of the polypeptide outside the domain(s) forming intermolecular contacts. A conservative amino acid substitution should not substantially change the structural characteristics of the parent sequence; e.g., a replacement amino acid should not alter the anti-parallel p-sheet that makes up the immunoglobulin binding domain that occurs in the parent sequence, or disrupt other types of secondary structure that characterizes the parent sequence. In general, glycine and proline would not be used in an anti-parallel β-sheet. Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et al., *Nature* 354:105 (1991), incorporated herein by reference.

Non-peptide analogs are commonly used in the pharmaceutical industry as drugs with properties analogous to those of the template peptide. These types of non-peptide compound are termed "peptide mimetics" or "peptidomimetics." Fauchere, *J. Adv. Drug Res.* 15:29 (1986); Veber and Freidinger, *TINS* p. 392 (1985); and Evans et al., *J. Med. Chem.* 30:1229 (1987), incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a desired biochemical property or pharmacological activity), such as a human antibody, but have one or more peptide linkages optionally replaced by a linkage selected from the group consisting of: —$CH_2NH$—, —$CH_2S$—, —$CH_2$—$CH_2$—, —$CH=CH$—(cis and trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch, *Ann. Rev. Biochem.* 61:387 (1992), incorporated herein by reference); for example, by adding internal cysteine residues capable of forming intramolecular disulfide bridges which cyclize the peptide.

Where an "antibody" is referred to herein with respect to the invention, it is normally understood that an antigen-binding portion thereof may also be used. An antigen-binding portion competes with the intact antibody for specific binding. See generally *Fundamental Immunology* Ch. 7 (Paul, W., ed., 2nd ed. Raven Press, N.Y. (1989)) (incorporated by reference in its entirety for all purposes). Antigen-binding portions may be produced by recombinant DNA techniques or by enzymatic or chemical cleavage of intact antibodies. In some embodiments, antigen-binding portions include Fab, Fab', F(ab')$_2$, Fd, Fv, dAb, and complementarity determining region (CDR) fragments, single-chain antibodies (scFv), chimeric antibodies, diabodies and polypeptides that contain at least a portion of an antibody that is sufficient to confer specific antigen binding to the polypeptide.

From N-terminus to C-terminus, both the mature light and heavy chain variable domains comprise, sequentially, the regions FR1, CDR1, FR2, CDR2, FR3, CDR3 and FR4.

The assignment of amino acids to each domain herein is in accordance with the definitions of Kabat *Sequences of Proteins of Immunological Interest* (National Institutes of Health, Bethesda, Md. (1987 and 1991)), Chothia & Lesk, *J. Mol. Biol.* 196:901-917 (1987) or Chothia et al., *Nature* 342:878-883 (1989).

As used herein, an antibody that is referred to by number is the same as a monoclonal antibody that is obtained from the hybridoma of the same number. For example, monoclonal antibody 2_112 is the same antibody as one obtained from hybridoma 2_112, or a subclone thereof, such as 2_112_1, 2_112_2, and the like. The only exception is 1_136_3 which is a different hybridoma from subclones 1_136_1 and 1_136_2.

As used herein, a Fd fragment means an antibody fragment that consists of the $V_H$ and $C_H1$ domains; an Fv fragment consists of the $V_L$ and $V_H$ domains of a single arm of an antibody; and a dAb fragment (Ward et al., *Nature* 341:544-546 (1989)) consists of a $V_H$ domain.

In some embodiments, the antibody is a single-chain antibody (scFv) in which $V_L$ and $V_H$ domains are paired to form a monovalent molecules via a synthetic linker that enables them to be made as a single protein chain. (Bird et al., *Science* 242:423-426 (1988) and Huston et al., *Proc. Natl. Acad. Sci. USA* 85:5879-5883 (1988).) In some embodiments, the antibodies are diabodies, i.e., are bivalent antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites. (See e.g., Holliger P. et al., *Proc. Natl. Acad. Sci. USA* 90:6444-6448 (1993), and Poljak R. J. et al., *Structure* 2:1121-1123 (1994).) In some embodiments, one or more CDRs from an antibody of the invention may be incorporated into a molecule either covalently or noncovalently to make it an immunoadhesin that specifically binds to myostatin. In such embodiments, the CDR(s) may be incorporated as part of a larger polypeptide chain, may be covalently linked to another polypeptide chain, or may be incorporated noncovalently. Further, the framework regions (FRs) may be derived from one of the anti-myostatin antibodies from which one or more of the CDRs are taken or from one or more different human antibodies.

In embodiments having one or more binding sites, the binding sites may be identical to one another or may be different.

As used herein, the term "human antibody" means any antibody in which the variable and constant domain sequences are human sequences. The term encompasses antibodies with sequences derived from (i.e., that utilize) human genes, but which have been changed, e.g. to decrease possible immunogenicity, increase affinity, eliminate cysteines that might cause undesirable folding, etc. The term encompasses such antibodies produced recombinantly in non-human cells, which might impart glycosylation not typical of human cells. These antibodies may be prepared in a variety of ways, as described below.

The term "chimeric antibody" as used herein means an antibody that comprises regions from two or more different antibodies. In one embodiment, one or more of the CDRs of the chimeric antibody are derived from a human anti-myostatin antibody. In another embodiment, all of the CDRs are derived from a human anti-myostatin antibodies. In another embodiment, the CDRs from more than one human anti-myostatin antibodies are combined in a chimeric antibody. For instance, a chimeric antibody may comprise a CDR1 from the light chain of a first human anti-myostatin antibody, a CDR2 from the light chain of a second human anti-myostatin antibody and a CDR3 from the light chain of a third human anti-myostatin antibody, and CDRs from the heavy chain may be derived from one or more other anti-myostatin antibodies. Further, the framework regions may be derived from one of the anti-myostatin antibodies from which one or more of the CDRs are taken or from one or more different human antibodies.

In some embodiments, a chimeric antibody of the invention is a humanized anti-myostatin antibody. A humanized anti-myostatin antibody of the invention comprises the amino acid sequence of one or more framework regions and/or the amino acid sequence from at least a portion of the constant region of one or more human anti-myostatin antibodies of the invention and further comprises sequences derived from a non-human anti-myostatin antibody, for example CDR sequences.

Fragments or analogs of antibodies or immunoglobulin molecules can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. See Bowie et al., *Science* 253:164 (1991).

The term "surface plasmon resonance", as used herein, refers to an optical phenomenon that allows for the analysis of real-time biospecific interactions by detection of alterations in protein concentrations within a biosensor matrix, for example using the BIACORE® system (Pharmacia Biosensor AB, Uppsala, Sweden and Piscataway, N.J.). For further descriptions, see Johnsson U. et al., *Ann. Biol. Clin.* 51:19-26 (1993); Jonsson U. et al., *Biotechniques* 11:620-627 (1991); Jonsson B. et al., *J. Mol. Recognit.* 8:125-131 (1995); and Johnsson B. et al., *Anal. Biochem.* 198:268-277 (1991).

The term "$K_D$" means the equilibrium dissociation constant of a particular antibody-antigen interaction.

The term "off rate" means the dissociation rate constant of a particular antibody-antigen interaction.

The term "epitope" includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. An epitope may be "linear" or "conformational." In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another. An antibody is said to specifically bind an antigen when the dissociation constant is $\leq 1$ mM, preferably $\leq 100$ nM and most preferably $\leq 10$ nM. In certain embodiments, the $K_D$ is 1 pM to 500 pM. In other embodiments, the $K_D$ is between 500 pM to 1 μM. In other embodiments, the $K_D$ is between 1 μM to 100 nM. In other embodiments, the $K_D$ is between 100 mM to 10 nM. Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, e.g., the antibodies compete for binding to the antigen. A high throughput process for "binning" antibodies based upon their cross-competition is described in International Patent Application No. WO 03/48731.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), incorporated herein by reference.

The term "polynucleotide" as referred to herein means a polymeric form of nucleotides of at least 10 bases in length, either ribonucleotides or deoxynucleotides or a modified form of either type of nucleotide. The term includes single and double stranded forms.

The term "isolated polynucleotide" as used herein means a polynucleotide of genomic, cDNA, or synthetic origin or some combination thereof, which by virtue of its origin the "isolated polynucleotide" (1) is not associated with all or a portion of a polynucleotides with which the "isolated polynucleotide" is found in nature, (2) is operably linked to a polynucleotide to which it is not linked in nature, or (3) does not occur in nature as part of a larger sequence.

The term "naturally occurring nucleotides" as used herein includes deoxyribonucleotides and ribonucleotides. The term "modified nucleotides" as used herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al., *Nucl. Acids Res.* 14:9081 (1986); Stec et al., *J. Am. Chem. Soc.* 106:6077 (1984); Stein et al., *Nucl. Acids Res.* 16:3209 (1988); Zon et al., *Anti-Cancer Drug Design* 6:539 (1991); Zon et al., *Oligonucleotides and Analogues: A Practical Approach*, pp. 87-108 (F. Eckstein, Ed., Oxford University Press, Oxford England (1991)); U.S. Pat. No. 5,151,510; Uhlmann and Peyman, *Chemical Reviews* 90:543 (1990), the disclosures of which are hereby incorporated by reference. An oligonucleotide can include a label for detection, if desired.

"Operably linked" sequences include both expression control sequences that are contiguous with the gene of interest and expression control sequences that act in trans or at a distance to control the gene of interest. The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, means a nucleic acid molecule capable of transporting another nucleic acid to which it has been linked. In some embodiments, the vector is a plasmid, i.e., a circular double stranded piece of DNA into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The term "recombinant host cell" (or simply "host cell"), as used herein, means a cell into which a recombinant expression vector has been introduced. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. "High stringency" or "highly stringent" conditions can be used to achieve selective hybridization conditions as known in the art and discussed herein. One example of "high stringency" or "highly stringent" conditions is the incubation of a polynucleotide with another polynucleotide, wherein one polynucleotide may be affixed to a solid surface such as a membrane, in a hybridization buffer of 6×SSPE or SSC, 50% formamide, 5×Denhardt's reagent, 0.5% SDS, 100 μg/ml denatured, fragmented salmon sperm DNA at a hybridization temperature of 42° C. for 12-16 hours, followed by twice washing at 55° C. using a wash buffer of 1×SSC, 0.5% SDS. See also Sambrook et al., supra, pp. 9.50-9.55.

The term "percent sequence identity" in the context of nucleic acid sequences means the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or BESTFIT®, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, *Methods Enzymol.* 183:63-98 (1990); Pearson, *Methods Mol. Biol.* 132:185-219 (2000); Pearson, *Methods Enzymol.* 266:227-258 (1996); Pearson, *J. Mol. Biol.* 276:71-84 (1998); incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

A reference to a nucleotide sequence encompasses its complement unless otherwise specified. Thus, a reference to a nucleic acid having a particular sequence should be understood to encompass its complementary strand, with its complementary sequence.

As used herein, the terms "percent sequence identity" and "percent sequence homology" are used interchangeably.

The term "substantial similarity" or "substantial sequence similarity," when referring to a nucleic acid or fragment thereof, means that when optimally aligned with appropriate nucleotide insertions or deletions with another nucleic acid (or its complementary strand), there is nucleotide sequence identity in at least about 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

As applied to polypeptides, the term "substantial identity" means that two peptide sequences, when optimally aligned, such as by the programs GAP or BESTFIT® using default gap weights as supplied with the programs, share at least 70%, 75% or 80% sequence identity, preferably at least 90% or 95% sequence identity, and more preferably at least 97%, 98% or 99% sequence identity. In certain embodiments, residue positions that are not identical differ by conservative amino acid substitutions. A "conservative amino acid substitution" is one in which an amino acid residue is substituted by another amino acid residue having a side chain R group with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity may be adjusted upwards to correct for the conservative nature of the substitution. Means for making this adjustment are well-known to those of skill in the art. See, e.g., Pearson, *Methods Mol. Biol.* 243:307-31 (1994). Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., *Science* 256:1443-45 (1992), incorporated herein by reference. A "moderately conservative" replacement is any change having a nonnegative value in the PAM250 log-likelihood matrix.

Sequence identity for polypeptides is typically measured using sequence analysis software. Protein analysis software matches sequences using measures of similarity assigned to various substitutions, deletions and other modifications, including conservative amino acid substitutions. For instance, GCG contains programs such as "Gap" and "BESTFIT®" which can be used with default parameters as specified by the programs to determine sequence homology or sequence identity between closely related polypeptides, such as homologous polypeptides from different species of organisms or between a wild type protein and a mutein thereof. See, e.g., GCG Version 6.1 (University of Wisconsin, WI). Polypeptide sequences also can be compared using FASTA using default or recommended parameters, see GCG Version 6.1. FASTA (e.g., FASTA2 and FASTA3) provides alignments and percent sequence identity of the regions of the best overlap between the query and search sequences (Pearson, *Methods Enzymol.* 183:63-98 (1990); Pearson, *Methods Mol. Biol.* 132:185-219 (2000)). Another preferred algorithm when comparing a sequence of the invention to a database containing a large number of sequences from different organisms is the computer program BLAST, especially blastp or tblastn, using default parameters as supplied with the programs. See, e.g., Altschul et al., *J. Mol. Biol.* 215:403-410 (1990); Altschul et al., *Nucleic Acids Res.* 25:3389-402 (1997).

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences.

As used herein, the terms "label" or "labeled" refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^{3}$H, $^{14}$C $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, TAXOL® (paclitaxel), cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

Throughout this specification and claims, the word "comprise," or variations such as "comprises" or "comprising," will be understood to imply the inclusion of a stated integer or group of integers but not the exclusion of any other integer or group of integers.

Human Anti-Myostatin Antibodies and Characterization Thereof

The invention herein provides anti-myostatin antibodies. In some embodiments, the antibodies are human. In other embodiments, the antibodies are humanized. In some embodiments, human anti-myostatin antibodies are produced by immunizing a non-human transgenic animal, e.g., a rodent, whose genome comprises human immunoglobulin genes so that the transgenic animal produces human antibodies.

An anti-myostatin antibody of the invention can comprise a human kappa or a human lambda light chain or an amino acid sequence derived therefrom. In some embodiments comprising a kappa light chain, the light chain variable domain ($V_L$) utilizes a human A30, A3 or L2 $V_K$ gene.

In some embodiments, the $V_L$ of the anti-myostatin antibody comprises one or more amino acid substitutions, deletions or insertions (additions) relative to the germline $V_K$ amino acid sequence. In some embodiments, the $V_L$ of the anti-myostatin antibody comprises 1, 2, 3, 4 or 5 amino acid substitutions relative to the germline $V_K$ amino acid sequence. In some embodiments, one or more of the substitutions from germline is in the CDR regions of the light chain. In some embodiments, the $V_K$ amino acid substitutions relative to germline are at one or more of the same positions as the substitutions relative to germline found in any one or more of the $V_L$ of the antibodies provided herein. For example, the $V_L$ of an anti-myostatin antibody of the invention may contain one or more of the amino acid substitutions compared to germline found in the $V_L$ of antibody 1_257_1. There also may be one or more amino acid substitutions compared to germline found in the $V_L$ of antibody 1_116_1, which utilizes the same $V_K$ gene as antibody 1_257_1. In some embodiments, the amino acid changes are at one or more of the same positions, but involve a different substitution than in the reference antibody. In all cases, the recitation of an antibody clone with dashes is equivalent to the same antibody clone with dots (e.g., 1_257_1=1.257.1).

In some embodiments, amino acid substitutions relative to germline occur at one or more of the same positions as substitutions from germline in any of the $V_L$ of antibodies 1_116_1, 1_136_3, 1_257_1, 1_46_1, 2_112_1, 1_314_1, 1_66_1, 2_43_1, 2_177_1, 1_132_1, 1_268_1, 1_116_1L-Q45K; 1_257_1L-L21I; 1_314_1H-T92A; 1_46_1H-L81M; 2_112_1H-I12V; 2_112_1L-F58I; 2_112_1L-I85V; 2_112_1H-L81M, L-F58I; 2_112_1H-L81M, L-I85V; or 2_112_1H-L81M, L-F58I, I85V, but the substitutions may represent conservative amino acid substitutions at such position(s) relative to the amino acid in the reference antibody. For example, if a particular position in one of these antibodies is changed relative to germline and is glutamate, one may substitute aspartate at that position. Similarly, if an amino acid substitution compared to germline in an exemplified antibody is serine, one may conservatively substitute threonine for serine at that position. Conservative amino acid substitutions are discussed supra, throughout this application.

In some embodiments, the anti-myostatin antibody comprises a light chain amino acid sequence selected from the group consisting of SEQ ID NOS: 4, 8, 12, 16, 20, 24, 28, 32, 36, 40 and 44. In other embodiments, the light chain comprises the light chain amino acid sequence of antibody 1_116_1L-Q45K; 1_257_1L-L21I; 2_112_1L-F58I; 2_112_1L-I85V or 2_112_1L-F58I, I85V. In some embodiments, the light chain of the human anti-myostatin antibody comprises the $V_L$ amino acid sequence of antibody 1_116_1 (SEQ ID NO: 4); 1_136_3 (SEQ ID NO: 12); 1_257_1 (SEQ ID NO: 16); 1_46_1 (SEQ ID NO: 24); 2_112_1 (SEQ ID NO: 28); 1_314_1 (SEQ ID NO: 20); 1_66_1 (SEQ ID NO: 36); 2_43_1 (SEQ ID NO: 44); 2_177_1 (SEQ ID NO: 40); 1_132_1 (SEQ ID NO: 8); or 1_268_1 (SEQ ID NO: 32) or said amino acid sequence having up to 1, 2, 3, 4 or 5 conservative amino acid substitutions and/or a total of up to 3 non-conservative amino acid substitutions. In other embodiments the light chain of the human anti-myostatin antibody comprises the $V_L$ amino acid sequence of antibody 1_116_1L-Q45K; 1_257_1L-L21I; 2_112_1L-F58I; 2_112_1L-I85V or 2_112_1L-F58I, I85V. In some embodiments, the light chain comprises the amino acid sequence from the beginning of the CDR1 to the end of the CDR3 of any one of the foregoing antibodies.

In some embodiments, the light chain may comprise the amino acid sequences of CDR1, CDR2 and CDR3 regions independently selected from the light chain CDR1, CDR2 and CDR3 regions, respectively, of two or more monoclonal antibodies selected from 1_116_1 (SEQ ID NO: 4); 1_136_3 (SEQ ID NO: 12); 1_257_1 (SEQ ID NO: 16); 1_46_1 (SEQ ID NO: 24); 2_112_1 (SEQ ID NO: 28); 1_314_1 (SEQ ID NO: 20); 1_66_1 (SEQ ID NO: 36); 2_43_1 (SEQ ID NO: 44); 2_177_1 (SEQ ID NO: 40); 1_132_1 (SEQ ID NO: 8); or 1_268_1 (SEQ ID NO: 32), or said CDR regions each having less than 3 or less than 2 conservative amino acid substitutions and/or a total of three or fewer non-conservative amino acid substitutions.

In certain embodiments, the light chain of the anti-myostatin antibody comprises the amino acid sequences of the light chain CDR1, CDR2 and CDR3 regions of an antibody selected from 1_116_1 (SEQ ID NO: 4); 1_136_3 (SEQ ID NO: 12); 1_257_1 (SEQ ID NO: 16); 1_46_1 (SEQ ID NO: 24); 2_112_1 (SEQ ID NO: 28); 1_314_1 (SEQ ID NO: 20); 1_66_1 (SEQ ID NO: 36); 2_43_1 (SEQ ID NO: 44); 2_177_1 (SEQ ID NO: 40); 1_132_1 (SEQ ID NO: 8); or 1_268_1 (SEQ ID NO: 32) or said CDR regions each having less than 3 or less than 2 conservative amino acid substitutions and/or a total of three or fewer non-conservative amino acid substitutions.

With regard to the heavy chain, in some embodiments, the variable domain ($V_H$) utilizes a human $V_H$1-02, $V_H$3-21 or $V_H$3-23 gene. In some embodiments, the $V_H$ sequence of the anti-myostatin antibody contains one or more amino acid substitutions, deletions or insertions (additions), collectively "mutations", relative to the germline $V_H$ amino acid sequence. In some embodiments, the variable domain of the heavy chain comprises 1, 2, 3, 4, 5, 6, 7, 8, 9, 10 or 11 mutations from the germline $V_H$ amino acid sequence. In some embodiments, the mutation(s) are non-conservative substitutions compared to the germline amino acid sequence. In some embodiments, the mutations are in the CDR regions of the heavy chain.

In some embodiments, amino acid substitutions are at one or more of the same positions as the substitutions from germline in any one or more of the $V_H$ of antibodies 1_116_1, 1_136_3, 1_257_1, 1_46_1, 2_112_1, 1_314_1, 1_66_1, 2_43_1, 2_177_1, 1_132_1, 1_268_1, 1_116_1L-Q45K; 1_257_1L-L21I; 1_314_1H-T92A; 1_46_1H-L81M; 2_112_1H-I12V; 2_112_1L-F58I; 2_112_1L-I85V; 2_112_1H-L81M, L-F58I; 2_112_1H-L81M, L-I85V; or 2_112_1H-L81M, L-F58I, I85V. In other embodiments, the amino acid changes are at one or more of the same positions but involve a different substitution than in the reference antibody.

In some embodiments, the heavy chain comprises an amino acid sequence selected from the group consisting of SEQ ID NOS: 2, 6, 10, 14, 18, 22, 26, 30, 34, 38 and 42. In other embodiments, the heavy chain comprises the heavy chain amino acid sequence of antibody 1_314_1H-T92A; 1_46_1H-L81M; or 2_112_1H-I12V. In some embodiments, the heavy chain comprises the $V_H$ amino acid sequence of antibody 1_116_1 (SEQ ID NO: 2), 1_136_3 (SEQ ID NO: 10), 1_257_1 (SEQ ID NO: 14), 1_46_1 (SEQ ID NO: 22), 2_112_1 (SEQ ID NO: 26), 1_314_1 (SEQ ID NO: 18), 1_66_1 (SEQ ID NO: 34), 2_43_1 (SEQ ID NO: 42), 2_177_1 (SEQ ID NO: 38), 1_132_1 (SEQ ID NO: 6) and 1_268_1 (SEQ ID NO: 30); or said $V_H$ amino acid sequence having up to 1, 2, 3, 4, 6, 8, 9, 10 or 11 conservative amino acid substitutions and/or a total of up to 3 non-conservative amino acid substitutions. In other embodiments, the heavy chain comprises the $V_H$ amino acid sequence of antibody 1_314_1H-T92A; 1_46_1H-L81M; or 2_112_1H-I12V. In some embodiments, the heavy chain comprises the amino acid sequence from the beginning of the CDR1 to the end of the CDR3 of any one of the foregoing antibodies.

In some embodiments, the heavy chain comprises the heavy chain CDR1, CDR2 and CDR3 regions of antibody 1_116_1, 1_136_3, 1_257_1, 1_46_1, 2_112_1, 1_314_1, 1_66_1, 2_43_1, 2_177_1, 1_132_1, 1_268_1, 1_116_1L-Q45K; 1_257_1L-L21I; 1_314_1H-T92A; 1_46_1H-L81M; 2_112_1H-I12V; 2_112_1L-F58I; 2_112_1L-I85V; 2_112_1H-L81M, L-F58I; 2_112_1H-L81M, L-I85V; or 2_112_1H-L81M, L-F58I, I85V or said CDR regions each having less than 8, less than 6, less than 4, or less than 3 conservative amino acid substitutions and/or a total of three or fewer non-conservative amino acid substitutions.

In some embodiments, the heavy chain CDR regions are independently selected from the CDR regions of two or more antibodies selected from antibodies 1_116_1, 1_136_3, 1_257_1, 1_46_1, 2_112_1, 1_314_1, 1_66_1, 2_43_1, 2_177_1, 1_132_1, 1_268_1, 1_116_1L-Q45K; 1_257_1L-L21I; 1_314_1H-T92A; 1_46_1H-L81M; 2_112_1H-I12V; 2_112_1L-F58I; 2_112_1L-I85V; 2_112_1H-L81M, L-F58I; 2_112_1H-L81M, L-I85V; or 2_112_1H-L81M, L-F58I, I85V. In another embodiment, the antibody comprises a light chain as disclosed above and a heavy chain as disclosed above. In a further embodiment, the light chain CDRs and the heavy chain CDRs are from the same antibody.

In various embodiments, the anti-myostatin antibodies have the full-length heavy chain and full length light chain amino acid sequence(s), the $V_H$ and $V_L$ amino acid sequences, the heavy chain CDR1, CDR2 and CDR3 and light chain CDR1, CDR2 and CDR3 amino acid sequences or the heavy chain amino acid sequence from the beginning of the CDR1 to the end of the CDR3 and the light chain amino acid sequence from the beginning of the CDR1 to the end of the CDR3 of an anti-myostatin antibody provided herein.

One type of amino acid substitution that may be made is to change one or more cysteines in the antibody, which may be chemically reactive, to another residue, such as, without limitation, alanine or serine. In one embodiment, there is a substitution of a non-canonical cysteine. The substitution can be made in a CDR or framework region of a variable domain or in the constant domain of an antibody. In some embodiments, the cysteine is canonical.

Another type of amino acid substitution that may be made is to remove potential proteolytic sites in the antibody. Such sites may occur in a CDR or framework region of a variable domain or in the constant domain of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues.

In some embodiments, the C-terminal lysine of the heavy chain of the anti myostatin antibody of the invention is cleaved. In various embodiments of the invention, the heavy and light chains of the anti-myostatin antibodies may optionally include a signal sequence.

In one aspect, the invention provides to eleven inhibitory human anti-myostatin monoclonal antibodies and the hybridoma cell lines that produce them. Table 1 lists the sequence identifiers (SEQ ID NOs) of the nucleic acids encoding the full-length heavy and light chains and variable domain containing portions of those chains, and the corresponding full-length deduced amino acid sequences.

TABLE 1

| | SEQUENCE IDENTIFIERS (SEQ ID NO) | | | | | | | |
|---|---|---|---|---|---|---|---|---|
| | FULL LENGTH | | | | V DOMAIN CONTAINING PORTION | | | |
| | Heavy | | Light | | Heavy | | Light | |
| Mab | DNA | PROTEIN | DNA | PROTEIN | PROTEIN | DNA | PROTEIN | DNA |
| 1_116_1 | 1 | 2 | 3 | 4 | 45 | 46 | 47 | 48 |
| 1_132_1 | 5 | 6 | 7 | 8 | 49 | 50 | 51 | 52 |
| 1_136_3 | 9 | 10 | 11 | 12 | 53 | 54 | 55 | 56 |
| 1_257_1 | 13 | 14 | 15 | 16 | 57 | 58 | 59 | 60 |
| 1_314_1 | 17 | 18 | 19 | 20 | 65 | 66 | 67 | 68 |
| 1_46_1 | 21 | 22 | 23 | 24 | 69 | 70 | 71 | 72 |
| 2_112_1 | 25 | 26 | 27 | 28 | 77 | 78 | 79 | 80 |
| 1_268_1 | 29 | 30 | 31 | 32 | 61 | 62 | 63 | 64 |
| 1_66_1 | 33 | 34 | 35 | 36 | 73 | 74 | 75 | 76 |
| 2_177_1 | 37 | 38 | 39 | 40 | 81 | 82 | 83 | 84 |
| 2_43_1 | 41 | 42 | 43 | 44 | 85 | 86 | 87 | 88 |
| 2_112_K | 114 | 115 | 116 | 117 | 118 | 119 | 120 | 121 |

The invention further provides heavy and/or light chain variants of certain of the above-listed human anti-myostatin antibodies, comprising one or more amino acid modifications. To designate the variants, the first letter is the one letter symbol for the amino acid of the naturally-occurring antibody chain, the number refers to the position of the amino acid (wherein position one is the N-terminal amino acid of the FR1), and the second letter is the one letter symbol for the variant amino acid.

The invention provides a light chain variant of monoclonal antibody 1_116_1 called 16_1L-Q45K, which has a lysine at position 45 of SEQ ID NO: 4.

Another light chain variant is 1_257_1L-L21I, which has an isoleucine residue at position 21 of SEQ ID NO: 16.

A heavy chain variant of monoclonal antibody of 1_314_1 called 1_314_1H-T92A which has an alanine residue at position 92 of SEQ ID NO: 18.

The invention further provides a heavy chain variant of monoclonal antibody 1_46_1 called 1_46_1H-L81M, which has a methionine at position 81 of SEQ ID NO: 22.

The invention provides a heavy chain variant (I12V) and two light chain variants (F58I and I85V) of monoclonal antibody 2_112_1. The heavy chain variant called 2_112_1H-I12V has a valine at position 12 of SEQ ID NO: 26. One light chain variant, 2_112_1L-F85I, has an isoleucine at position 85 of SEQ ID NO: 28. The other light chain variant, called 2_112_1L-I85V, has a valine at position 85 of SEQ ID NO: 28. The invention also provides a light chain variant comprising both mutations, i.e., 2_112_1L-F85I, I85V. The invention also includes antibodies comprising the heavy chain variant with either one or both of the light chain mutations, i.e., 2_112_1H-I12V, L-F58I; 2_112_1H-I12V, L-I85V; and 2_112_1H-I12V, L-F58I, I85V.

In still further embodiments, the invention includes antibodies comprising variable domain amino acid sequences with more than 80%, more than 85%, more than 90%, more than 95%, more than 96%, more than 97%, more than 98% or more than 99% sequence identity to a variable domain amino acid sequence of any of the above-listed human anti-myostatin antibodies Class and Subclass of Anti-Myostatin Antibodies The class and subclass of anti-myostatin antibodies may be determined by any method known in the art. In general, the class and subclass of an antibody may be determined using antibodies that are specific for a particular class and subclass of antibody. Such antibodies are commercially available. The class and subclass can be determined by ELISA, or Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

In some embodiments, the anti-myostatin antibody is a monoclonal antibody. The anti-myostatin antibody can be an IgG, an IgM, an IgE, an IgA, or an IgD molecule. In a preferred embodiment, the anti-myostatin antibody is an IgG and is an IgG1, IgG2, IgG3, IgG4 subclass. In another preferred embodiment, the antibody is subclass IgG2.

Identification of Myostatin Epitopes Recognized by Anti-Myostatin Antibodies

The invention provides a human anti-myostatin monoclonal antibody that binds to myostatin and competes or cross-competes with and/or binds the same epitope as: (a) an antibody selected from 1_116_1, 1_136_3, 1_257_1, 1_46_1, 2_112_1, 1_314_1, 1_66_1, 2_43_1, 2_177_1, 1_132_1, 1_268_1, 1_116_1L-Q45K; 1_257_1L-L21I; 1_314_1H-T92A; 1_46_1H-L81M; 2_112_1H-I12V; 2_112_1L-F58I; 2_112_1L-I85V; 2_112_1H-L81M, L-F58I; 2_112_1H-L81M, L-I85V; or 2_112_1H-L81M, L-F58I, I85V; (b) an antibody that comprises a heavy chain variable domain having the amino acid sequence of the $V_H$ domain in any one of SEQ ID NOS: 2, 6, 10, 14, 18, 22, 26, 30, 34, 38, 42, 45, 49, 53, 57, 61, 65, 69, 73, 77, 81 or 85, (c) an antibody that comprises a light chain variable domain having the amino acid sequence of the $V_L$ domain in any one of SEQ ID NOS: 4, 8, 12, 16, 20, 24, 28, 32, 36, 40, 44, 47, 51, 55, 59, 63, 67, 71, 75, 79, 83 or 87 (d) an antibody that comprises both a heavy chain variable domain as defined in (b) and a light chain variable domain as defined in (c).

One can determine whether an antibody binds to the same epitope or cross competes for binding with an anti-myostatin antibody by using methods known in the art. In one embodiment, one allows the anti-myostatin antibody of the invention to bind to myostatin under saturating conditions and then measures the ability of the test antibody to bind to myostatin. If the test antibody is able to bind to myostatin at the same time as the reference anti-myostatin antibody, then the test antibody binds to a different epitope than the reference anti-myostatin antibody. However, if the test antibody is not able to bind to myostatin at the same time, then the test antibody binds to the same epitope, an overlapping epitope, or an epitope that is in close proximity to the epitope bound by the anti-myostatin antibody of the invention. This experiment can be performed using ELISA, RIA, BIACORE®, or flow cytometry. To test whether an anti-myostatin antibody cross-competes with another anti-myostatin antibody, one may use the competition method described above in two directions, i.e. determining if the known antibody blocks the test antibody and vice versa. In a preferred embodiment, the experiment is performed using ELISA.

Inhibition of Myostatin Activity by Anti-Myostatin Antibody

One can identify anti-myostatin monoclonal antibodies that inhibit myostatin binding using a number of assays. For example, neutralizing anti-myostatin antibodies can be identified by their ability to block myostatin-induced luciferase activity in A204 cells transfected with a Smad response elements/luciferase construct as described in Example III. Preferred anti-myostatin antibodies have an $IC_{50}$ of no more than 500 nM, 250 nM, 100 nM, 75 nM, 50 nM, 40 nM, 30 nM, 20 nM, 10 nM, 1 nM, 0.5 nM or 0.1 nM.

One also can determine the ability of an anti-myostatin antibody to block myostatin-induced Smad protein activation by contacting L6 rat myoblast cells transfected with a Smad 2/3-binding element/beta lactamase construct with an anti-myostatin antibody as described in Example IV. In various embodiments, the anti-myostatin antibody has an $IC_{50}$ in this assay of no more than 500 nM, 250 nM, 100 nM, 75 nM, 50 nM, 40 nM, 30 nM, 20 nM, 10 nM, 1 nM, 0.5 nM or 0.1 nM.

Alternatively, neutralizing anti-myostatin anti-bodies can be identified by their ability to inhibit Smad 2 or 3 phosphorylation in a Western Blot as described in Example V.

In other embodiments, an anti-myostatin antibody of the invention modulates the expression of genes associated with muscle cell proliferation and differentiation. Such modulation includes but is not limited to decreasing expression of the cell cycle inhibitor P21 protein and pro-apoptotic Bax protein, increasing phosphorylation of Rb, and increasing expression of Cdk2. In some embodiments, antagonist anti-myostatin antibodies of the invention increase the expression of MyoD, myogenin and Myf5. The effect of an anti-myostatin antibody on gene expression can be determined using any of a number of routine techniques. (See e.g., Example VI).

In some embodiments, a neutralizing anti-myostatin antibody of the invention enhances myoblast differentiation. The ability of an antibody to enhance such proliferation and differentiation can be determined by assays using, e.g., C2C12 cells as described in Example VII.

Competitive Vs Non-Competitive Human Anti-Myostatin Antibodies

Human anti-myostatin antibodies of the invention can be categorized as competitive and non-competitive with other inhibitory myostatin binding proteins using immunoprecipitation experiments. For example, the propeptide, which forms a complex with mature GDF8 is an inhibitory protein. Conditioned medium from 293T cells expressing GDF8 contains mature GDF8, mature GDF8/propeptide complex and unprocessed GDF8. Immunoprecipitation studies were conducted to test the binding of the human anti-myostatin antibodies in the invention to mature GDF8/propetide complex using this conditioned medium. As described in Example X, antibodies 2_112_1, 2_43_1 and 2_177_1 bound and immunoprecipitated mature GDF8, mature GDF8/propeptide complex, and unprocessed GDF8. Antibody 1_66_1 bound and immunoprecipitated mature GDF8 and mature GDF8/propeptide complex. None of the other antibodies immunoprecipitated mature GDF8, propeptide, or unprocessed GDF8. Antibodies 2_112_1, 2_43_1 and 2_177_1, thus, are non-competitive antibodies, and antibody 1_66_1 also is a non-competitive antibody but one that binds to a different epitope of myostatin. A non-competitive neutralizing antibody, i.e., one that binds myostatin in the presence of other inhibitory proteins, will have better in vivo efficacy than a competitive antibody.

In other embodiments, an anti-myostatin antibody of the invention immunoprecipitates mature GDF8 from mouse serum. As described in Example XI, monoclonal antibodies 2_112, 2_43_1 and 2_177 pull down more mature GDF8 than 1_116_1 and 166_1.

Species Specificity and Molecular Selectivity

In another aspect of the invention, the anti-myostatin antibodies demonstrate both species specificity and molecular selectivity. In some embodiments, the anti-myostatin antibody binds to human, mouse, *Rattus norvegicus* (Norway rat), *cynomolgus macaque* (monkey), *Macaca fascicularis* (crab-eating macaque), *Meleagris gallopavo* (turkey), *Sus scrofa* (pig), *Gallus gallus* (chicken), *Gallus gallus* (chicken), *Canis familiaris* (dog), *Equus caballus* (horse), *Coturnix chinensis* (Quail), *Cotumix coturnix* (common quail), and *Columba livia* (domestic pigeon) myostatin. Following the teachings of the specification, one may determine the species specificity for the anti-myostatin antibody using methods well known in the art. For instance, one may determine the species specificity using Western blot, surface plasmon resonance, e.g., BIACORE®, ELISA, immunoprecipitation or RIA.

In other embodiments, the anti-myostatin antibody has a selectivity for myostatin over GDF11 of at least 50-fold or at least 100-fold. GDF11 is a close family member of myostatin that shares ninety percent identity in its mature protein. In some embodiments, the anti-myostatin antibody does not exhibit any appreciable specific binding to any other protein other than myostatin. One can determine the selectivity of the anti-myostatin antibody for myostatin using methods well known in the art following the teachings of the specification. For instance one can determine the selectivity using Western blot, flow cytometry, ELISA, immunoprecipitation or RIA.

In other embodiments of the invention, the anti-myostatin antibody does not have this high degree of selectivity for GDF8 over GDF11.

Methods of Producing Antibodies and Antibody Producing Cell Lines

Immunization

In some embodiments, human antibodies are produced by immunizing a non-human, transgenic animal comprising within its genome some or all of human immunoglobulin heavy chain and light chain loci with a myostatin antigen. In a preferred embodiment, the non-human animal is a XENOMOUSE® animal. (Abgenix, Inc., Fremont, Calif.).

XENOMOUSE® mice are engineered mouse strains that comprise large fragments of human immunoglobulin heavy chain and light chain loci and are deficient in mouse antibody production. See, e.g., Green et al., Nature Genetics 7:13-21 (1994) and U.S. Pat. Nos. 5,916,771, 5,939,598, 5,985,615, 5,998,209, 6,075,181, 6,091,001, 6,114,598, 6,130,364, 6,162,963 and 6,150,584. See also WO 91/10741, WO 94/02602, WO 96/34096, WO 96/33735, WO 98/16654, WO 98/24893, WO 98/50433, WO 99/45031, WO 99/53049, WO 00/09560, and WO 00/037504.

In another aspect, the invention provides a method for making anti-myostatin antibodies from non-human, non-mouse animals by immunizing non-human transgenic animals that comprise human immunoglobulin loci with a myostatin antigen. One can produce such animals using the methods described in the above-cited documents. The methods disclosed in these documents can be modified as described in U.S. Pat. No. 5,994,619, which is hereby incorporated by reference. U.S. Pat. No. 5,994,619 describes methods for producing novel cultured inner cell mass (CICM) cells and cell lines, derived from pigs and cows, and transgenic CICM cells into which heterologous DNA has been inserted. CICM transgenic cells can be used to produce cloned transgenic embryos, fetuses, and offspring. The '619 patent also describes methods of producing transgenic animals that are capable of transmitting the heterologous DNA to their progeny. In preferred embodiments of the current invention, the non-human animals are mammals, particularly rats, sheep, pigs, goats, cattle, horses or chickens.

XENOMOUSE® mice produce an adult-like human repertoire of fully human antibodies and generate antigen-specific human antibodies. In some embodiments, the XENOMOUSE® mice contain approximately 80% of the human antibody V gene repertoire through introduction of megabase sized, germline configuration fragments of the human heavy chain loci and kappa light chain loci in yeast artificial chromosome (YAC). In other embodiments, XENOMOUSE® mice further contain approximately all of the human lambda light chain locus. See Mendez et al., *Nature Genetics* 15:146-156 (1997), Green and Jakobovits, *J. Exp. Med.* 188:483-495 (1998), and WO 98/24893, the disclosures of which are hereby incorporated by reference.

In some embodiments, the non-human animal comprising human immunoglobulin genes are animals that have a human immunoglobulin "minilocus". In the minilocus approach, an exogenous Ig locus is mimicked through the inclusion of individual genes from the Ig locus. Thus, one or more $V_H$ genes, one or more $D_H$ genes, one or more $J_H$ genes, a mu constant domain, and a second constant domain (preferably a gamma constant domain) are formed into a construct for insertion into an animal. This approach is described, inter alia, in U.S. Pat. Nos. 5,545,807, 5,545,806, 5,569,825, 5,625,126, 5,633,425, 5,661,016, 5,770,429, 5,789,650, 5,814,318, 5,591,669, 5,612,205, 5,721,367, 5,789,215, and 5,643,763, hereby incorporated by reference.

In another aspect, the invention provides a method for making humanized anti-myostatin antibodies. In some embodiments, non-human animals are immunized with a myostatin antigen as described below under conditions that permit antibody production. Antibody-producing cells are isolated from the animals, and nucleic acids encoding the heavy and light chains of an anti-myostatin antibody of interest are isolated from the isolated antibody-producing cells or from an immortalized cell line produced from such cells. These nucleic acids are subsequently engineered using techniques known to those of skill in the art and as described further below to reduce the amount of non-human sequence, i.e., to humanize the antibody to reduce the immune response in humans.

In some embodiments, the myostatin antigen is isolated and/or purified myostatin. In some embodiments, the myostatin antigen is human myostatin. However, because the C-terminal mature myostatin from humans, mice, rat, dog, quail, chicken, turkey, pig, horse, and monkeys is identical and is not glycosylated in cells, myostatin from these species and other species having the same mature protein sequence also can be used as the immunogen. In other embodiments, the myostatin antigen is a cell that expresses or overexpresses myostatin. In other embodiments, the myostatin antigen is a recombinant protein expressed from yeast, insect cells, bacteria such as E. Coli, or other resources by recombinant technology.

Immunization of animals can be by any method known in the art. See, e.g., Harlow and Lane, *Antibodies: A Laboratory Manual*, New York: Cold Spring Harbor Press, 1990. Methods for immunizing non-human animals such as mice, rats, sheep, goats, pigs, cattle and horses are well known in the art. See, e.g., Harlow and Lane, supra, and U.S. Pat. No. 5,994, 619. In a preferred embodiment, the myostatin antigen is administered with an adjuvant to stimulate the immune response. Exemplary adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks. Example I exemplifies a method for producing anti-myostatin monoclonal antibodies in XENOMOUSE® mice.

Production of Antibodies and Antibody-Producing Cell Lines

After immunization of an animal with a myostatin antigen, antibodies and/or antibody-producing cells can be obtained from the animal. In some embodiments, anti-myostatin antibody-containing serum is obtained from the animal by bleeding or sacrificing the animal. The serum may be used as it is obtained from the animal, an immunoglobulin fraction may be obtained from the serum, or the anti-myostatin antibodies may be purified from the serum.

In some embodiments, antibody-producing cell lines are prepared from cells isolated from the immunized animal. After immunization, the animal is sacrificed and lymph node and/or splenic B cells are immortalized by any means known in the art. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. See, e.g., Harlow and Lane, supra. If fusion with myeloma cells is used, the myeloma cells preferably do not secrete immunoglobulin polypeptides (a non-secretory cell line). Immortalized cells are screened using myostatin, or a portion thereof. In a preferred embodiment, the initial screening is performed using an enzyme-linked immunoassay (ELISA) or a radioimmunoassay. An example of ELISA screening is provided in WO 00/37504, incorporated herein by reference.

Anti-myostatin antibody-producing cells, e.g., hybridomas, are selected, cloned and further screened for desirable characteristics, including robust growth, high antibody production and desirable antibody characteristics, as discussed further below. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, the immunized animal is a non-human animal that expresses human immunoglobulin genes and the splenic B cells are fused to a myeloma cell line from the same species as the non-human animal. In a more preferred embodiment, the immunized animal is a XENOMOUSE® mouse and the myeloma cell line is a non-secretory mouse myeloma. In an even more preferred embodiment, the myeloma cell line is P3-X63-Ag8.653 (American Type Culture Collection). See, e.g., Example I.

Thus, in one embodiment, the invention provides methods for producing a cell line that produces a human monoclonal antibody or a fragment thereof directed to myostatin comprising (a) immunizing a non-human transgenic animal described herein with myostatin, a portion of myostatin or a cell or tissue expressing myostatin; (b) allowing the transgenic animal to mount an immune response to myostatin; (c) isolating antibody-producing cells from transgenic animal; (d) immortalizing the antibody-producing cells; (e) creating individual monoclonal populations of the immortalized antibody-producing cells; and (f) screening the immortalized antibody-producing cells to identify an antibody directed to myostatin.

In another aspect, the invention provides a cell line that produces a human anti-myostatin antibody. In some embodiments the cell line is a hybridoma cell line. In some embodiments, the hybridomas are mouse hybridomas, as described above. In other embodiments, the hybridomas are produced in a non-human, non-mouse species such as rats, sheep, pigs, goats, cattle or horses. In another embodiment, the hybridomas are human hybridomas.

In another embodiment, a transgenic animal is immunized with a myostatin antigen, primary cells, e.g., spleen or peripheral blood B cells, are isolated from an immunized transgenic animal and individual cells producing antibodies specific for the desired antigen are identified. Polyadenylated mRNA from each individual cell is isolated and reverse transcription polymerase chain reaction (RT-PCR) is performed using sense primers that anneal to variable domain sequences, e.g., degenerate primers that recognize most or all of the FR1 regions of human heavy and light chain variable domain genes and anti-sense primers that anneal to constant or joining region sequences. cDNAs of the heavy and light chain variable domains are then cloned and expressed in any suitable host cell, e.g., a myeloma cell, as chimeric antibodies with respective immunoglobulin constant regions, such as the heavy chain and κ or λ constant domains. See Babcook, J. S. et al., *Proc. Natl. Acad. Sci. USA* 93:7843-48, 1996, incorporated herein by reference. Anti myostatin antibodies may then be identified and isolated as described herein.

In another embodiment, phage display techniques can be used to provide libraries containing a repertoire of antibodies with varying affinities for myostatin. For production of such repertoires, it is unnecessary to immortalize the B cells from the immunized animal. Rather, the primary B cells can be used directly as a source of mRNA. The mixture of cDNAs obtained from B cell, e.g., derived from spleens, is used to prepare an expression library, for example, a phage display library transfected into *E. coli*. The resulting cells are tested for immunoreactivity to myostatin. Techniques for the identification of high affinity human antibodies from such libraries are described by Griffiths et al., *EMBO J.*, 13:3245-3260 (1994); Nissim et al., ibid, pp. 692-698 and by Griffiths et al., ibid, 12:725-734, which are incorporated by reference. Ultimately, clones from the library are identified that produce binding affinities of a desired magnitude for the antigen and the DNA encoding the product responsible for such binding is recovered and manipulated for standard recombinant expression. Phage display libraries may also be constructed using previously manipulated nucleotide sequences and screened in a similar fashion. In general, the cDNAs encoding heavy and light chains are independently supplied or linked to form Fv analogs for production in the phage library.

The phage library is then screened for the antibodies with the highest affinities for myostatin and the genetic material recovered from the appropriate clone. Further rounds of screening can increase affinity of the original antibody isolated.

Nucleic Acids, Vectors, Host Cells, and Recombinant Methods of Making Antibodies Nucleic Acids The present invention also encompasses nucleic acid molecules encoding anti-myostatin antibodies or an antigen-binding fragments thereof. In some embodiments, different nucleic acid molecules encode a heavy chain and a light chain of an anti-myostatin immunoglobulin. In other embodiments, the same nucleic acid molecule encodes a heavy chain and a light chain of an anti-myostatin immunoglobulin.

In some embodiments, the nucleic acid molecule encoding the variable domain of the light chain ($V_L$) utilizes a human A3, A30 or L2 Vκ gene, and a human Jκ1, Jκ3 or Jκ4 gene. In some embodiments the nucleic acid molecule utilizes a human A30, A3 or L2 Vκ gene and a human Jκ4 gene. In other embodiments, the nucleic acid molecule utilizes a human A30, A3 or L2 gene and a human Jκ1 gene. In some embodiments, the nucleic acid molecule encoding the light chain encodes an amino acid sequence comprising 1, 2, 3, 4, 5, 6, 7, 8, 9, or 10 substitutions from the germline amino acid sequence(s). In some embodiments, the nucleic acid molecule comprises a nucleotide sequence that encodes a $V_L$ amino acid sequence comprising 1, 2, 3, 4 or 5 conservative amino acid substitutions and/or 1, 2, or 3 non-conservative substitutions compared to germline $V_K$ and $J_K$ sequences. Substitutions may be in the CDR regions, the framework regions, or in the constant domain.

In some embodiments, the nucleic acid molecule encodes a $V_L$ amino acid sequence comprising one or more mutations compared to the germline sequence that are identical to the mutations from germline found in the $V_L$ of any one of antibodies 1_116_1, 1_136_3, 1_257_1, 1_46_1, 2_112_1, 1_314_1, 1_66_1, 2_43_1, 2_177_1, 1_132_1, 1_268_1, 1_116_1L-Q45K; 1_257_1L-L21I; 1_314_1H-T92A; 1_46_1H-L81M; 2_112_1H-I12V; 2_112_1L-F58I; 2_112_1L-I85V; 2_112_1H-L81M, L-F58I; 2_112_1H-L81M, L-I85V; or 2_112_1H-L81M, L-F58I, I85V.

In some embodiments, the nucleic acid molecule encodes at least three amino acid substitutions compared to the germline sequence found in the $V_L$ of any one of the antibodies 1_116_1, 1_136_3, 1_257_1, 1_46_1, 2_112_1, 1_314_21, 1_66_1, 2_43_1, 2_177_1, 1_132_1, 1_268_1, 1_116_1L-Q45K; 1_257_1L-L21I; 1_314_1H-T92A; 1_461H-L81M; 2_112_1H-I12V; 2_112_1L-F58I; 2_112_1L-I85V; 2_112_1H-L81M, L-F58I; 2_112_1H-L81M, L-I85V; or 2_112_1H-L81M, L-F58I, I85V.

In some embodiments, the nucleic acid molecule comprises a nucleotide sequence that encodes the $V_L$ amino acid sequence of monoclonal antibody 1_116_1 (SEQ ID NO: 4); 1_136_3 (SEQ ID NO: 12); 1_257_1 (SEQ ID NO: 16); 1_46_1 (SEQ ID NO: 24); 2_112_1 (SEQ ID NO: 28); 1_314_1 (SEQ ID NO: 20-_); 1_66_1 (SEQ ID NO: 36); 2_43_1 (SEQ ID NO: 28); 2_177_1 (SEQ ID NO: 40); 1_132_1 (SEQ ID NO: 8); or 1_268_1 (SEQ ID NO: 32) or a variant or portion thereof. In some embodiments, the nucleic acid encodes an amino acid sequence comprising the light chain CDRs of one of said above-listed antibodies. In some embodiments, said portion is a contiguous portion comprising CDR1-CDR3.

In some embodiments, the nucleic acid molecule comprises a nucleotide sequence that encodes the amino acid sequence of one of SEQ ID NOs: 4, 8, 12, 16, 20, 24, 28, 32, 36, 40, 44, 47, 51, 55, 59, 63, 67, 71, 75, 79, 83 or 87. In some embodiments, the nucleic acid molecule comprises the nucleotide sequence of SEQ ID NOs: 3, 7, 11, 15, 19, 23, 27, 31, 35, 39, 43, 48, 52, 56, 60, 68, 72, 80, 64, 76, 84 or 88 or a portion thereof. In some embodiments, the nucleic acid encodes the amino acid sequence of the light chain of one, two or all three CDRs of said antibody. In some embodiments, said portion encodes a contiguous region from CDR1-CDR3 of the light chain of an anti-myostatin antibody.

In some embodiments, the nucleic acid molecule encodes a $V_L$ amino acid sequence that is at least 70%, 75%, 80%, 85%, 90%, 95%, 97%, 98% or 99% identical to the $V_L$ amino acid sequence of any one of antibodies 1_116_1, 1_136_3, 1_257_1, 1_46_1, 2_112_1, 1_314_1, 1_66_1, 2_43_1, 2_177_1, 1_132_1, 1_268_1, 1_116_1L-Q45K; 1_257_1L-L21I; 1_314_1H-T92A; 1_46_1H-L81M; 2_112_1H-I12V; 2_112_1L-F58I; 2_112_1L-I85V; or 2_112_1H-L81M, L-F58I; 2_112_1H-L81M, L-I85V; or 2_112_1H-L81M, L-F58I, I85V, or to the amino acid sequence of the $V_L$ region of any one of SEQ ID NOs: 4, 8, 12, 16, 20, 24, 28, 32, 36, 40, 44, 47, 51, 55, 59, 63, 67, 71, 75, 79, 83 or 87. Nucleic acid molecules of the invention include nucleic acids that hybridize under highly stringent conditions, such as those described above, or that are at least 70%, 75%, 80%, 85%, 90%, 95%, 97%, 98% or 99% identical to a nucleic acid encoding the amino acid sequence the $V_L$ region of SEQ ID NOs: 4, 8, 12, 16, 20, 24, 28, 32, 36, 40, 44, 47, 51, 55, 59, 63, 67, 71, 75, 79, 83 or 87 or to a nucleic acid comprising the $V_L$ region nucleotide sequence of SEQ ID NOs: 3, 7, 11, 15, 19, 23, 27, 31, 35, 39, 43, 48, 52, 56, 60, 68, 72, 80, 64, 76, 84 or 88

In other preferred embodiments, the nucleic acid molecule encodes the variable domain of a heavy chain ($V_H$) that utilizes a human 1-02, 3-21 or 3-23 $V_H$ gene sequence or a sequence derived therefrom. In various embodiments, the nucleic acid molecule utilizes a human $V_H$ 1-02 gene, a D4-23 gene and a human $J_H$6b gene; a human $V_H$ 3-21 gene, a human D3-16 or D5-12 gene and a human $J_H$6b gene; a human $V_H$ 3-21 gene, a human D1-26 or D5-5 gene and a human $J_H$4b gene; a human $V_H$ 3-23 gene, a human D1-7 gene and a human $J_H$3b gene.

In some embodiments, the nucleic acid molecule encodes an amino acid sequence comprising 1, 2, 3, 4, 5, 6, 7, 8, 9, 10 or 11 mutations compared to the germline amino acid sequence of the human V, D or J genes. In some embodiments, said mutations are in the $V_H$ region. In some embodiments, said mutations are in the CDR regions.

In some embodiments, the nucleic acid molecule encodes a $V_H$ sequence comprising one or more amino acid mutations compared to the germline $V_H$ sequence that are identical to amino acid mutations found in the $V_H$ of monoclonal antibody 1_116_1, 1_136_3, 1_257_1, 1_46_1, 2_112_1, 1_314_1, 1_66_1, 2_43_1, 2_177_1, 1_132_1, 1_268_1, 1_116_1L-Q45K; 1_257_1L-L21I; 1_314_1H-T92A; 1_46_1H-L81M; 2_112_1H-I12V; 2_112_1L-F58I; 2_112_1L-I85V; 2_112_1H-L81M, L-F58I; 2_112_1H-L81M, L-I85V; or 2_112_1H-L81M, L-F58I, I85V. In some embodiments, the nucleic acid encodes at least three amino acid mutations compared to the germline sequences that are identical to at least three amino acid mutations found in one of the above-listed monoclonal antibodies.

In some embodiments, the nucleic acid molecule comprises a nucleotide sequence that encodes at least a portion of the $V_H$ amino acid sequence of a monoclonal antibody selected from 1_116_1 (SEQ ID NO: 2); 1_136_3 (SEQ ID NO: 10); 1_257_1 (SEQ ID NO: 14); 1_46_1 (SEQ ID NO: 22); 2_112_1 (SEQ ID NO: 26); 1_314_1 (SEQ ID NO: 18); 1_66_1 (SEQ ID NO: 34); 2_43_1 (SEQ ID NO: 42); 2_177_1 (SEQ ID NO: 38); 1_132_1 (SEQ ID NO: 6); or 1_268_1 (SEQ ID NO: 30), a variant thereof, or said sequence having conservative amino acid mutations and/or a total of three or fewer non-conservative amino acid substitutions. In various embodiments the sequence encodes one or more CDR regions, preferably a CDR3 region, all three CDR regions, a contiguous portion including CDR1-CDR3, or the entire $V_H$ region, of an above-listed anti-myostatin antibody.

In some embodiments, the nucleic acid molecule comprises a nucleotide sequence that encodes the amino acid sequence of one of SEQ ID NOs: 2, 6, 10, 14, 18, 22, 26, 30, 34, 38, 42, 45, 49, 53, 57, 61, 65, 69, 73, 77, 81 or 85. In various preferred embodiments, the nucleic acid molecule comprises at least a portion of the nucleotide sequence of SEQ ID NOS: 1, 5, 9, 13, 17, 21, 25, 29, 33, 37, 41, 46, 50, 54, 58, 62, 66, 70, 74, 78, 82 or 86. In some embodiments, said portion encodes the $V_H$ region, a CDR3 region, all three CDR regions, or a contiguous region including CDR1-CDR3.

In some embodiments, the nucleic acid molecule encodes a $V_H$ amino acid sequence that is at least 70%, 75%, 80%, 85%, 90%, 95%, 97%, 98% or 99% identical to the $V_H$ amino acid sequence in any one of SEQ ID NOS: 2, 6, 10, 14, 18, 22, 26, 30, 34, 38, 42, 45, 49, 53, 57, 61, 65, 69, 73, 77, 81 or 85. Nucleic acid molecules of the invention include nucleic acids that hybridize under highly stringent conditions, such as those described above, or that are at least 70%, 75%, 80%, 85%, 90%, 95%, 97%, 98% or 99% identical to a nucleic acid encoding the amino acid sequence of SEQ ID NO: 2, 6, 10, 14, 18, 22, 26, 30, 34, 38 or 42 or to a $V_H$ region thereof, or to a nucleic acid comprising the nucleotide sequence of SEQ ID NOs: 1, 5, 9, 13, 17, 21, 25, 29, 33, 37 or 41 or the nucleotide sequence that encodes a $V_H$ region thereof.

In another embodiment, the nucleic acid encodes a full-length heavy chain of an antibody selected from 1_116_1, 1_136_3, 1_257_1, 1_46_1, 2_112_1, 1_314_1, 1_66_1, 2_43_1, 2_177_1, 1_132_1, 1_268_1, 1_116_1L-Q45K; 1_257_1L-L21I; 1_314_1H-T92A; 1_46_1H-L81M; 2_112_1H-I12V; 2_112_1L-F58I; 2_112_1L-I85V; 2_112_1H-L81M, L-F58I; 2_112_1H-L81M, L-I85V; or 2_112_1H-L81M, L-F58I, I85V, or a heavy chain comprising the amino acid sequence of SEQ ID NOs: 2, 6, 10, 14, 18, 22, 26, 30, 34, 38 or 42. Further, the nucleic acid may comprise the nucleotide sequence of SEQ ID NOs: 1, 5, 9, 13, 17, 21, 25, 29, 33, 37 or 41.

A nucleic acid molecule encoding the heavy or light chain of an anti-myostatin antibody or portions thereof can be isolated from any source that produces such antibody. In various embodiments, the nucleic acid molecules are isolated from a B cell that expresses an anti-myostatin antibody isolated from an animal immunized with myostatin or from an immortalized cell derived from such a B cell. Methods of isolating nucleic acids encoding an antibody are well-known in the art. See, e.g., Sambrook et al. mRNA may be isolated and used to produce cDNA for use in the polymerase chain reaction (PCR) or cDNA cloning of antibody genes. In a preferred embodiment, the nucleic acid molecule is isolated from a hybridoma that has as one of its fusion partners a cell from a non-human transgenic animal, said cell producing a human immunoglobulin. In an even more preferred embodiment, the cell producing human immunoglobulin is isolated from a XENOMOUSE® animal. In another embodiment, the cell producing the human immunoglobulin is isolated from a non-human, non-mouse transgenic animal, as described above. In another embodiment, the nucleic acid is isolated from a non-human, non-transgenic animal. The nucleic acid molecules isolated from a non-human, non-transgenic animal may be used, e.g., for humanized antibodies that comprise one or more amino acid sequences from a human anti-myostatin antibody of the present invention.

In some embodiments, a nucleic acid encoding a heavy chain of an anti-myostatin antibody of the invention can comprise a nucleotide sequence encoding a $V_H$ domain of the invention joined in-frame to a nucleotide sequence encoding a heavy chain constant domain from any source. Similarly, a nucleic acid molecule encoding a light chain of an anti-myostatin antibody of the invention can comprise a nucleotide sequence encoding a $V_L$ domain of the invention joined in-frame to a nucleotide sequence encoding a light chain constant domain from any source.

In a further aspect of the invention, nucleic acid molecules encoding the variable domain of the heavy ($V_H$) and/or light ($V_L$) chains are "converted" to full-length antibody genes. In one embodiment, nucleic acid molecules encoding the $V_H$ or $V_L$ domains are converted to full-length antibody genes by insertion into an expression vector already encoding heavy chain constant ($C_H$) or light chain constant ($C_L$) domains, respectively, such that the $V_H$ segment is operatively linked to the $C_H$ segment(s) within the vector, and/or the $V_L$ segment is operatively linked to the $C_L$ segment within the vector. In another embodiment, nucleic acid molecules encoding the $V_H$ and/or $V_L$ domains are converted into full-length antibody genes by linking, e.g., ligating, a nucleic acid molecule encoding a $V_H$ and/or $V_L$ domains to a nucleic acid molecule encoding a $C_H$ and/or $C_L$ domain using standard molecular biological techniques. Nucleic acid sequences of human heavy and light chain immunoglobulin constant domain genes are known in the art. See, e.g., Kabat et al. *Sequences of Proteins of Immunological Interest,* 5th Ed., NIH Publ. No. 91-3242, 1991. Nucleic acid molecules encoding the full-length heavy and/or light chains may then be expressed from a cell into which they have been introduced and the anti-myostatin antibody isolated.

The nucleic acid molecules may be used to recombinantly express large quantities of anti-myostatin antibodies. The nucleic acid molecules also may be used to produce chimeric antibodies, bispecific antibodies, single chain antibodies, immunoadhesins, diabodies, mutated antibodies and antibody derivatives, as described further below. If the nucleic acid molecules are derived from a non-human, non-transgenic animal, the nucleic acid molecules may be used for antibody humanization, also as described below.

In another embodiment, a nucleic acid molecule of the invention is used as a probe or PCR primer for a specific antibody sequence. For instance, the nucleic acid can be used as a probe in diagnostic methods or as a PCR primer to amplify regions of DNA that could be used, inter alia, to isolate additional nucleic acid molecules encoding variable domains of anti-myostatin antibodies. In some embodiments, the nucleic acid molecules are oligonucleotides. In some embodiments, the oligonucleotides are from highly variable domains of the heavy and light chains of the antibody of interest. In some embodiments, the oligonucleotides encode all or a part of one or more of the CDRs of antibodies 1_116_1, 1_136_3, 1_257_1, 1_46_1, 2_112_1, 1_314_1, 1_66_1, 2_43_1, 2_177_1, 1_132_1, 1_268_1, 1_116_1L-Q45K; 1_257_1L-L21I; 1_314_1H-T92A; 1_46_1H-L81M; 2_112_1H-I12V; 2_112_1L-F58I; 2_112_1L-I85V; 2_112_1H-L81M, L-F58I; or 2_112_1H-L81M, L-I85V; or 2_112_1H-L81M, L-F58I, I85V or variants thereof as described herein.

Vectors

The invention provides vectors comprising nucleic acid molecules that encode the heavy chain of an anti-myostatin antibody of the invention or an antigen-binding portion thereof. The invention also provides vectors comprising nucleic acid molecules that encode the light chain of such antibodies or antigen-binding portion thereof. The invention further provides vectors comprising nucleic acid molecules encoding fusion proteins, modified antibodies, antibody fragments, and probes thereof.

In some embodiments, the anti-myostatin antibodies of the invention or antigen-binding portions are expressed by inserting DNAs encoding partial or full-length light and heavy chains, obtained as described above, into expression vectors such that the genes are operatively linked to necessary expression control sequences such as transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human $C_H$ or $C_L$ immunoglobulin sequence, with appropriate restriction sites engineered so that any $V_H$ or $V_L$ sequence can easily be inserted and expressed, as described above. In such vectors, splicing usually occurs between the splice donor site in the inserted J region and the splice acceptor site preceding the human C domain, and also at the splice regions that occur within the human $C_H$ exons. Polyadenylation and transcription termination occur at native chromosomal sites downstream of the coding regions. The recombinant expression vector also can encode a signal peptide that facilitates secretion of the antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. No. 5,168,062, U.S. Pat. No. 4,510,245 and U.S. Pat. No. 4,968,615. Methods for expressing antibodies in plants, including a description of promoters and vectors, as well as transformation of plants is known in the art. See, e.g., U.S. Pat. No. 6,517,529, incorporated herein by reference. Methods of expressing polypeptides in bacterial cells or fungal cells, e.g., yeast cells, are also well known in the art.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, incorporated herein by reference). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification), the neo gene (for G418 selection), and the glutamate synthetase gene.

Non-Hybridoma Host Cells and Methods of Recombinantly Producing Protein

Nucleic acid molecules encoding anti-myostatin antibodies and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455, incorporated herein by reference). Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NS0 cells, SP2 cells, HEK-293T cells, NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected through determining which cell lines have high expression levels.

Cell lines other than those of mammalian origin can also be used. These include insect cell lines (such as Sf9 or Sf21 cells), plant cells (including those from *Nicotiana, Arabidopsis*, duckweed, corn, wheat, potato, etc.), bacterial cells (including *E. coli* and *Streptomyces*) and yeast cells (including *Schizosaccharomyces pombe, Saccharomyces cerevisiae* and *Pichia pastoris*).

When recombinant expression vectors encoding antibody genes are introduced into host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Expression of antibodies of the invention from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, 0 323 997 and 0 338 841.

It is likely that antibodies expressed by different cell lines or in transgenic animals will have different glycosylation from each other. However, all antibodies encoded by the nucleic acid molecules provided herein, or comprising the amino acid sequences provided herein are part of the instant invention, regardless of the glycosylation of the antibodies.

Transgenic Animals and Plants

Anti-myostatin antibodies of the invention also can be produced transgenically through the generation of a mammal or plant that is transgenic for the immunoglobulin heavy and light chain sequences of interest and production of the antibody in a recoverable form therefrom. In connection with the transgenic production in mammals, anti-myostatin antibodies can be produced in, and recovered from, the milk of goats, cows, or other mammals. See, e.g., U.S. Pat. Nos. 5,827,690, 5,756,687, 5,750,172, and 5,741,957, incorporated herein by reference. In some embodiments, non-human transgenic animals that comprise human immunoglobulin loci are immunized with myostatin or an immunogenic portion thereof, as described above. Methods for making antibodies in plants are described, e.g., in U.S. Pat. Nos. 6,046,037 and 5,959,177, incorporated herein by reference.

In some embodiments, non-human transgenic animals or plants are produced by introducing one or more nucleic acid molecules encoding an anti-myostatin antibody of the invention into the animal or plant by standard transgenic techniques. See Hogan and U.S. Pat. No. 6,417,429, supra. The transgenic cells used for making the transgenic animal can be embryonic stem cells or somatic cells or a fertilized egg. The transgenic non-human organisms can be chimeric, nonchimeric heterozygotes, and nonchimeric homozygotes. See, e.g., Hogan et al. *Manipulating the Mouse Embryo: A Laboratory Manual* $2^{nd}$ ed., Cold Spring Harbor Press (1999); Jackson et al., *Mouse Genetics and Transgenics: A Practical Approach*, Oxford University Press (2000); and Pinkert, *Transgenic Animal Technology: A Laboratory Handbook*, Academic Press (1999), all incorporated herein by reference. In some embodiments, the transgenic non-human animals have a targeted disruption and replacement by a targeting construct that encodes a heavy chain and/or a light chain of interest. In a preferred embodiment, the transgenic animals comprise and express nucleic acid molecules encoding heavy and light chains that specifically bind to myostatin, preferably human myostatin. In some embodiments, the transgenic animals comprise nucleic acid molecules encoding a modified antibody such as a single-chain antibody, a chimeric antibody or a humanized antibody. The anti-myostatin antibodies may be made in any transgenic animal. In a preferred embodiment, the non-human animals are mice, rats, sheep, pigs, goats, cattle or horses. The non-human transgenic animal expresses said encoded polypeptides in blood, milk, urine, saliva, tears, mucus and other bodily fluids.

Phage Display Libraries

The invention provides a method for producing an anti-myostatin antibody or antigen-binding portion thereof comprising the steps of synthesizing a library of human antibodies on phage, screening the library with myostatin or an antibody-binding portion thereof, isolating phage that bind myostatin, and obtaining the antibody from the phage. By way of example, one method for preparing the library of antibodies for use in phage display techniques comprises the steps of immunizing a non-human animal comprising human immunoglobulin loci with myostatin or an antigenic portion thereof to create an immune response, extracting antibody-producing cells from the immunized animal; isolating RNA encoding heavy and light chains of antibodies of the invention from the extracted cells, reverse transcribing the RNA to produce cDNA, amplifying the cDNA using primers, and inserting the cDNA into a phage display vector such that antibodies are expressed on the phage. Recombinant anti-myostatin antibodies of the invention may be obtained in this way.

Recombinant human anti-myostatin antibodies of the invention can be isolated by screening a recombinant combinatorial antibody library. Preferably the library is a scFv phage display library, generated using human $V_L$ and $V_H$ cDNAs prepared from mRNA isolated from B cells. Methods for preparing and screening such libraries are known in the art. Kits for generating phage display libraries are commercially available (e.g., the Pharmacia Recombinant Phage Antibody System, catalog no. 27-9400-01; and the Stratagene SURFZAP phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., *Bio/Technology* 9:1370-1372 (1991); Hay et al., *Hum. Antibod. Hybridomas* 3:81-85 (1992); Huse et al., *Science* 246:1275-1281 (1989); McCafferty et al., *Nature* 348:552-554 (1990); Griffiths et al., *EMBO J.* 12:725-734 (1993); Hawkins et al., *J. Mol. Biol.* 226:889-896 (1992); Clackson et al., *Nature* 352:624-628 (1991); Gram et al., *Proc. Natl. Acad. Sci. USA* 89:3576-3580 (1992); Garrad et al., *Bio/Technology* 9:1373-1377 (1991);

Hoogenboom et al., *Nuc. Acid Res.* 19:4133-4137 (1991); and Barbas et al., *Proc. Natl. Acad. Sci. USA* 88:7978-7982 (1991), all incorporated herein by reference.

In one embodiment, to isolate and produce human anti-myostatin antibodies with the desired characteristics, a human anti-myostatin antibody as described herein is first used to select human heavy and light chain sequences having similar binding activity toward myostatin, using the epitope imprinting methods described in PCT Publication No. WO 93/06213, incorporated herein by reference. The antibody libraries used in this method are preferably scFv libraries prepared and screened as described in PCT Publication No. WO 92/01047, McCafferty et al., *Nature* 348:552-554 (1990); and Griffiths et al., *EMBO J.* 12:725-734 (1993), all incorporated herein by reference. The scFv antibody libraries preferably are screened using human myostatin as the antigen.

Once initial human $V_L$ and $V_H$ domains are selected, "mix and match" experiments are performed, in which different pairs of the initially selected $V_L$ and $V_H$ segments are screened for myostatin binding to select preferred $V_L/V_H$ pair combinations. Additionally, to further improve the quality of the antibody, the $V_L$ and $V_H$ segments of the preferred $V_L/V_H$ pair(s) can be randomly mutated, preferably within the CDR3 region of $V_H$ and/or $V_L$, in a process analogous to the in vivo somatic mutation process responsible for affinity maturation of antibodies during a natural immune response. This in vitro affinity maturation can be accomplished by amplifying $V_H$ and $V_L$ domains using PCR primers complimentary to the $V_H$ CDR3 or $V_L$ CDR3, respectively, which primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be re-screened for binding to myostatin.

Following screening and isolation of an anti-myostatin antibody of the invention from a recombinant immunoglobulin display library, nucleic acids encoding the selected antibody can be recovered from the display package (e.g., from the phage genome) and subcloned into other expression vectors by standard recombinant DNA techniques. If desired, the nucleic acid can further be manipulated to create other antibody forms of the invention, as described below. To express a recombinant human antibody isolated by screening of a combinatorial library, the DNA encoding the antibody is cloned into a recombinant expression vector and introduced into a mammalian host cells, as described above.

Class Switching

Another aspect of the invention provides a method for converting the class or subclass of an anti-myostatin antibody to another class or subclass. In some embodiments, a nucleic acid molecule encoding a $V_L$ or $V_H$ that does not include sequences encoding $C_L$ or $C_H$ is isolated using methods well-known in the art. The nucleic acid molecule then is operatively linked to a nucleic acid sequence encoding a $C_L$ or $C_H$ from a desired immunoglobulin class or subclass. This can be achieved using a vector or nucleic acid molecule that comprises a $C_L$ or $C_H$ chain, as described above. For example, an anti-myostatin antibody that was originally IgM can be class switched to an IgG. Further, the class switching may be used to convert one IgG subclass to another, e.g., from IgG1 to IgG2. Another method for producing an antibody of the invention comprising a desired isotype comprises the steps of isolating a nucleic acid encoding a heavy chain of an anti-myostatin antibody and a nucleic acid encoding a light chain of an anti-myostatin antibody, isolating the sequence encoding the $V_H$ region, ligating the $V_H$ sequence to a sequence encoding a heavy chain constant domain of the desired isotype, expressing the light chain gene and the heavy chain construct in a cell, and collecting the anti-myostatin antibody with the desired isotype.

Deimmunized Antibodies

In another aspect of the invention, the antibody may be deimmunized to reduce its immunogenicity using the techniques described in, e.g., PCT Publication Nos. WO98/52976 and WO00/34317 (incorporated herein by reference).

Mutated Antibodies

In another embodiment, the nucleic acid molecules, vectors and host cells may be used to make mutated anti-myostatin antibodies. The antibodies may be mutated in the variable domains of the heavy and/or light chains, e.g., to alter a binding property of the antibody. For example, a mutation may be made in one or more of the CDR regions to increase or decrease the $K_D$ of the antibody for myostatin, to increase or decrease $k_{off}$, or to alter the binding specificity of the antibody. Techniques in site-directed mutagenesis are well-known in the art. See, e.g., Sambrook et al. and Ausubel et al., supra. In another embodiment, one or more mutations are made at an amino acid residue that is known to be changed compared to the germline in monoclonal antibody 1_116_1, 1_136_3, 1_257_1, 1_46_1, 2_112_1, 1_314_1, 1_66_1, 2_43_1, 2_177_1, 1_132_1, 1_268_1, 1_116_1L-Q45K; 1_257_1L-L21I; 1_314_1H-T92A; 1_46_1H-L81M; 2_112_1H-I12V; 2_112_1L-F58I; 2_112_1L-I85V; 2_112_1H-L81M, L-F58I; 2_112_1H-L81M, L-I85V; or 2_112_1H-L81M, L-F58I, I85V. The mutations may be made in a CDR region or framework region of a variable domain, or in a constant domain. In a preferred embodiment, the mutations are made in a variable domain. In some embodiments, one or more mutations are made at an amino acid residue that is known to be changed compared to the germline in a CDR region or framework region of a variable domain of an amino acid sequence selected from SEQ ID NO: 2, 4, 6, 8, 10, 12, 14, 16, 18, 20, 22, 24, 26, 28, 30, 32, 34, 36, 38, 40, 42, 44, 45, 47, 49, 51, 53, 55, 57, 59, 61, 63, 65, 67, 69, 71, 73, 75, 77, 79, 81, 83, 85 or 87 or whose nucleic acid sequence is presented in SEQ ID NO: 1, 3, 5, 7, 9, 11, 13, 15, 17, 19, 21, 23, 25, 27, 29, 31, 33, 35, 37, 39, 41, 43, 46, 48, 50, 52, 54, 56, 58, 60, 62, 64, 66, 68, 70, 72, 74, 76, 78, 80, 82, 84, 86 or 88.

In another embodiment, the framework region is mutated so that the resulting framework region(s) have the amino acid sequence of the corresponding germline gene. A mutation may be made in a framework region or constant domain to increase the half-life of the anti-myostatin antibody. See, e.g., PCT Publication No. WO 00/09560, incorporated herein by reference. A mutation in a framework region or constant domain also can be made to alter the immunogenicity of the antibody, to provide a site for covalent or non-covalent binding to another molecule, or to alter such properties as complement fixation, FcR binding and antibody-dependent cell-mediated cytotoxicity (ADCC). According to the invention, a single antibody may have mutations in any one or more of the CDRs or framework regions of the variable domain or in the constant domain.

In some embodiments, there are from 1 to 8, including any number in between, amino acid mutations in either the $V_H$ or $V_L$ domains of the mutated anti-myostatin antibody compared to the anti-myostatin antibody prior to mutation. In any of the above, the mutations may occur in one or more CDR regions. Further, any of the mutations can be conservative amino acid substitutions. In some embodiments, there are no more than 5, 4, 3, 2, or 1 amino acid changes in the constant domains.

Modified Antibodies

In another embodiment, a fusion antibody or immunoadhesin may be made that comprises all or a portion of an anti-myostatin antibody of the invention linked to another polypeptide. In a preferred embodiment, only the variable domains of the anti-myostatin antibody are linked to the polypeptide. In another preferred embodiment, the $V_H$ domain of an anti-myostatin antibody is linked to a first polypeptide, while the $V_L$ domain of an anti-myostatin antibody is linked to a second polypeptide that associates with the first polypeptide in a manner such that the $V_H$ and $V_L$ domains can interact with one another to form an antigen binding site. In another preferred embodiment, the $V_H$ domain is separated from the $V_L$ domain by a linker such that the $V_H$ and $V_L$ domains can interact with one another (see below under Single Chain Antibodies). The $V_H$-linker-$V_L$ antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

To create a single chain antibody, (scFv) the $V_H$- and $V_L$-encoding DNA fragments are operatively linked to another fragment encoding a flexible linker, e.g., encoding the amino acid sequence $(Gly_4-Ser)_3$, (SEQ ID NO:122) such that the $V_H$ and $V_L$ sequences can be expressed as a contiguous single-chain protein, with the $V_L$ and $V_H$ domains joined by the flexible linker. See, e.g., Bird et al., *Science* 242:423-426 (1988); Huston et al., *Proc. Natl. Acad. Sci. USA* 85:5879-5883 (1988); McCafferty et al., *Nature* 348:552-554 (1990). The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to myostatin and to another molecule.

In other embodiments, other modified antibodies may be prepared using anti-myostatin antibody encoding nucleic acid molecules. For instance, "Kappa bodies" (Ill et al., *Protein Eng.* 10: 949-57 (1997)), "Minibodies" (Martin et al., *EMBO J.* 13: 5303-9 (1994)), "Diabodies" (Holliger et al., *Proc. Natl. Acad. Sci. USA* 90: 6444-6448 (1993)), or "Janusins" (Traunecker et al., *EMBO J.* 10:3655-3659 (1991) and Traunecker et al., *Int. J. Cancer* (Suppl.) 7:51-52 (1992)) may be prepared using standard molecular biological techniques following the teachings of the specification.

Bispecific antibodies or antigen-binding fragments can be produced by a variety of methods including fusion of hybridomas or linking of Fab' fragments. See, e.g., Songsivilai & Lachmann, *Clin. Exp. Immunol.* 79: 315-321 (1990), Kostelny et al., *J. Immunol.* 148:1547-1553 (1992). In addition, bispecific antibodies may be formed as "diabodies" or "Janusins." In some embodiments, the bispecific antibody binds to two different epitopes of myostatin. In some embodiments, the bispecific antibody has a first heavy chain and a first light chain from monoclonal antibody 1_116_1, 1_136_3, 1_257_1, 1_46_1, 2_112_1, 1_314_1, 1_66_1, 2_43_1, 2_177_1, 1_132_1, 1_268_1, 1_116_1L-Q45K; 1_257_1L-L21I; 1_314_1H-T92A; 1_46_1H-L81M; 2_112_1H-I12V; 2_112_1L-F58I; 2_112_1L-I85V; 2_112_1H-L81M, L-F58I; 2_112_1H-L81M, L-I85V; or 2_112_1H-L81M, L-F58I, I85V and an additional antibody heavy chain and light chain. In some embodiments, the additional light chain and heavy chain also are from one of the above-identified monoclonal antibodies, but are different from the first heavy and light chains.

In some embodiments, the modified antibodies described above are prepared using one or more of the variable domains or CDR regions from a human anti-myostatin monoclonal antibody provided herein.

Derivatized and Labeled Antibodies

An anti-myostatin antibody or antigen-binding portion of the invention can be derivatized or linked to another molecule (e.g., another peptide or protein). In general, the antibodies or portion thereof are derivatized such that the myostatin binding is not affected adversely by the derivatization or labeling. Accordingly, the antibodies and antibody portions of the invention are intended to include both intact and modified forms of the human anti-myostatin antibodies described herein. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Another type of derivatized antibody is a labeled antibody. Useful detection agents with which an antibody or antigen-binding portion of the invention may be derivatized include fluorescent compounds, including fluorescein, fluorescein isothiocyanate, rhodamine, 5-dimethylamine-1-napthalenesulfonyl chloride, phycoerythrin, lanthanide phosphors and the like. An antibody can also be labeled with enzymes that are useful for detection, such as horseradish peroxidase, β-galactosidase, luciferase, alkaline phosphatase, glucose oxidase and the like. When an antibody is labeled with a detectable enzyme, it is detected by adding additional reagents that the enzyme uses to produce a reaction product that can be discerned. For example, when the agent horseradish peroxidase is present, the addition of hydrogen peroxide and diaminobenzidine leads to a colored reaction product, which is detectable. An antibody can also be labeled with biotin, and detected through indirect measurement of avidin or streptavidin binding. An antibody can also be labeled with a predetermined polypeptide epitope recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

An anti-myostatin antibody can also be derivatized with a chemical group such as polyethylene glycol (PEG), a methyl or ethyl group, or a carbohydrate group. These groups are useful to improve the biological characteristics of the antibody, e.g., to increase serum half-life.

Pharmaceutical Compositions and Kits

The invention also relates to compositions comprising a human anti-myostatin antibody with inhibitory properties.

The antagonist anti-myostatin antibodies of the invention are useful to prevent or treat a wide range of conditions and disorders in which it is desirable to increase skeletal muscle mass and/or bone. In some cases, such conditions and disorders may be age related or disease related. An antagonist anti-myostatin antibody of the invention may be used to treat, prevent or inhibit age-related loss of muscle mass and strength including muscle atrophy that results from, e.g., immobilization.

In addition, an antagonist anti-myostatin antibody of the invention is useful to treat or prevent muscle loss in wasting diseases or other diseases or conditions, associated with loss of muscle mass including, but not limited to, trauma (including muscle, nerve and bone trauma), burns, AIDS, cancer, hip fractures (especially in the elderly), joint replacement, acute knee injuries, arthritis, chronic renal failure (CRF), congestive heart failure (CHF), chronic obstructive pulmonary disease (COPD), multiple sclerosis (MS), Parkinson's Disease, chronic critical illness, central nervous system (CNS) injury, stroke, cachexia, muscular dystrophies syndrome, surgery and joint injury.

Antagonist anti-myostatin antibodies of the invention also are useful to treat metabolic conditions. Such conditions include type 2 diabetes mellitus, metabolic syndromes such as syndrome X, insulin resistance, impaired glucose tolerance, and obesity.

Further, an antagonist anti-myostatin antibody of the invention is useful to treat or prevent disorders associated with bone loss, including but not limited to age- or hormone-related osteoporosis osteopenia, osteoarthritis, and osteoporosis-related fractures.

Treatment may involve administration of one or more inhibitory anti-myostatin monoclonal antibodies of the invention, or antigen-binding fragments thereof, alone or with a pharmaceutically acceptable carrier. Inhibitory anti-myostatin antibodies of the invention and compositions comprising them, can be administered in combination with one or more other therapeutic, diagnostic or prophylactic agents. Additional therapeutic agents include anti-muscular dystrophy agents (including steroids such as prednisone, deflazacort), and anabolic steroids, albuterol, nutritional supplements such as creatine, and antibiotics such as gentamycin. Additional therapeutic agents also include anti-diabetes agents including but not limited to metformin, sulfonylureas, insulin, SYMLIN® (pramlintide), TZDs such as AVANDIA® (rosiglitazone) and ACTOS® (pioglitazone), GLP-1 analogs, such exenitide, and DPP-IV inhibitors, such as LAF237. Further, additional therapeutic agents include anti-osteoporosis agents including but not limit to bisphosphonates such as FOSAMAX® (alendronate) and ACTONEL® (risedronate), MIACALCIN® (calcitonin), EVISTA® (raloxifene), hormonal agents such estrogen and parathyroid. Such additional agents may be included in the same composition or administered separately. As used herein, "pharmaceutically acceptable carrier" means any and all solvents, dispersion media, coatings, antibacterial and antifungal agents, isotonic and absorption delaying agents, and the like that are physiologically compatible. Some examples of pharmaceutically acceptable carriers are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

The compositions of this invention may be in a variety of forms, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the anti-myostatin antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In one embodiment, the antibody is administered in a formulation as a sterile aqueous solution having a pH that ranges from about 5.0 to about 6.5 and comprising from about 1 mg/ml to about 200 mg/ml of antibody, from about 1 millimolar to about 100 millimolar of histidine buffer, from about 0.01 mg/ml to about 10 mg/ml of polysorbate 80, from about 100 millimolar to about 400 millimolar of trehalose, and from about 0.01 millimolar to about 1.0 millimolar of disodium EDTA dihydrate.

The antibodies of the present invention can be administered by a variety of methods known in the art, although for many therapeutic applications, the preferred route/mode of administration is subcutaneous, intramuscular, or intravenous infusion. As will be appreciated by the skilled artisan, the route and/or mode of administration will vary depending upon the desired results.

In certain embodiments, the antibody compositions active compound may be prepared with a carrier that will protect the antibody against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g. *Sustained and Controlled Release Drug Delivery Systems* (J. R. Robinson, ed., Marcel Dekker, Inc., New York, 1978).

In certain embodiments, an anti-myostatin antibody of the invention can be orally administered, for example, with an inert diluent or an assimilable edible carrier. The compound (and other ingredients, if desired) can also be enclosed in a hard or soft shell gelatin capsule, compressed into tablets, or incorporated directly into the subject's diet. For oral therapeutic administration, the anti-myostatin antibodies can be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Additional active compounds also can be incorporated into the compositions. In certain embodiments, an inhibitory anti-myostatin antibody of the invention is co-formulated with and/or co-administered with one or more additional therapeutic agents. These agents include, without limitation, antibodies that bind other targets, antineoplastic agents, antitumor agents, chemotherapeutic agents, peptide analogues that inhibit myostatin, or antibodies or other molecules that bind to Type II membrane receptors and prevent their binding to or activation by myostatin. Such combination therapies may require lower dosages of the inhibitory anti-myostatin antibody as well as the co-administered agents, thus avoiding possible toxicities or complications associated with the various monotherapies.

Inhibitory anti-myostatin antibodies of the invention and compositions comprising them also may be administered in combination with other therapeutic regimens, in particular in combination with exercise and/or dietary (including nutritional) supplements.

In certain embodiments, an inhibiting anti-myostatin antibody of the invention is co-formulated with and/or co-administered with one or more additional therapeutic agents discussed, supra. These agents include those that inhibit myostatin. Further, such combination therapies may also be used to treat, prevent or inhibit any of the aforementioned diseases and conditions. Such combination therapies may require lower dosages of the inhibitory anti-myostatin antibody as well as the co-administered agents, thus avoiding possible toxicities or complications associated with the various monotherapies.

The compositions of the invention may include a "therapeutically effective amount" or a "prophylactically effective amount" of an antibody or antigen-binding portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount may be less than the therapeutically effective amount.

Dosage regimens can be adjusted to provide the optimum desired response (e.g., a therapeutic or prophylactic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the anti-myostatin antibody or portion thereof and the particular therapeutic or prophylactic effect to be achieved, and (b) the limitations inherent in the art of compounding such an antibody for the treatment of sensitivity in individuals.

An exemplary, non-limiting range for a therapeutically or prophylactically effective amount of an antibody or antibody portion of the invention is 0.025 to 50 mg/kg, more preferably 0.1 to 50 mg/kg, more preferably 0.1-25, 0.1 to 10 or 0.1 to 3 mg/kg. In some embodiments, a formulation contains 5 mg/ml of antibody in a buffer of 20 mM sodium citrate, pH 5.5, 140 mM NaCl, and 0.2 mg/ml polysorbate 80. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Another aspect of the present invention provides kits comprising an anti-myostatin antibody or antigen-binding portion of the invention or a composition comprising such an antibody or portion. A kit may include, in addition to the antibody or composition, diagnostic or therapeutic agents. A kit can also include instructions for use in a diagnostic or therapeutic method. In a preferred embodiment, the kit includes the antibody or a composition comprising it and a diagnostic agent that can be used in a method described below. In another preferred embodiment, the kit includes the antibody or a composition comprising it and one or more therapeutic agents that can be used in a method described below.

Diagnostic Methods of Use

In another aspect, the invention provides diagnostic methods. The anti-myostatin antibodies can be used to detect myostatin in a biological sample in vitro or in vivo.

The anti-myostatin antibodies can be used in a conventional immunoassay, including, without limitation, an ELISA, an RIA, flow cytometry, tissue immunohistochemistry, Western blot or immunoprecipitation. The anti-myostatin antibodies of the invention can be used to detect myostatin from humans. In another embodiment, the anti-myostatin antibodies can be used to detect myostatin from, for example, mice, cynomolgus monkeys, rat, dog, quail, chicken, turkey, pig and horse.

The invention provides a method for detecting myostatin in a biological sample comprising contacting the biological sample with an anti-myostatin antibody of the invention and detecting the bound antibody. In one embodiment, the anti-myostatin antibody is directly labeled with a detectable label. In another embodiment, the anti-myostatin antibody (the first antibody) is unlabeled and a second antibody or other molecule that can bind the anti-myostatin antibody is labeled. As is well known to one of skill in the art, a second antibody is chosen that is able to specifically bind the particular species and class of the first antibody. For example, if the anti-myostatin antibody is a human IgG, then the secondary antibody could be an anti-human-IgG. Other molecules that can bind to antibodies include, without limitation, Protein A and Protein G, both of which are available commercially, e.g., from Pierce Chemical Co.

Suitable labels for the antibody or secondary antibody have been disclosed supra, and include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$ or $^3H$.

In other embodiments, myostatin can be assayed in a biological sample by a competition immunoassay utilizing myostatin standards labeled with a detectable substance and an unlabeled anti-myostatin antibody. In this assay, the biological sample, the labeled myostatin standards and the anti-myostatin antibody are combined and the amount of labeled myostatin standard bound to the unlabeled antibody is determined. The amount of myostatin in the biological sample is inversely proportional to the amount of labeled myostatin standard bound to the anti-myostatin antibody.

One can use the immunoassays disclosed above for a number of purposes. For example, the anti-myostatin antibodies can be used to detect myostatin in cultured cells. In a preferred embodiment, the anti-myostatin antibodies are used to determine the amount of myostatin produced by cells that have been treated with various compounds. This method can be used to identify compounds that modulate myostatin protein levels. According to this method, one sample of cells is treated with a test compound for a period of time while another sample is left untreated. If the total level of myostatin is to be measured, the cells are lysed and the total myostatin level is measured using one of the immunoassays described above. The total level of myostatin in the treated versus the untreated cells is compared to determine the effect of the test compound.

A preferred immunoassay for measuring total myostatin levels is flow cytometry or immunohistochemistry. Methods such as ELISA, RIA, flow cytometry, Western blot, immunohistochemistry, cell surface labeling of integral membrane proteins and immunoprecipitation are well known in the art. See, e.g., Harlow and Lane, supra. In addition, the immunoassays can be scaled up for high throughput screening in order to test a large number of compounds for either activation or inhibition of myostatin expression.

The anti-myostatin antibodies of the invention also can be used to determine the levels of myostatin in a tissue or serum. In some embodiments, the tissue is a diseased tissue. In some embodiments of the method, a tissue or a biopsy thereof is excised from a patient. The method comprises the steps of administering a detectably labeled anti-myostatin antibody or a composition comprising them to a patient in need of such a diagnostic test and subjecting the patient to imaging analysis to determine the location of the myostatin-expressing tissues. Imaging analysis is well known in the medical art, and includes, without limitation, x-ray analysis, magnetic resonance imaging (MRI) or computed tomography (CT). The antibody can be labeled with any agent suitable for in vivo imaging, for example a contrast agent, such as barium, which can be used for x-ray analysis, or a magnetic contrast agent, such as a gadolinium chelate, which can be used for MRI or CT. Other labeling agents include, without limitation, radioisotopes, such as $^{99}Tc$. In another embodiment, the anti-myostatin antibody will be unlabeled and will be imaged by administering a second antibody or other molecule that is detectable and that can bind the anti-myostatin antibody. In embodiment, a biopsy is obtained from the patient to determine whether the tissue of interest expresses myostatin.

Therapeutic Methods of Use

In another embodiment, the invention provides a method for inhibiting myostatin activity by administering an anti-myostatin antibody to a patient in need thereof. Any of the types of antibodies described herein may be used therapeutically. In various embodiments, the anti-myostatin antibody is a human, chimeric or humanized antibody. In a preferred embodiment, the myostatin is human and the patient is a human patient. Alternatively, the patient may be a mammal that expresses a myostatin that the anti-myostatin antibody cross-reacts with. The antibody may be administered to a non-human mammal expressing myostatin with which the antibody cross-reacts (i.e. a rat, a mouse, or a cynomolgus monkey) for veterinary purposes or as an animal model of human disease. Such animal models may be useful for evaluating the therapeutic efficacy of antibodies of this invention.

These antibodies may be used in promoting muscle growth, weight gain and aiding in the prevention of frailty in livestock (cattle, swine, sheep, horses, chickens, turkeys and fish) and companion animals (dogs, cats and horses).

In another embodiment, the invention provides a method for promoting muscle growth, weight gain and aiding in the prevention of frailty in cattle, swine, sheep, chickens, turkeys, horses, fish, dogs and cats in need thereof comprising the step of administering to said subject an antibody or antigen-binding portion as described herein.

As used herein, the term "a condition that may be prevented or treated by reducing myostatin activity" is intended to include diseases and other disorders in which the presence of high levels of myostatin in a subject suffering from the disorder has been shown to be or is suspected of being either responsible for the pathophysiology of the disorder or a factor that contributes to a worsening of the disorder. Such disorders may be evidenced, for example, by an increase in the levels of myostatin in tissues and fluids or phosphorylated Smad 2 or 3 in muscle tissue in the affected cells or tissues of a subject suffering from the disorder. The increase in myostatin levels may be detected, for example, using an anti-myostatin antibody as described above.

In another preferred embodiment, an anti-myostatin antibody may be administered to a patient who expresses inappropriately high levels of myostatin. It is known in the art that high-level expression of myostatin can lead to a variety of wasting conditions, bone loss and to accumulation of fat mass. In one embodiment, said method relates to the treatment of diseases and conditions in which it is desirable to decrease the loss of or to increase skeletal muscle mass, to decrease bone loss or to increase bone mass and/or to reduce fat mass by neutralizing the effects of myostatin. Such conditions and diseases are mentioned supra.

In another preferred embodiment, an anti-myostatin antibody may be administered to a patient who does not express inappropriate levels of myostatin (high or low), but whose condition would still be successfully treated or prevented by using anti-myostatin treatment. In one embodiment, said method relates to the treatment of diseases and conditions in which it is desirable to inhibit myostatin activity to treat the loss of or to improve skeletal muscle mass, to treat bone loss or to increase bone mass and/or to treat fat mass by neutralizing the effects of myostatin. Such diseases and conditions are known in the art and would include diseases and conditions that associate with a variety of wasting conditions that can include bone loss and accumulation of fat mass, e.g., age-related degenerative diseases and non-degenerative, normal age-related conditions.

The antibody may be administered once, but more preferably is administered multiple times. The antibody may be administered from three times daily to once every six months or longer. The administering may be on a schedule such as three times daily, twice daily, once daily, once every two days, once every three days, once weekly, once every two weeks, once every month, once every two months, once every three months and once every six months. The antibody may also be administered continuously via a minipump. The antibody may be administered via an oral, mucosal, buccal, intranasal, inhalable, intravenous, subcutaneous, intramuscular or parenteral route. The antibody may be administered once, at least twice or for at least the period of time until the condition is treated, palliated or cured. The antibody generally will be administered for as long as the condition is present. The antibody will generally be administered as part of a pharmaceutical composition as described supra. The dosage of antibody will generally be in the range of 0.1-100 mg/kg, more preferably 0.5-50 mg/kg, more preferably 1-20 mg/kg, and even more preferably 1-10 mg/kg. The serum concentration of the antibody may be measured by any method known in the art.

Co-administration of the antibody with an additional therapeutic agent (combination therapy) encompasses administering a pharmaceutical composition comprising the anti-myostatin antibody and the additional therapeutic agent as well as administering two or more separate pharmaceutical compositions, one comprising the anti-myostatin antibody and the other(s) comprising the additional therapeutic agent(s). Further, although co-administration or combination therapy generally means that the antibody and additional therapeutic agents are administered at the same time as one another, it also encompasses instances in which the antibody and additional therapeutic agents are administered at different times. For instance, the antibody may be administered once every three days, while the additional therapeutic agent is administered once daily. Alternatively, the antibody may be administered prior to or subsequent to treatment of the disorder with the additional therapeutic agent, for example after a patient has failed therapy with the additional agent. Similarly, administration of the anti-myostatin antibody may be administered prior to or subsequent to other therapy, such as exercise and/or dietary (including nutritional) supplements. The antibody and one or more additional therapeutic agents (the combination therapy) may be administered once, twice or at least the period of time until the condition is treated, palliated or cured. Preferably, the combination therapy is administered multiple times. The combination therapy may be administered from three times daily to once every six months. The administering may be on a schedule such as three times daily, twice daily, once daily, once every two days, once every three days, once weekly, once every two weeks, once every month, once every two months, once every three months and once every six months, or may be administered continuously via a minipump. The combination therapy may be administered via an oral, mucosal, buccal, intranasal, inhalable, intravenous, subcutaneous, intramuscular or parenteral route.

Gene Therapy

The nucleic acid molecules of the present invention can be administered to a patient in need thereof via gene therapy. The therapy may be either in vivo or ex vivo. In a preferred embodiment, nucleic acid molecules encoding both a heavy chain and a light chain are administered to a patient. In a more preferred embodiment, the nucleic acid molecules are administered such that they are stably integrated into chromosomes of B cells because these cells are specialized for producing antibodies. In a preferred embodiment, precursor B cells are transfected or infected ex vivo and re-transplanted into a patient in need thereof. In another embodiment, precursor B cells or other cells are infected in vivo using a virus known to infect the cell type of interest. Typical vectors used for gene therapy include liposomes, plasmids and viral vectors. Exemplary viral vectors are retroviruses, adenoviruses and adeno-associated viruses. After infection either in vivo or ex vivo, levels of antibody expression can be monitored by taking a sample from the treated patient and using any immunoassay known in the art or discussed herein.

In a preferred embodiment, the gene therapy method comprises the steps of administering an isolated nucleic acid molecule encoding the heavy chain or an antigen-binding portion thereof of an anti-myostatin antibody and expressing the nucleic acid molecule. In another embodiment, the gene therapy method comprises the steps of administering an isolated nucleic acid molecule encoding the light chain or an antigen-binding portion thereof of an anti-myostatin antibody and expressing the nucleic acid molecule. In a more preferred method, the gene therapy method comprises the steps of administering of an isolated nucleic acid molecule encoding the heavy chain or an antigen-binding portion thereof and an isolated nucleic acid molecule encoding the light chain or the antigen-binding portion thereof of an anti-myostatin antibody of the invention and expressing the nucleic acid molecules. The gene therapy method may also comprise the step of administering one or more additional therapeutic agents, such as those mentioned, supra.

In order that this invention may be better understood, the following examples are set forth. These examples are for purposes of illustration only and are not to be construed as limiting the scope of the invention in any manner.

Example I

Generation of Hybridomas Producing
Anti-Myostatin Antibody

Antibodies of the invention were prepared, selected, and assayed as follows:

Eight to ten week old XENOMOUSE® mice were immunized intraperitoneally or in their hind footpads with either a c-terminal mature myostatin (10 μg/dose/mouse) (R&D Systems, Catalog #788-G8) or with a full-length cynomolgus mature myostatin. This dose was repeated seven times over a three to four week period. Four days before fusion, the mice were given a final injection of the myostatin in PBS. The spleen and lymph node lymphocytes from immunized mice were fused with the non-secretory myeloma P3-X63-Ag8.653 cell line, and these fused cells were subjected to HAT selection as previously described (Galfre and Milstein, *Methods Enzymol.* 73:3-46, 1981). A panel of hybridomas was recovered that all secrete myostatin specific human IgG2 or IgG4 antibodies.

GDF8 and GDF11 ELISA Assay Protocol:

ELISA assay was used to detect antibody binding to myostatin or GDF11. Myostatin or GDF11 was coated onto a 96-well Immulon microtiter plate (NUNC-IMMUNO® plate MAXISORP® surface, Nalge Nunc International, Cat. No. 439-454) at 4 μg/ml in 50 mM sodium bicarbonate buffer for overnight at 4° C. Plates were washed, and then blocked with phosphate-buffered saline (PBS) containing 0.1% Tween-20 and 0.5% bovine serum albumin. Antibodies were added to the blocked ELISA plates, incubated for 1 hour, and washed with PBS with Tween-20. Binding was detected by anti-human IgG-horseradish peroxidase (Pierce Cat. No. 31420) followed by the addition of ABTS (Pierce Cat. No. 37615). Colorimetric measurements were performed at 405 nm in a micro-plate reader (We used SpectraMax Plus 384, Molecular Devices).

Eleven hybridomas were selected for further study and were designated 1_116_1, 1_136_3, 1_257_1, 1_46_1, 2_112_1, 1_314_1, 1_66_1, 2_43_1, 2_177_1, 1_132_1, and 1_268_1. The eleven hybridomas were deposited under terms in accordance with the Budapest Treaty with the American Type Culture Collection (ATCC), 10801 University Blvd., Manassas, Va. 20110-2209 on Feb. 10, 2005. The hybridomas have been assigned the following reference numbers:

| Antibody | Hybridoma Identifier | ATCC Reference No. |
|---|---|---|
| 1_116_1 | PF8-1-116-1 (LN 15902) | PTA-6566 |
| 1_132_1 | PF8-1-132-1 (LN 15903) | PTA-6567 |
| 1_136_3 | PF8-1-136-3 (LN 15904) | PTA-6568 |
| 1_257_1 | PF8-1-257-1 (LN 15905) | PTA-6569 |
| 1_268_1 | PF8-1-268-1 (LN 15906) | PTA-6570 |
| 1_314_1 | PF8-1-314-1 (LN 15907) | PTA-6571 |
| 1_46_1 | PF8-1-46-1 (LN 15908) | PTA-6572 |
| 1_66_1 | PF8-1-66-1 (LN 15909) | PTA-6573 |
| 2_112_1 | PF8-2-112-1 (LN 15910) | PTA-6574 |
| 2_43_1 | PF8-2-43-1 (LN 15911) | PTA-6575 |
| 2_177_1 | PF8-2-177-1 (LN 15912) | PTA-6576 |

Example II

Sequences of Anti-Myostatin-Antibodies Prepared in Accordance with the Invention To analyze the structure of antibodies produced in accordance with the invention, nucleic acids were cloned that encode heavy and light chain fragments from hybridomas producing anti-myostatin monoclonal antibodies.

Cloning and sequencing of the antibody variable regions, was accomplished as follows: Poly(A)$^+$ mRNA was isolated using a Fast-Track kit (Invitrogen) from approximately $2 \times 10^5$ hybridoma cells derived from XENOMOUSE® mice immunized with myostatin. cDNA was synthesized from the mRNA by using random primers. The randomly primed cDNA was amplified using human $V_H$ or human Vκ family specific variable domain primers (Marks et al., "Oligonucleotide primers for polymerase chain reaction amplification of human immunoglobulin variable genes and design of family-specific oligonucleotide probes." Eur. J. Immunol. 21:985-991 (1991)) or a universal human $V_H$ primer [MG-30, 5'-CAGGTGCAGCTGGAGCAGTCIGG-3'] (SEQ ID NO: 91), in conjunction with primers specific for the human Cγ2 constant region, MG-40d [5'-GCTGAGGGAGTAGAGTC-CTGAGGA-3'] (SEQ ID NO: 92) or a Cκconstant region [hκP2; as previously described in Green et al., 1994]. Nucleic acid molecules were obtained that encode human heavy and kappa light chain transcripts from the anti-myostatin producing hybridomas by PCR amplification from poly(A$^+$) RNA using the primers described above. The PCR products were cloned into [pCRII (Invitrogen)] using a TA cloning kit (Invitrogen) and both strands were sequenced using Prism dye-terminator sequencing kits (Applied Biosystems Inc) and an ABI 377 sequencing machine (Applied Biosystems Inc). All sequences were analyzed by alignments to the "V BASE sequence directory" (Tomlinson et al., MRC Centre for Protein Engineering, Cambridge, UK) using MACVECTOR (Accelrys, San Diego, Calif.) and GENEWORKS (Hindmarsh, S.A. Australia) software programs.

To obtain the full-length expressed nucleic acid sequence of antibodies produced in accordance with the invention, nucleic acids were cloned that encode full-length heavy and light chain coding regions from hybridomas producing anti-myostatin antibodies. Cloning and sequencing was accomplished as follows: Poly(A)$^+$ mRNA was isolated using an RNeasy Mini Kit (Qiagen) and cDNA synthesized from the mRNA with the Advantage RT-for-PCR kit (BD Biosciences) using oligo(dT) priming. The oligo(dT) primed cDNA was amplified in two independent reactions using degenerate primers designed to hybridize to the 5' untranslated region (5'UTR) of human $V_H$ or human $V_K$ gene segments (TABLE 2A and 2B) in conjunction with non-degenerate primers specific for regions in the 3'UTR of IGHG2 or IGHG4 [G_3UTR_R, 5'TACGTGCCAAGCATCCTCGC] (SEQ ID NO: 93) or IGK [K_3UTR_R, 5'AGGCTGGAACTGAG-GAGCAGGTG] (SEQ ID NO: 94). Amplification was achieved using the Expand High Fidelity PCR kit (Roche) and a PTC-200 DNA Engine (MJ Research) with cycling as follows: 2 minutes at 94° C.; 23× (30 seconds at 94° C., 50 seconds at 52° C., 2 minutes at 72° C.); 8 minutes at 72° C. For both heavy and light chain reactions, the PCR products from two independent PCRs were cloned into pCR2.1 using a TOPO-TA cloning kit (Invitrogen) and both strands of two clones were sequenced using Grills 16$^{th}$ BDTv3.1/dGTP chemistry (Applied Biosystems Inc) and a 3730xl DNA Analyzer (Applied Biosystems Inc).

TABLE 2A

Heavy and Light Chain 5' Amplification Primers:

| Primer Name | Primer Sequence | SEQ ID NO |
|---|---|---|
| VH1a_5UTR_F | CCCTGAGAGCATCAYMYARMAACC | 95 |
| VH3a_5UTR_F | HVTHTCCACTYGGTGATCRGCACTG | 96 |
| VH3c_5UTR_F | ATTYRGTGATCAGSACTGAACASAG | 97 |
| VK1a_5UTR_F | GSARTCAGWCYCWVYCAGGACACAGC | 98 |
| VK2_5UTR_F | CACCAGGKGATTTGCATATTRTCCC | 99 |
| VK3_5UTR_F | ATCAATGCCTGKGTCAGAGCYYTG | 100 |

TABLE 2B

5' Primers used for amplification of anti-myostatin antibody heavy and light chains:

| Clone | Forward Heavy Chain Primer | Forward Light Chain Primer |
|---|---|---|
| 1_116_1 | VH3a_5UTR_F | VK1a_5UTR_F |
| 1_132_1 | VH1a_5UTR_F | VK2_5UTR_F |
| 1_136_3 | VH3a_5UTR_F | VK1a_5UTR_F |
| 1_257_1 | VH3a_5UTR_F | VK1a_5UTR_F |
| 1_314_1 | VH3a_5UTR_F | VK1a_5UTR_F |
| 1_46_1 | VH1a_5UTR_F | VK2_5UTR_F |
| 2_112_1 | VH3c_5UTR_F | VK3_5UTR_F |
| 1_268_1 | VH3a_5UTR_F | VK1a_5UTR_F |
| 1_66_1 | VH3a_5UTR_F | VK1a_5UTR_F |
| 2_177_1 | VH3c_5UTR_F | VK3_5UTR_F |
| 2_43_1 | VH3c_5UTR_F | VK3_5UTR_F |

Gene Utilization Analysis

From the nucleic acid sequence and predicted amino acid sequence of the antibodies, the gene usage was identified for each antibody chain. Table 3 sets forth the gene utilization of selected hybridoma clones of antibodies in accordance with the invention:

TABLE 3

Heavy and Light Chain Gene Segment Utilization:

| Clone | Heavy Chain Gene Utilization | | | | | Kappa Chain Gene Utilization | | |
|---|---|---|---|---|---|---|---|---|
| | SEQ ID NO: | $V_H$ | $D_H$ | $J_H$ | $C_H$ | SEQ ID NO: | $V_K$ | $J_K$ |
| 1_116_1 | 1 | V3-21 | D5-5 | JH4B | G2 | 3 | A30 | JK1 |
| 1_132_1 | 5 | V1-02 | D4-23 | JH6B | G2 | 7 | A3 | JK4 |
| 1_136_3 | 9 | V3-21 | D5-5 | JH4B | G2 | 11 | A30 | JK1 |
| 1_257_1 | 13 | V3-21 | D5-12 | JH6B | G2 | 15 | A30 | JK3 |
| 1_314_1 | 17 | V3-21 | — | JH6B | G2 | 19 | A30 | JK1 |
| 1_46_1 | 21 | V1-02 | D4-23 | JH6B | G2 | 23 | A3 | JK4 |
| 2_112_1 | 25 | V3-23 | D1-7 | JH3B | G4 | 27 | L2 | JK4 |
| 1_268_1 | 29 | V3-21 | D1-26 | JH4B | G2 | 31 | A30 | JK4 |
| 1_66_1 | 33 | V3-21 | D5-5 | JH4B | G2 | 35 | A30 | JK3 |
| 2_177_1 | 37 | V3-21 | D1-7 | JH3B | G4 | 39 | L2 | JK4 |
| 2_43_1 | 41 | V3-23 | D1-7 | JH3B | G4 | 43 | L2 | JK4 |

Mutations that developed during antibody maturation of the framework regions were modified back to the germline sequences as illustrated in the sequence alignment of FIG. 19. Specifically, residue 12 in the heavy chain of monoclonal antibody 2_112_1 (SEQ ID NOs: 26 and 77) was modified from Ile to Val. In the light chain (SEQ ID NOs:28 and 79), residue 58 was modified from Phe to Ile and residue 85 was modified from Ile to Val. Mutagenesis of specific residues of the heavy and light chains of antibody 2_112_1 was carried out by designing primers and using the QuickChange Site Directed Mutagenesis Kit from Stratagene, according to the manufacturer's instructions. Mutations were confirmed by automated sequencing, and mutagenized inserts were subcloned into expression vectors. These expression vectors were transfected into NS0 (ECACC # 85110503) and HEK-293T cells (American Type Culture Collection) to express recombinant antibodies of the invention. The resulting antibody having back-mutated framework regions is designated antibody 2_112_K.

Example III

Inhibition of Myostatin by Human Anti-Myostatin Antibodies

A204 Luciferase Assay

A myostatin responsive reporter gene assay (see, Thies, et al., *Growth Factors*, (2001) 18:251-259.) was used to assess the biological activity of active myostatin in vitro. This assay uses a reporter vector pGL3(CAGA)$_{15}$ coupled to luciferase. The CAGA box sequence (AGCCAGACA) (SEQ ID NO: 101) was reported to be a TGF-β-responsive element in the promoter region of a TGF-β-induced gene, PAI-1. (Zawel, et al. *Mol. Cell*, (1998) 1:611-617). This reporter vector was generated by inserting 15 copies of CAGA boxes into the SmaI and XhoI sites of pGL3-promoter vector (Promega, Cat. No. E1761). The human rhabdomyosarcoma cell line, A204 (ATCC Cell No. HTB-82), was transiently transfected with pGL3(CAGA)15 and CMV p-GAL using Fugene 6 transfection reagent (Roche Diagnostics, Cat. No. 1814443). Transfected cells were cultured in McCoy's 5A medium (Invitrogen, Cat. No. 16600) supplemented with 10% fetal bovine serum, 100 U/ml streptomycin, and 100 µg/ml penicillin for 16 hours. Cells were changed to starvation medium (McCoy's 5A medium with streptomycin, penicillin, and 1 mg/ml bovine serum albumin), and then treated with myostatin, GDF11, or activin for 6 hours at 37° C. Luciferase activity was measured using the DUAL-LIGHT® luciferase assay system (Applied Biosytems, Cat. No. T1004). Myostatin activates the reporter to about 10 fold with EC50 around 8 ng/ml. GDF11 activates the reporter in the very similar response. The neutralization activity of an antibody was determined by preincubating antibody with myostatin for 30 minutes prior to addition to the A204 cells. As shown in FIG. 1, human anti-myostatin antibodies of the invention inhibited myostatin-stimulated luciferase activity in the A204 cells. A similar experiment using GDF11 also was performed to study the specificities of the antibodies of the invention. The data is summarized in the FIG. 1. Most antibodies have much more potent neutralizing activity against GDF8 than GDF11. Monoclonal antibodies 1_46_1 and 1_132_1 neutralize both GDF8 and GDF11 with equal potency.

Example IV

Inhibition of Myostatin by Human Anti-Myostatin Antibodies

L6 Beta-Lactamase Assay

In vitro assays to measure myostatin binding to Type II membrane receptors in the presence of anti-myostatin antibodies were conducted to determine if the anti-myostatin antibodies were capable of inhibiting such binding and their degree of inhibition.

An L6 Aurora reporter assay was performed to assess the biological activity of active myostatin in vitro. L6 myostatin LD10 is a cell line stably expressing a beta-lactamase reporter gene. The promoter region in the inserted reporter consists of 16 copies of Smad-binding element (SBE, GTCTAGAC (SEQ ID NO: 102), Zawel et al., Mol. Cell. 1: 611-17 (1998)). The cells were cultured in DMEM high glucose (Invitrogen, Cat. No. 11995) supplemented with 10% heat-inactivated fetal bovine serum (FBS), 200-400 µg/ml Zeocin, 100 U/ml streptomycin, and 100 µg/ml penicillin. Cells were plated to 96-well plate on day one and changed to the starvation medium (DMEM with Zeocin, streptomycin, penicillin, and 0.1% FBS) in afternoon of the second day. On the morning of the third day, cells were treated with myostatin, GDF11, or activin for 4 hours at 37° C. Aurora CCF2 loading kit was used to analyze beta-lactamase activity according to the manufacture's suggestion (Invitrogen, Cat. No. K1032).

Myostatin activated smad-mediated expression of the reporter to about 2-3 fold with EC50 around 5 ng/ml. GDF11 and activin activated the reporter in the very similar response.

Figure 2:
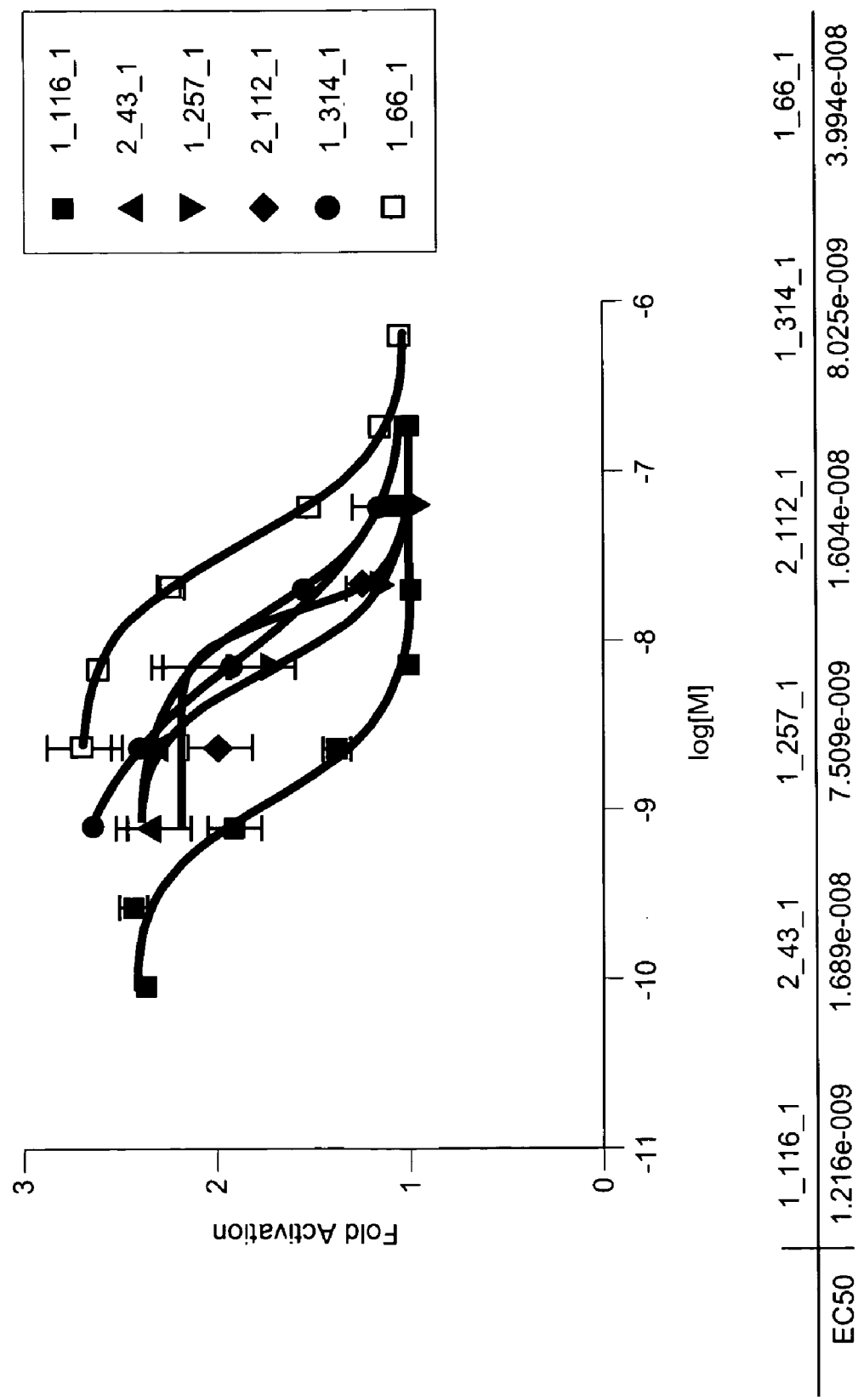
FIG. 2 shows the results of an L6 Aurora beta-lactamase assay. As shown, neutralizing anti-myostatin antibodies inhibit myostatin induced beta-lactamase activity in L6 rat myoblasts. Human antibody variants 1_116_1L-Q45K; 1_257-1L-L21I; 1_314_1H-T92A and 2_112_1H-I12V, L-F58I, I85V inhibited beta-lactamase activity to the same extent as the wild type antibodies.
Figures 10, 11:
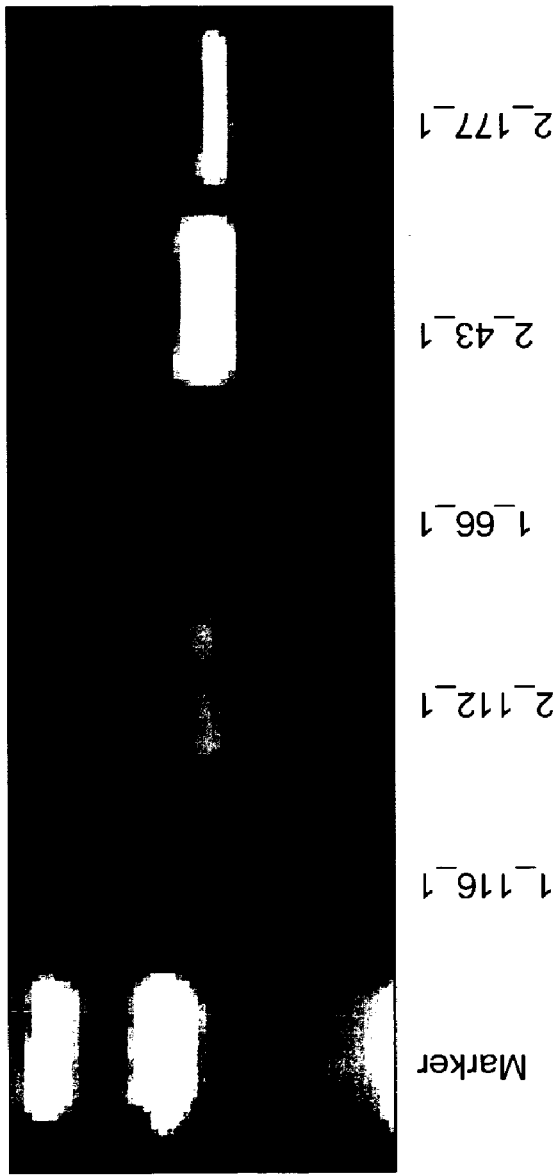
FIG. 10 shows the results of an immunoprecipitation study to test the ability of anti-myostatin antibodies of the invention to pull down mature GDF8 from mouse serum. As shown is the Figure, antibodies 2_112_1, 2_43_1, and 2_177_1 pulled down mature GDF8 from the mouse serum, whereas antibodies 1_116_1, and 1_66_1 could not.
FIG. 11 is a sequence alignment of mature human GDF8 and GDF11. Mature GDF8 (SEQ ID NO: 89) and GDF11 (SEQ ID NO: 90) share approximately 90% identical amino acid sequences. Both mature GDF8 and GDF11 form homodimers. Both mature GDF8 or GDF11 have nine cysteines, which form four internal disulfide bonds and one intermolecular disulfide bond. As shown in the Figure, cysteines that form a disulfide bond with each other are labeled with the same dots or plus. One cysteine (cys73) that forms intermolecular disulfide bond was labeled with a star. GDF8 structure was predicted using SWISS-MODEL (see FIG. 6C).

The neutralization activity of an antibody was determined by preincubating antibody with myostatin for 30 minutes prior to addition to the L6 myostatin LD10 cells. As shown in FIGS. 2 and 11, all human anti-myostatin antibodies tested inhibited smad protein activation in a range from about 1 to about 225 nM.

Example V

Inhibition of Myostatin-Induced Smad 2 Phosphorylation

Western Blot

Figure 3:
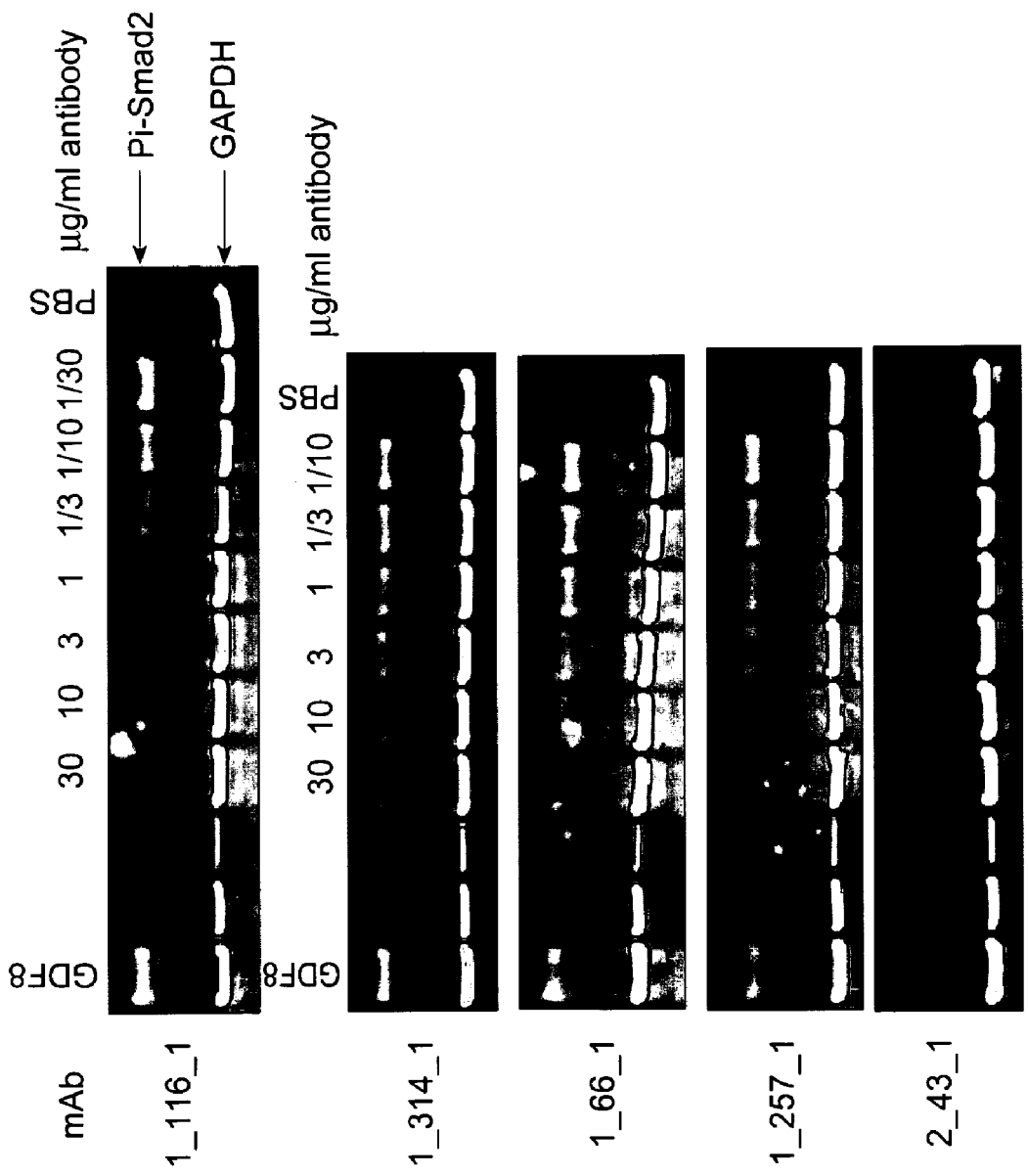
FIG. 3 shows the results of a western blot. As shown, neutralizing anti-myostatin antibodies of the invention inhibit myostatin induced smad2 phosphorylation in HepG2 cells by western blot.

HepG2 human hepatocellular carcinoma cells (ATTC Cell No. HB-8065) were cultured in DMEM high glucose (Invitrogen, Cat. No. 11995) supplemented with 10% fetal bovine serum (FBS), 100 U/ml streptomycin, and 100 µg/ml penicillin. 60-70% confluent cells were changed to the starvation medium (DMEM with streptomycin, penicillin, and 0.5% FBS) overnight. Cells were treated with myostatin for 30 minutes. The neutralization activity of an antibody was determined by preincubating antibody with myostatin for 30 minutes prior to addition to the HepG2 cells. Cells were lysed for western blot. Phosphorylated Smad2 was detected using a rabbit anti-phospho-Smad2 antibody (Cell Signalling, Cat. No. 3101), which was then detected by anti-Rabbit Alex 680 (Molecular Probes, Cat. No. A21076). The amount of phosphorylated Smad2 was quantified using ODYSSEY® Infrared Imager (Li-Cor). Glyseraldehyde-3-phosphate dehydrogenase (GAPDH) was used for normalization. As shown in FIG. 3, all of the neutralizing human anti-myostatin antibodies tested inhibited smad 2 phosphorylation.

Example VI

Enhanced Expression of myf5 by Human Anti-Myostatin Antibodies

Figure 4B:
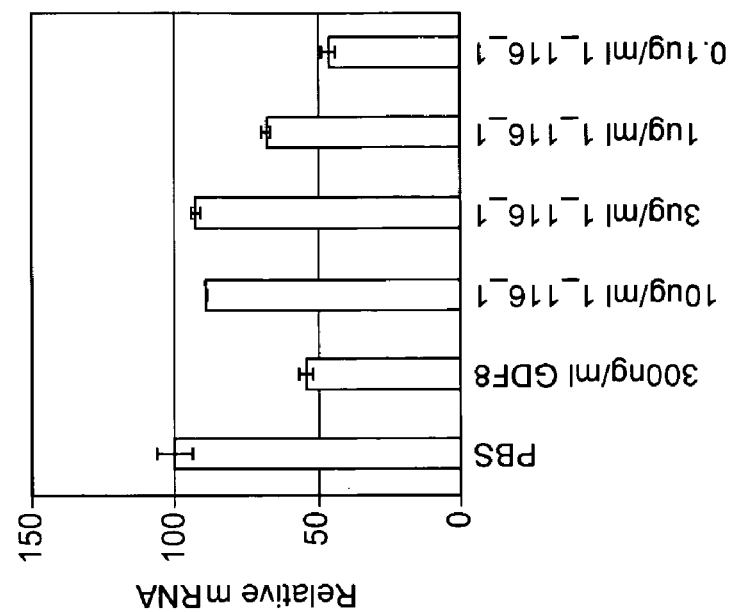
FIG. 4 shows the results of myf5 mRNA expression assays. (A) Neutralizing anti-myostatin antibodies 1_268_1, 2_177_1, and 2_112_1 rescued myf5 gene expression inhibited by myostatin in C2C12 mouse myoblasts, whereas a non-neutralizing antibody 1_159_1 could not. Myf5 mRNA level was detected by TAQMAN® PCR. (B) 1_116_1 rescued myf5 gene expression in a dose-dependent manner.
Figure 4A:
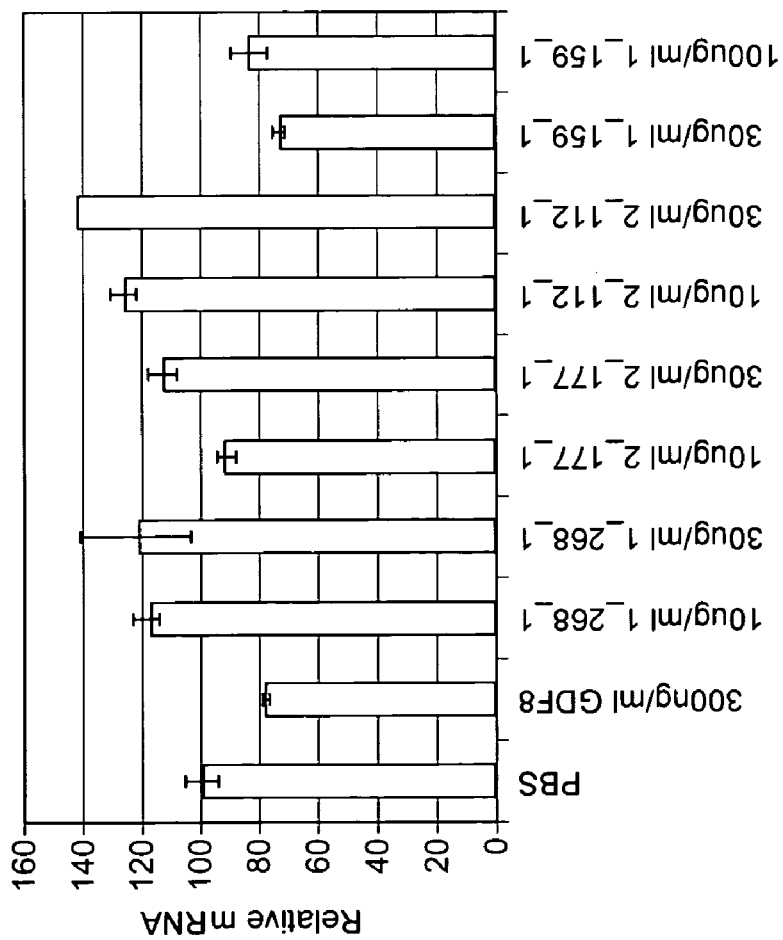

C2C12 myoblasts (ATCC Cell No. CRL-1772) were cultured in DMEM high glucose (Invitrogen, Cat. No. 11995) supplemented with 10% fetal bovine serum (FBS), 100 U/ml streptomycin, and 100 µg/ml penicillin. Cells were treated with 300 ng/ml myostatin for 2 hours. The neutralization activity of an antibody was determined by preincubating antibody with myostatin for 30 minutes prior to addition to the C2C12 cells. Cells were harvested and RNA purified using RNeasy miniprep kit (Qiagen Cat. No. 74104). Purified RNA was quantified with RIBOGREEN® RNA Quantitation Kit (Molecular Probes, Cat. No. R11490). Equal amount of total RNA was used for real time PCR analysis to detect myf5 RNA expression. Primer/probe sets for mouse myf5 RNA detection were purchased from ASSAYS-ON-DEMAND® gene expression products (Applied Biosystems, Cat. No. Hs00271574_m1). Assay conditions used were according to the manufacture's recommendations. One-step RT-PCR was run on the sequence detection system ABI7900 (Applied Biosystems). As shown in FIG. 4, neutralizing human anti-myostatin antibodies of the invention enhanced myf5 expression. One non-neutralizing human anti-myostatin antibody, 1_159_1, did not enhance myf5 expression.

Example VII

Enhancement of Cell Differentiation by Human Anti-Myostatin Antibodies

Figure 5B:
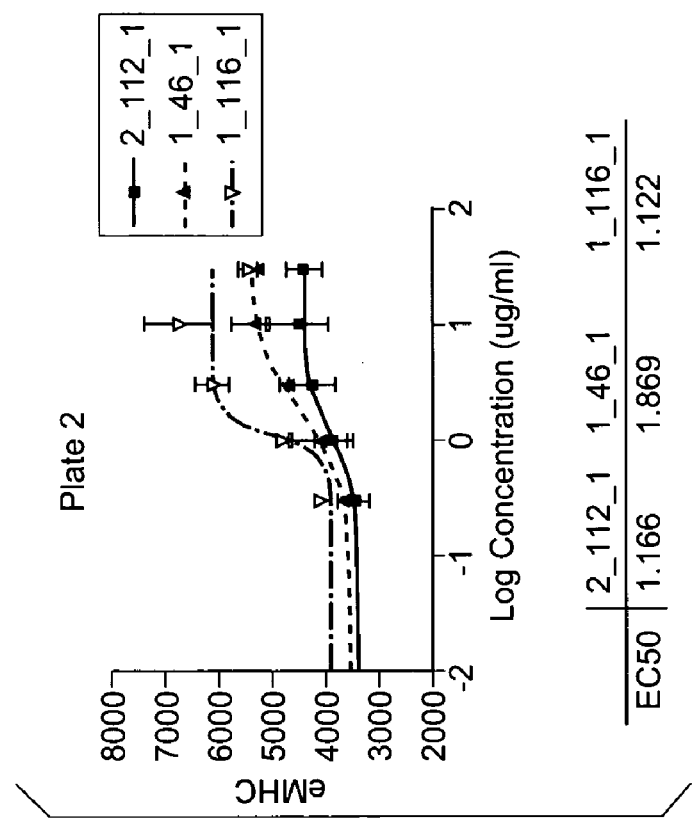
FIG. 5 shows the results of C2C12 muscle cell differentiation assays. (A) Neutralizing anti-myostatin antibodies 2_43_1, 1_314_1, and 1_257_1 rescued myostatin-blocked muscle differentiation in C2C12 mouse muscle cells. Embryonic myosin heavy chain (MHC) protein level was used a marker to measure C2C12 differentiation. (B) Antibodies 2_112_1, 1_46_1, and 1_116_1 rescued myostatin-blocked C2C12 muscle differentiation.
Figure 5A:
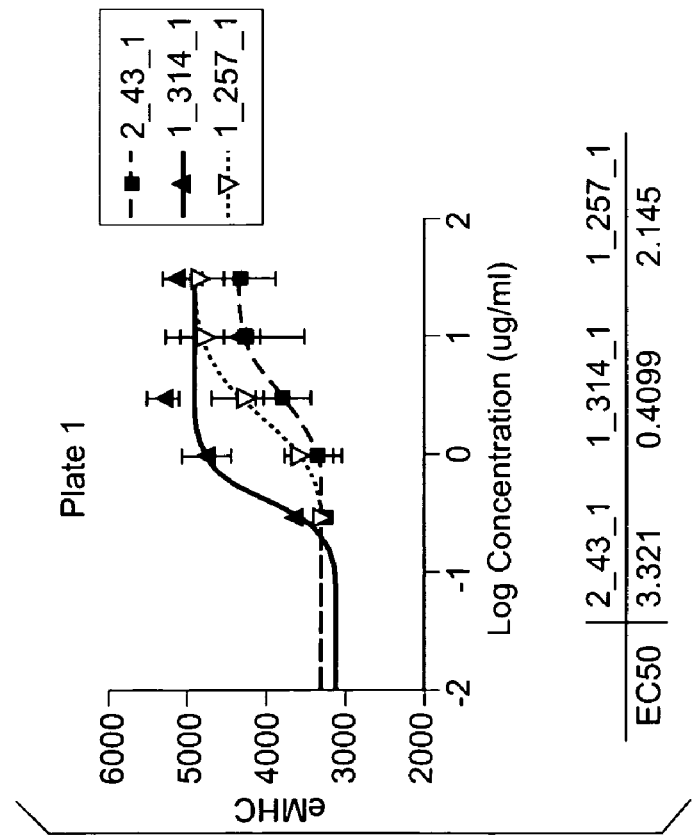

The ability of antibodies to inhibit myostatin-mediated inhibition of myoblast differentiation was assessed in C2C12 myoblasts. C2C12 cells were plated in 96-well plates at 25,000 cells/well in 200 µl DMEM/20% FBS/Penn-Strep. Twenty-four hours later, the media was aspirated, the cells rinsed 1× with HIT media (DMEM/2% horse serum/Penn-Strep), and 200 µl HIT media alone or supplemented with 300 ng/ml GDF-8 (R&D Systems) alone or with various concentrations of antibody added. Forty-eight hours later, the media was aspirated and the cells lysed in 100 µl of lysis buffer (25 mM Tris pH 7.5, 3 mM EDTA, 1% NP-40, 1% Deoxycholate, 0.1% SDS and 1 tablet of Roche Complete protease inhibitor/25 ml of lysis buffer). Embryonic myosin heavy chain (MHC) levels in the lysates were determined by spotting 5 µl of lysate into individual wells of High Bind MA6000 plates (MSD#P11XB-1, Meso Scale Discovery, MSD), air drying for 1 hour, adding 100 µl of Blocker A (MSD#R93BA-2), incubating for 1 hour at 25° C. with shaking, washing 4× with PBS/0.05% Tween-20, adding 50 µl of embryonic MHC antibody (conditioned media from ATCC #CRL-2039 hybridoma), incubating for 1.5 hours at 25° C. with shaking, washing 4× as before, adding 50 µl of Sulfo-TAG Anti-Mouse IgG (MSD #R32AC) which had been diluted 1:1000 in antibody diluent (MSD #R50AA-2), incubating for 1.5 hours at 25° C. with shaking, washing 4× as before, adding 150 µl of 1× Read Buffer (MSD#R92TC-2) and analyzing chemiluminescence in a Sector Imager 6000 (MSD). As shown in FIG. 5, neutralizing human anti-myostatin antibodies reversed myostatin-blocked muscle differentiation in the MHC assay.

Example VIII

Myostatin Peptide Binding

Figure 6:
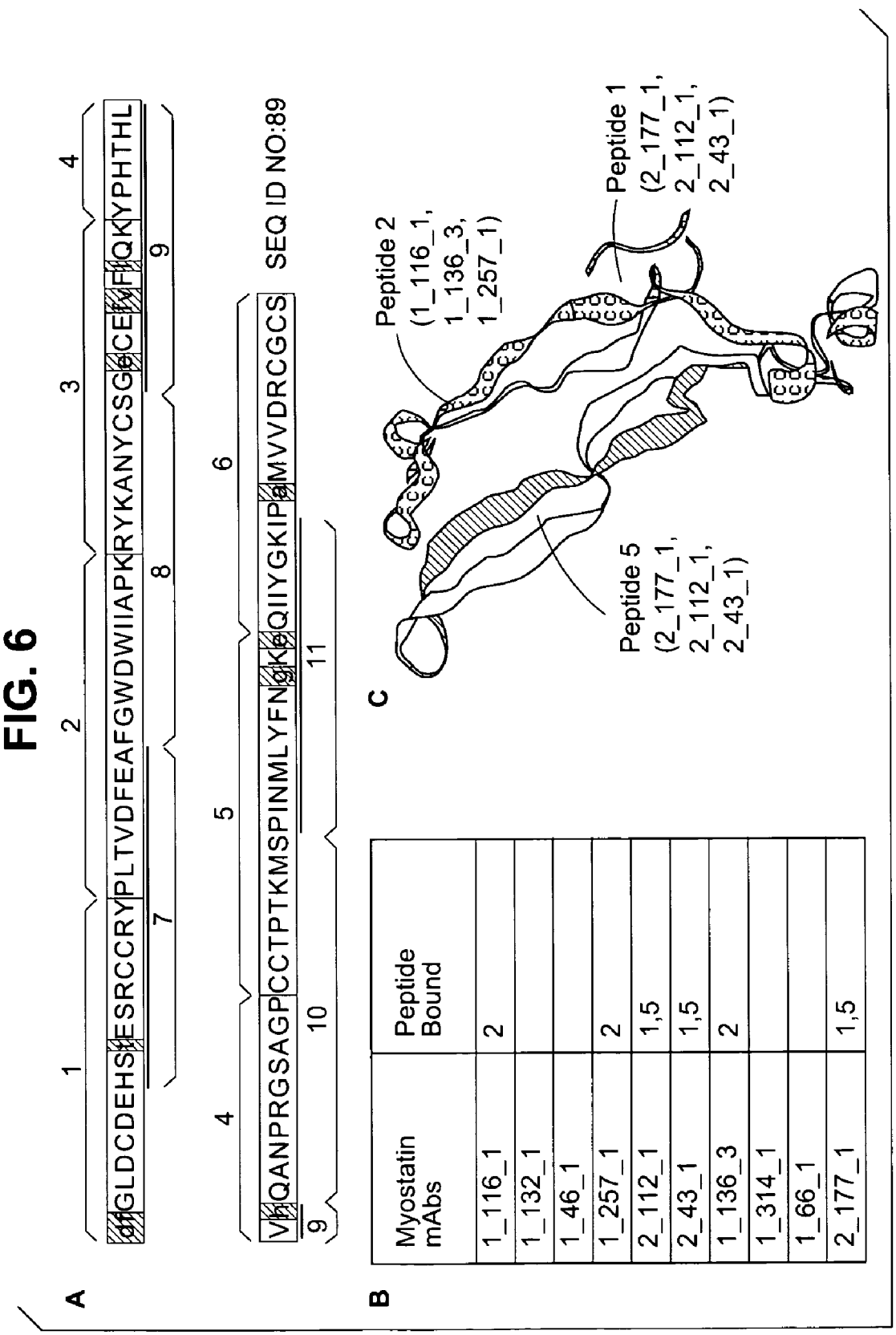
FIG. 6 (A) illustrates peptides generated from mature GDF8 (SEQ ID NO: 89) to test anti-myostatin antibody binding. Amino acids in lower case letters are the amino acids that are different from GDF11 (B) Summary of peptide binding. As shown in the Figure, some antibodies do not bind to any of the peptides. Some antibodies bind to non-contiguous peptides. (C) Predicted GDF8 structure with the illustration of peptide binding of the human anti-myostatin antibodies. GDF8 structure was generated using SWISS-MODEL; a fully automated protein structure homology-modeling server, accessible via the ExPASy web server, or from the program DeepView (Swiss Pdb-Viewer). The first seven amino acids were missing from the predicted structure. Mature GDF8 is a homodimer protein. Only one subunit is shown. The antibodies disclosed herein bind to GDF8 as a homodimer. As shown in the Figure, human monoclonal antibodies 2_43_1, 2_112_1, and 2_177_1 bind to both peptide 1 and 5. Peptides 1 and 5 are proximal spatially but not in primary structure.

Eleven peptides were generated from mature GDF8 to test and localize antibody binding (See FIG. 6). Peptide ELISA was done on glutaraldehyde coated ELISA plates and on uncoated ELISA plates (NUNC-IMMUNO® plate MAXISORP® surface, Nalge Nunc International, Cat. No. 439-454). Glutaraldehyde coated plates were prepared by mixing 250 µl glutaraldehyde (50% w/v) with 50 ml deionized water and adding 200 µl of the solution into each well. Plates were incubated for at least 1 hour at room temperature. The glutaraldehyde was shaken out of the plate and smashed upside down on paper towels to remove all the liquid prior to use.

ELISA plates were coated with peptide at 1.0 µg/well/50 µl (in Sodium bicarbonate buffer, pH 9.6) for at least 4 hours, and then blocked with 200 µl blocker (1% BSA, 1% Ethanolamine pH 7.4) for minimum 4 hours. Plates were washed with PBST three times with 200 µl/well. 50 µl antibody (1 µg/ml in PBST, Phosphate-buffered saline (PBS) with 0.05% Tween-20) sample was added to the wells for 1 hour. Plates were then washed with PBST three times. 50 µl anti-human IgG-horseradish peroxidase (HRP) (Pierce, Cat# 31420) diluted in PBST is added for another hour. The wells were washed again with TBST three times, and then with deionized water twice. 50 ul ABTS (MOSS) was added for 5-20 minutes, and the signal was detected at 405 nm in a colormetric plate reader. The results of the binding experiment are shown in FIG. 6. The eleven peptides are shown in FIG. 7.

Example IX

Epitope Mapping Studies

Cross-competition experiments were performed using the BIACORE® 3000 instrument (Biacore International AB, Uppsala, Sweden and Piscataway, N.J.), following the manufacturer's protocols.

Figure 8:
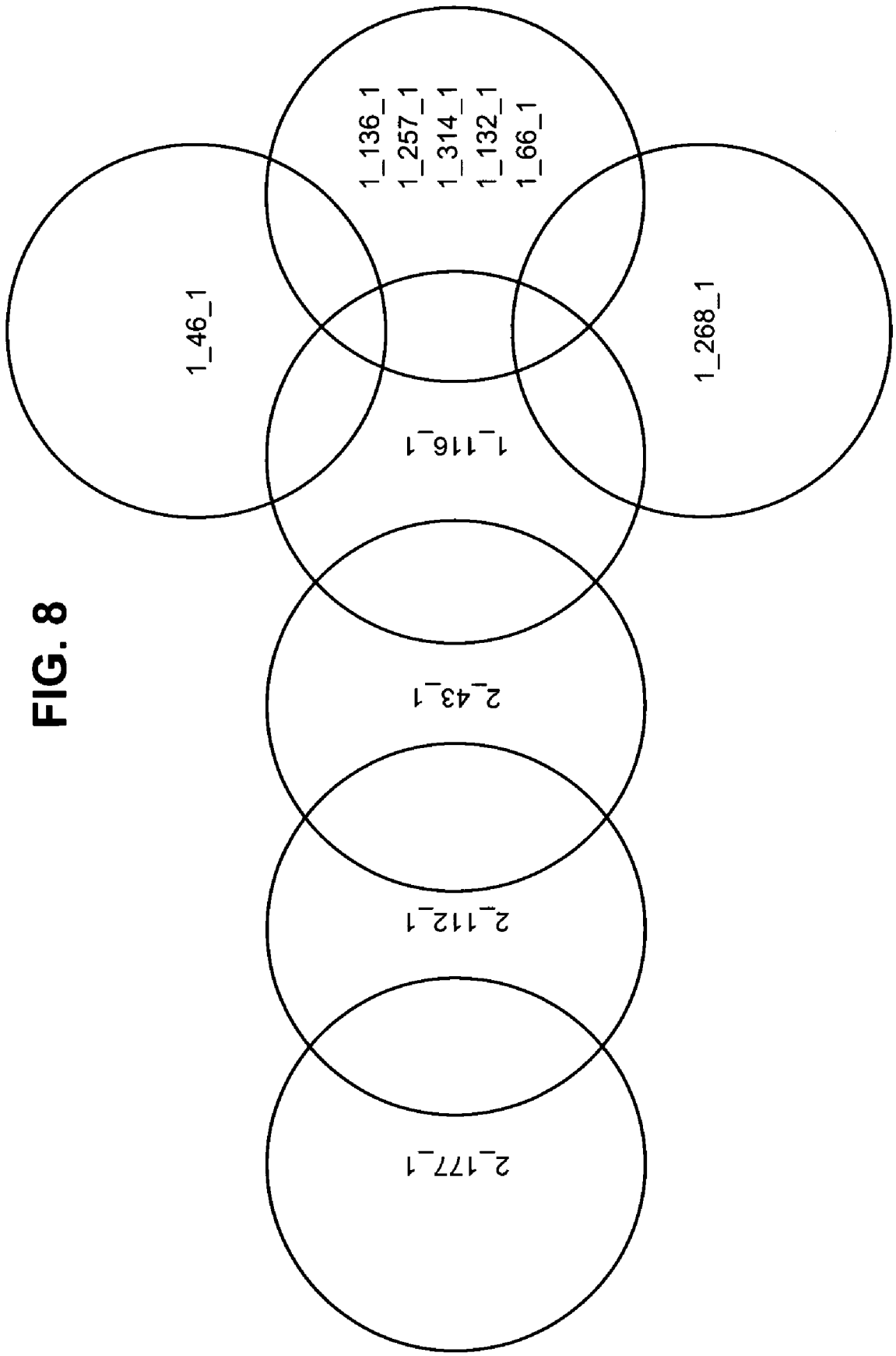
FIG. 8 depicts epitope binning. Epitope binding of the human anti-myostatin antibodies of the invention was mapped by cross-competition experiments using a BIACORE® 3000 instrument. Antibodies are depicted as labeled boxes. Antibodies in one circle compete with antibodies in overlapping circles. For instance, antibody 1_46_1 competes with antibody 1_136_3, but antibody 1_46_1 does not compete with antibody 1_268_1. When two or more antibodies are in the same circle their respective binding cannot be distinguished.

Experiments were performed in a BIACORE® 3000 instrument at 25° C. in 0.01 M HEPES pH 7.4, 0.15 M NaCl, 3 mM EDTA, 0.005% Tween-20. Myostatin was immobilized on a CM5 chip (Biacore™) using standard amine coupling procedures yielding approximately 1300 RU (resonance units). Antibody samples were prepared at 50 nM and injected in pairs, for example, a reference mAb was injected for 10 minutes immediately followed by a 10 minute injection of a test mAb. The surface was regenerated and the injections were repeated in reverse order. The procedure was repeated for all possible pairs of antibodies. A cross-comparison of the total response obtained for a pair of antibodies to that obtained for duplicate injections of each individual antibody was used to find antibodies that competitively bind with one another, e.g., the antibodies compete for binding to the antigen. A response greater than that observed for either of the duplicate injections was indicative of binding to different epitopes whereas a response intermediate to those observed for the duplicate injections was indicative of binding to the same or overlapping or adjacent epitopes. The results of this experiment are shown in FIG. 8 and summarized in FIG. 13.

Example X

Immunoprecipitation of Myostatin from Cell Culture Medium

Figure 9:
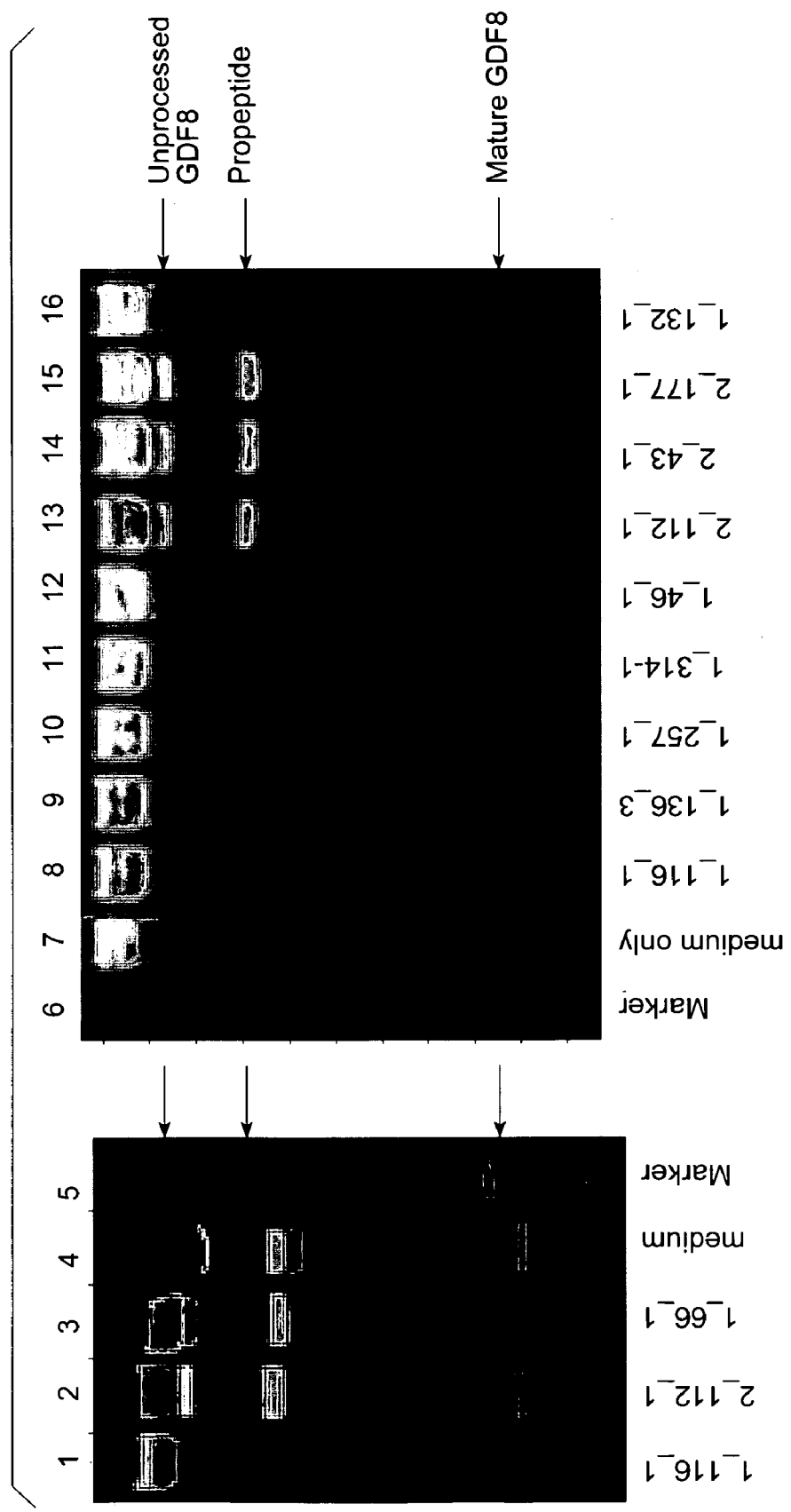
FIG. 9 shows the results of an immunoprecipitation study to test the ability of human anti-myostatin antibodies of the invention to pull down mature GDF8 and mature GDF8/propeptide latent complex. Conditioned medium containing 293T cells transfected with GDF8 was used. As shown in the Figure, antibodies 2_112_1, 2_43_1, and 2_177_1 pulled down mature GDF8, mature GDF8/propeptide complex, and unprocessed GDF8; antibody 1_66_1 pulled down mature GDF8 and mature GDF8/propeptide complex; no other antibodies pulled down mature GDF8, propeptide, or unprocessed GDF8. Lane 4 is the 1/10 medium loading control, and lane 7 is immunoprecipitation control with medium only.

An immunoprecipitation study was conducted to test the binding of myostatin antibodies to mature GDF8 and mature GDF8/propeptide complex. 293T cells were transfected with GDF-8 expression construct. Conditioned media was harvested 7 days after transfection, which contained mature GDF8 and latent complex. 100 µl conditioned media was incubated with 10 µg myostatin antibodies for 16 hours at 4° C. Protein A Dynabeads (Dynal, Norway) were added and incubated for 90 minutes at 4° C. The immunoprecipitate was collected using MPC-E magnetic concentrator (Dynal, Norway), and washed four times with PBS. The immunoprecipitate was resuspended in the reducing sample buffer and loaded on 4-12% Bis-Tris NuPage gel (Invitrogen). Western blotting was performed using ODYSSEY® infrared imaging system (Li-Cor). Mature GDF8 and unprocessed GDF8 were detected using goat anti-myostatin antibody (R&D systems, Cat# AF788). Rabbit anti-propeptide polyclonal antibody (made in-house) was used to detect both propeptide and unprocessed GDF8. As shown in the FIG. 9, antibodies 2_112_1, 2_43_1, and 2_177_1 immunoprecipitated mature GDF8, mature GDF8/propeptide complex, and unprocessed GDF8; antibody 1_66_1 immunoprecipitated mature GDF8 and mature GDF8/propeptide complex. No other antibodies immunoprecipitated mature GDF8, propeptide, or unprocessed GDF8. Lane 4 is the ¹/₁₀ medium loading control, and lane 7 is immunoprecipitation control with medium only.

Example XI

Immunoprecipitation of Myostatin from Mouse Serum

An immunoprecipitation study was conducted to test the binding of myostatin antibodies to mature GDF8 from mouse serum. 200 µl mouse serum (Rockland, Cat ## D208-00) was incubated with 20 µg myostatin antibodies for 16 hours at 4° C. Protein A Dynalbeads were added and incubated for 90 minutes at 4° C. The immunoprecipitate was collected using MPC-E magnetic concentrator (Dynal, Norway), and washed four times with PBS. The immunoprecipitate was resuspended in the reducing sample buffer and loaded on 4-12% Bis-Tris NuPage gel (Invitrogen). Western blotting was performed using ODYSSEY® Infrared imaging system (Li-Cor). Mature GDF8 was detected using biotinylated goat anti-myostatin antibody (R&D systems, Cat# BAF788). As shown in the FIG. 10, antibodies 2_112_1, 2_43_1, and 2_177_1 immunoprecipitated mature GDF8 from the mouse serum, whereas 1_116_1 and 1_66_1 could not. It is known that mature GDF8 in the serum binds to many inhibitory proteins such as propeptide, FLRG, and GASAP1 (Hill et al. (2002) The myostatin propeptide and the follistatin-related gene are inhibitory binding proteins of myostatin in normal serum. J. Biol. Chem. 277: 40735-40741. Hill et al. (2003) Regulation of myostatin in vivo by growth and differentiation factor-associated serum protein-1: a novel protein with protease inhibitor and follistatin domains. Mol. Endocrin. 17(6): 1144-1154). This experiment indicates that antibodies 2_112_1, 2_43_1, and 2_177_1 are truly non-competitive neutralizing antibodies, i.e., the antibodies neutralize myostatin but do not block binding of inhibitory binding proteins present in serum. Such non-competitive neutralizing antibodies would be advantageous in vivo.

Example XII

Comparison of Anti-Myostatin Antibodies In Vivo

Figure 14:
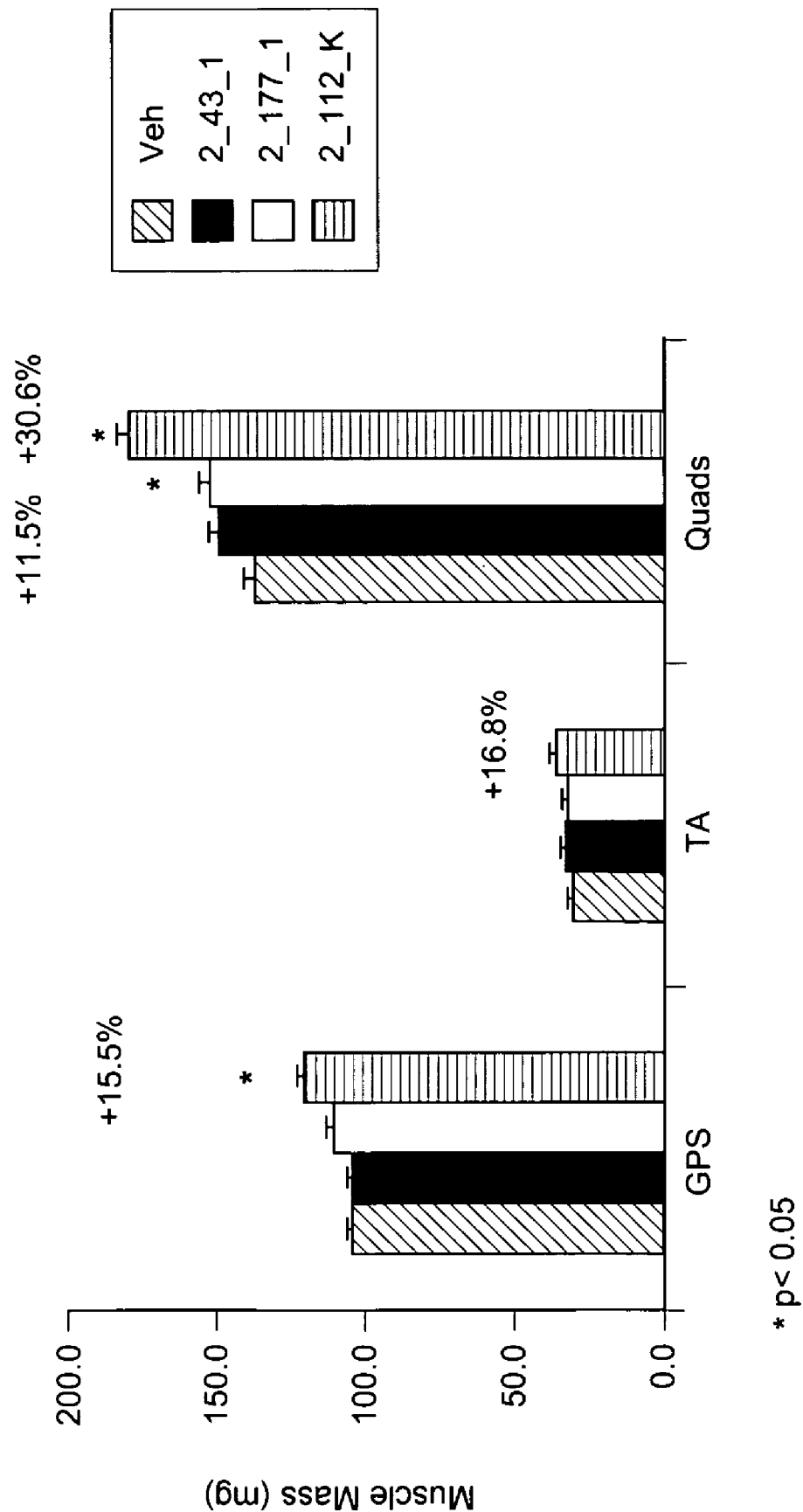

Five week old KKA$^y$/a mice (The Jackson Laboratory (Bar Harbor, Me.)) were treated with 10 mg/kg of monoclonal antibodies 2_43_1, 2_177_1, and 2_112_K or vehicle (PBS) given subcutaneously once per week for five weeks. At the end of the study animals were euthanized and the gastrocnemius-plantaris-soleus (GPS), tibialis anterior (TA) and quadriceps (Quads) muscle groups were dissected and weighed. Treatment with the 2_112_k antibody significantly increased ($p<0.05$) absolute muscle mass for the GPS (+15.5%) and Quads (+30.6%). The 2_177 antibody significantly increased Quads (+11.5%) only. Although TA increased following treatment with antibody 2_112_K (+16.8%), the increase was not statistically significant ($p=0.330$). Body weight increased over the 5 weeks but was not significantly different between treatment groups at any time point during the study. When muscle mass was corrected for body weight (muscle mass index), there were significant differences only with 2_112_K treatment (+11.4% in GPS and +20.6% in Quads). The results of this experiment are shown in FIGS. 14 and 15.

Example XIII

In Vivo Pharmacology and Efficacy of Antibody

Figure 16A:
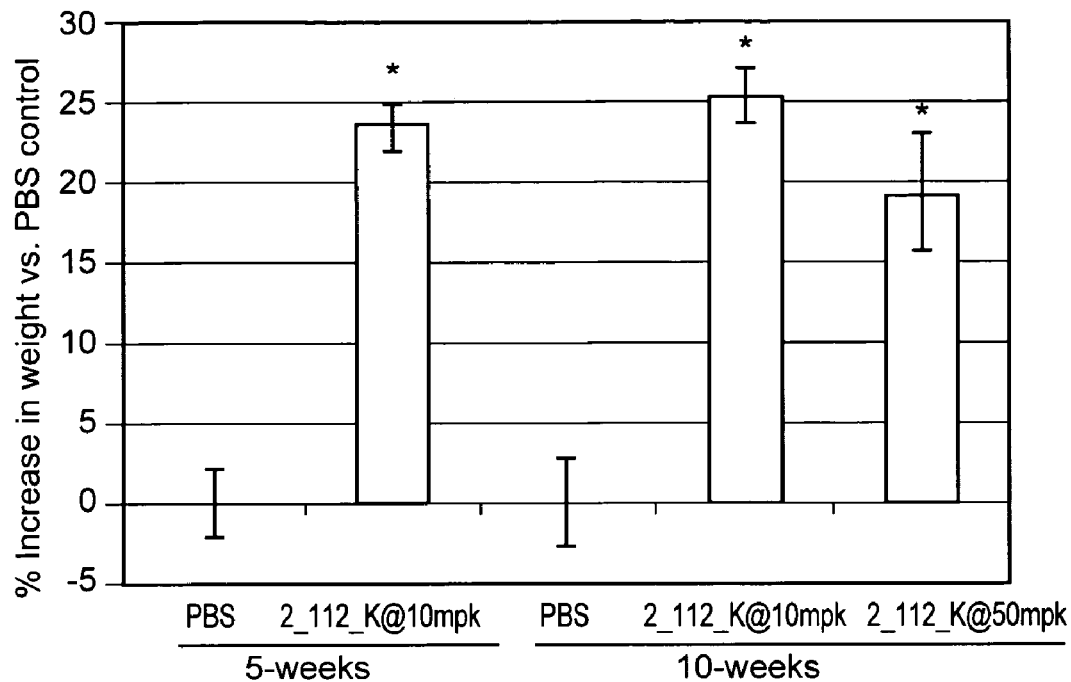
FIG. 16 shows the effects on muscle weight and strength in SCID mice following in vivo treatment with an anti-myostatin antibody (2_112_K).
Figure 16B:
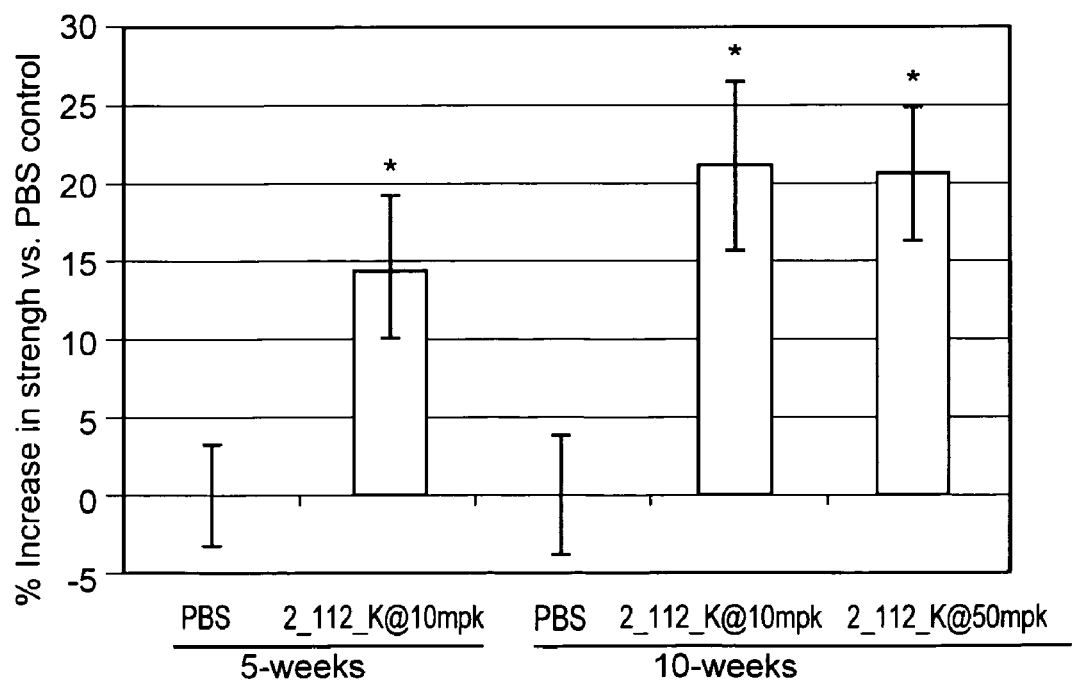
Figure 17A:
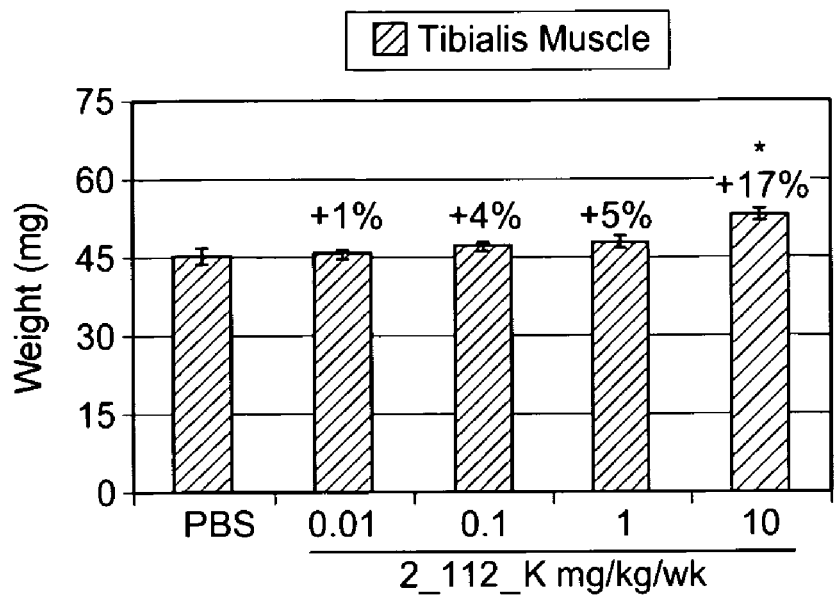
FIG. 17 illustrates the effects on muscle weight in SCID mice following in vivo treatment with varying doses of an anti-myostatin antibody (2_112_K).
Figure 17B:
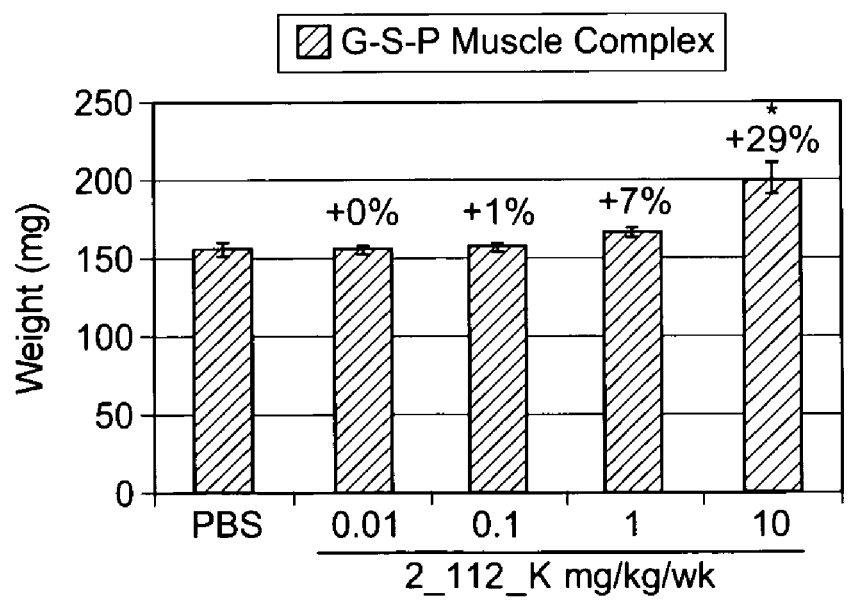
Figure 17C:
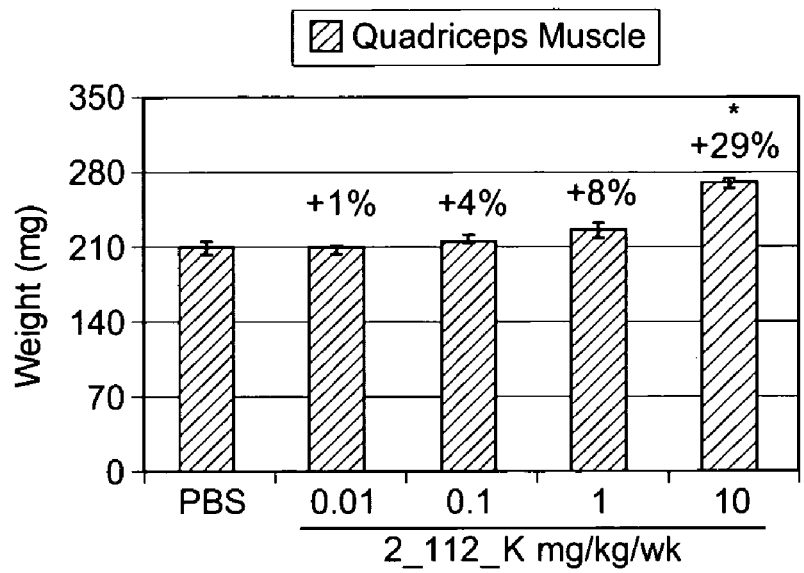
Figure 17D:
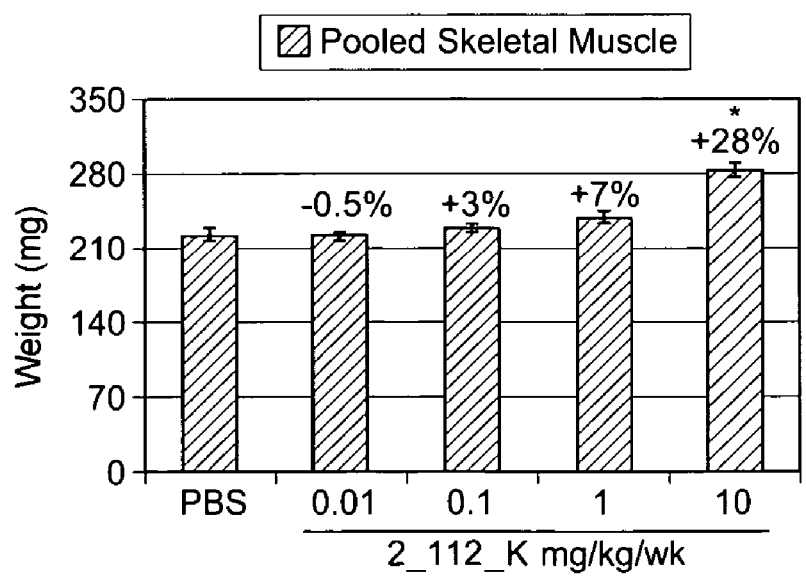

The in vivo pharmacology and efficacy of antibody 2_112_K was evaluated in mice. To avoid potential immunomodulation due to a mouse anti-human antibody (MAHA) response, in vivo studies were performed in immune-deficient Severe Combined Immunodeficient (SCID) beige mice. Subcutaneous administration of antibody 2_112_K to these mice at 10 mg/kg/week s.c. for 5 weeks increased skeletal muscle mass by 19-25% and muscle strength by about 15%. Extending the duration of this treatment to 10 weeks resulted in a further increase in muscle strength to 21% but no further increase in muscle mass (by 18-27%). Also, the Dose of 50 mg/kg/week s.c. for 10 weeks did not yield superior increases in muscle mass or strength compared with 10 mg/kg/week. The results of this experiment are shown in FIG. 16.

Example XIV

Dose and Concentration Response Effects

When administered subcutaneously to SCID mice at doses ranging from no-effect to maximum feasible dose (0.01, 0.1, 1 and 10 mg/kg/week), antibody 2_112_K dose-dependently increased skeletal muscle mass by about 0%, 3%, 7% and 28%, respectively, after 5 weeks (FIG. 17). Extending the duration of treatment to 10 weeks did not result in any further increases in muscle mass but tended to increase tibialis muscle strength marginally by an additional 5%. Also, the antibody dose-dependently altered the body fat composition of these mice by +10%, +1%, −10%, −22% relative to PBS controls at the 0.01, 0.1, 1.0 and 10 mg/kg/week for 5 weeks.

Non-linear, four-parameter analysis of the dose- and concentration-response data yielded estimated ED50 and EC50 values of 3.6 mg/kg/week and 20.4 mg/mL (~136 nM), respectively, assuming the increase in muscle mass achieved with the 10 mg/kg/week dose to be maximum efficacy. The relationship between the dose or serum concentration of antibody 2_112_K versus changes in muscle mass are shown in FIG. 18.

Example XV

Efficacy of Antibody for Attenuation of Muscle Wasting

Ten week old KK mice (JAX laboratories, Bar Harbor, Me.) were randomized into three groups: placebo/vehicle, cortisone/vehicle, and cortisone/antibody 2_112_K. Mice were dosed subcutaneously with either vehicle (PBS) or 10 mg/kg antibody 2_112_K for five weeks followed by implant of a placebo or cortisone pellet. Five days later, mice were euthanized, sacrificed and muscle mass and fat pad mass were assessed. To assess muscle mass, the gastrocnemius-plantaris-soleus (GPS), tibialis anterior (TA) and quadriceps (quads) muscle groups were dissected and weighed. Cortisone implant resulted in a significant decrease (p<0.05) in muscle mass to 85.1±2.2% (GPS), 85.5±3.9% (TA) and 84.1±3.7% (quads) of the placebo/vehicle level. Treatment with antibody 2_112_K ameliorated entirely the cortisone-induced wasting of placebo/vehicle level for GPS ((102.0±2.2%), TA (99.5±3.6) and quads (104.6±2.8%). Values were similar when normalized per gram body weight. To test if this effect was specific for muscle mass, fat pad mass was determined. For fat pad mass, inguinal, epididymal and abdominal fat pads were dissected and weighed. Treatment with antibody 2_112-K did not significantly (p<0.05) spare the loss in fat pad mass due to cortisone implant for inguinal, (cortisone/vehicle (75.1±4.7%) and cortisone/2_112_K, (82.3±5.3%)), epididymal (cortisone/vehicle (79.3±5.0%) and cortisone/2_112_K (87.1±3.9%)), or abdominal, (cortisone/vehicle (79.5±5.5%) and cortisone/2_112_K (82.2±4.2%)), fat pads. Values are expressed relative to placebo/vehicle fat pad. The results of this experiment are shown in FIGS. 20A and 20B.

Example XVI

Protein A Purification of Myostatin Antibody 1-2 liters of concentrated (10-fold) HEK293 media was filtered (2 micron) and loaded on an equilibrated protein A column (Amersham Biosciences, Piscataway, N.J.) (53 mLs, equilibrated with 5 column volumes of D-PBS, pH 7.0) at 2 mL/min. The column was washed with 5 column volumes of acetate buffer (20 mM sodium acetate, pH 5.5) and the protein eluted with 4 column volumes of pH 3.2-3.5 sodium acetate (20 mM). The pH of the eluate was adjusted to pH 5.5 with sodium hydroxide and filtered if needed. Finally the material was concentrated to 10 mg/mL, dialyzed into 140 mM sodium chloride, 20 mM sodium acetate, pH 5.5, filtered and stored at 4 degrees C.

All publications and patent applications cited in this specification are incorporated herein by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated monoclonal antibody or an antigen-binding portion thereof that competes for binding to myostatin with an antibody selected from: 1_116_1 (PTA-6566); 1_136_3 (PTA-6568); 1_257_1 (PTA-6569); 1_46_1 (PTA-6572); 2_112_1 (PTA-6574); 1_314_1 (PTA-6571); 1_66_1 (PTA-6573); 2_43_1 (PTA-6575); 2_177_1 (PTA-6576); 1_132_1 (PTA-6567); or 1_268_1 (PTA-6570).

2. An isolated monoclonal antibody or an antigen-binding portion thereof that specifically binds to myostatin, wherein the antibody or antigen-binding portion thereof comprises (a) the amino acid sequences of the heavy chain CDR1, CDR2, and CDR3 included in SEQ ID NO: 45 and the amino acid sequences of the light chain CDR1, CDR2, and CDR3 included in SEQ ID NO: 47;

(b) the amino acid sequences of the heavy chain CDR1, CDR2, and CDR3 included in SEQ ID NO: 49 and the amino acid sequences of the light chain CDR1, CDR2, and CDR3 included in SEQ ID NO: 51;

(c) the amino acid sequences of the heavy chain CDR1, CDR2, and CDR3 included in SEQ ID NO: 53 and the amino acid sequences of the light chain CDR1, CDR2, and CDR3 included in SEQ ID NO: 55;

(d) the amino acid sequences of the heavy chain CDR1, CDR2, and CDR3 included in SEQ ID NO: 57 and the amino acid sequences of the light chain CDR1, CDR2, and CDR3 included in SEQ ID NO: 59;

(e) the amino acid sequences of the heavy chain CDR1, CDR2, and CDR3 included in SEQ ID NO: 61 and the amino acid sequences of the light chain CDR1, CDR2, and CDR3 included in SEQ ID NO: 63;

(f) the amino acid sequences of the heavy chain CDR1, CDR2, and CDR3 included in SEQ ID NO: 65 and the amino acid sequences of the light chain CDR1, CDR2, and CDR3 included in SEQ ID NO: 67;

(g) the amino acid sequences of the heavy chain CDR1, CDR2, and CDR3 included in SEQ ID NO: 69 and the amino acid sequences of the light chain CDR1, CDR2, and CDR3 included in SEQ ID NO: 71;

(h) the amino acid sequences of the heavy chain CDR1, CDR2, and CDR3 included in SEQ ID NO: 73 and the amino acid sequences of the light chain CDR1, CDR2, and CDR3 included in SEQ ID NO: 75;

(i) the amino acid sequences of the heavy chain CDR1, CDR2, and CDR3 included in SEQ ID NO: 77 and the amino acid sequences of the light chain CDR1, CDR2, and CDR3 included in SEQ ID NO: 79;

(j) the amino acid sequences of the heavy chain CDR1, CDR2, and CDR3 included in SEQ ID NO: 81 and the amino acid sequences of the light chain CDR1, CDR2, and CDR3 included in SEQ ID NO: 83;

(k) the amino acid sequences of the heavy chain CDR1, CDR2, and CDR3 included in SEQ ID NO: 85 and the amino acid sequences of the light chain CDR1, CDR2, and CDR3 included in SEQ ID NO: 87; or (l) the amino acid sequences of the heavy chain CDR1, CDR2, and CDR3 included in SEQ ID NO: 118 and the amino acid sequences of the light chain CDR1, CDR2, and CDR3 included in SEQ ID NO: 120.

3. An isolated monoclonal antibody or an antigen-binding portion thereof that specifically binds to myostatin, wherein:

(a) the heavy chain comprises the heavy chain CDR1, CDR2 and CDR3 amino acid sequences of antibody 2_112_1 (PTA-6574); and (b) the light chain comprises the light chain CDR1, CDR2 and CDR3 amino acid sequences of antibody 2_112_1 (PTA-6574).

4. An isolated monoclonal antibody selected from the group consisting of:

(a) an antibody comprising the amino acid sequences set forth in SEQ ID NO: 2 and SEQ ID NO: 4;

(b) an antibody comprising the amino acid sequences set forth in SEQ ID NO: 6 and SEQ ID NO: 8;

(c) an antibody comprising the amino acid sequences set forth in SEQ ID NO: 10 and SEQ ID NO: 12;

(d) an antibody comprising the amino acid sequences set forth in SEQ ID NO: 14 and SEQ ID NO: 16;

(e) an antibody comprising the amino acid sequences set forth in SEQ ID NO: 18 and SEQ ID NO: 20;

(f) an antibody comprising the amino acid sequences set forth in SEQ ID NO: 22 and SEQ ID NO: 24;
(g) an antibody comprising the amino acid sequences set forth in SEQ ID NO: 26 and SEQ ID NO: 28;
(h) an antibody comprising the amino acid sequences set forth in SEQ ID NO: 30 and SEQ ID NO: 32;
(i) an antibody comprising the amino acid sequences set forth in SEQ ID NO: 34 and SEQ ID NO: 36;
(j) an antibody comprising the amino acid sequences set forth in SEQ ID NO: 38 and SEQ ID NO: 40;
(k) an antibody comprising the amino acid sequences set forth in SEQ ID NO: 42 and SEQ ID NO: 44; and
(l) an antibody comprising the amino acid sequences set forth in SEQ ID NO: 115 and SEQ ID NO: 117.

5. An isolated monoclonal antibody or an antigen-binding portion thereof selected from the group consisting of:
(a) an antibody or an antigen-binding portion comprising the variable domain amino acid sequences contained in SEQ ID NO: 2 and SEQ ID NO: 4;
(b) an antibody or an antigen-binding portion comprising the variable domain amino acid sequences contained in SEQ ID NO: 6 and SEQ ID NO: 8;
(c) an antibody or an antigen-binding portion comprising the variable domain amino acid sequences contained in SEQ ID NO: 10 and SEQ ID NO: 12;
(d) an antibody or an antigen-binding portion comprising the variable domain amino acid sequences contained in SEQ ID NO: 14 and SEQ ID NO: 16;
(e) an antibody or an antigen-binding portion comprising the variable domain amino acid sequences contained in SEQ ID NO: 18 and SEQ ID NO: 20;
(f) an antibody or an antigen-binding portion comprising the variable domain amino acid sequences contained in SEQ ID NO: 22 and SEQ ID NO: 24;
(g) an antibody or an antigen-binding portion comprising the variable domain amino acid sequences contained in SEQ ID NO: 26 and SEQ ID NO: 28;
(h) an antibody or an antigen-binding portion comprising the variable domain amino acid sequences contained in SEQ ID NO: 30 and SEQ ID NO: 32;
(i) an antibody or an antigen-binding portion comprising the variable domain amino acid sequences contained in SEQ ID NO: 34 and SEQ ID NO: 36;
(j) an antibody or an antigen-binding portion comprising the variable domain amino acid sequences contained in SEQ ID NO: 38 and SEQ ID NO: 40;
(k) an antibody or an antigen-binding portion comprising the variable domain amino acid sequences contained in SEQ ID NO: 42 and SEQ ID NO: 44; and
(l) an antibody or an antigen-binding portion comprising the variable domain amino acid sequences contained in SEQ ID NO: 115 and SEQ ID NO: 117.

6. An isolated monoclonal antibody that specifically binds to myostatin, comprising the heavy chain amino acid sequence set forth in SEQ ID NO:115 and the light chain amino acid sequence set forth in SEQ ID NO:117.

7. An isolated monoclonal antibody or an antigen-binding portion thereof comprising the variable regions contained in SEQ ID NO:115 and SEQ ID NO:117.

8. An isolated monoclonal antibody or an antigen-binding portion thereof that specifically binds to myostatin, wherein said antibody comprises the CDR1, CDR2, and CDR3 contained in SEQ ID NO:115 and the CDR1, CDR2 and CDR3 contained in SEQ ID NO:117.

9. An isolated monoclonal antibody or an antigen-binding portion thereof, wherein said monoclonal antibody or antigen-binding portion thereof binds to a myostatin peptide selected from peptide 1 (SEQ ID NO: 103) or peptide 5 (SEQ ID NO:107).

10. An isolated antibody produced by a cell having ATCC Deposit Designation Number selected from the group consisting of PTA-6566, PTA-6567, PTA-6568, PTA-6569, PTA-6570, PTA-6571, PTA-6572, PTA-6573, PTA-6574, PTA-6575, and PTA-6576.

11. A pharmaceutical composition comprising an antibody or an antigen-binding portion thereof according to any one of claims 1 to 5, and 6 to 10 and a pharmaceutically acceptable carrier.

12. A recombinant host cell that produces an antibody or an antigen-binding portion thereof according to any one of claims 1 to 5 and 6 to 10 or the heavy chain or light chain of said antibody or said antigen-binding portion.

13. An isolated monoclonal antibody or an antigen-binding portion thereof that specifically binds myostatin, wherein said monoclonal antibody or antigen-binding portion thereof is cross-reactive with myostatin peptide 1 (SEQ ID NO: 103) and myostatin peptide 5 (SEQ ID NO:107).

14. An isolated monoclonal antibody or an antigen-binding portion thereof that binds to the same epitope of myostatin as an antibody selected from: 1__116__1 (PTA-6566); 1__136__3 (PTA-6568); 1__257__1 (PTA-6569); 1__46__1 (PTA-6572); 2__112__1 (PTA-6574); 1__314__1 (PTA-6571); 1__66__1 (PTA-6573); 2__43__1 (PTA-6575); 2__177__1 (PTA-6576); 1__132__1 (PTA-6567); or 1__268__1 (PTA-6570).

* * * * *